United States Patent
Allan et al.

(10) Patent No.: US 7,740,847 B2
(45) Date of Patent: Jun. 22, 2010

(54) VARIANT FC REGIONS

(75) Inventors: Barrett Allan, Encinitas, CA (US); Weidong Jiang, Sunnyvale, CA (US); Ying Tang, San Diego, CA (US); Jeffry Dean Watkins, Encinitas, CA (US)

(73) Assignee: Applied Molecular Evolution, Inc., San Diego, CA (US)

( * ) Notice: Subject to any disclaimer, the term of this patent is extended or adjusted under 35 U.S.C. 154(b) by 195 days.

(21) Appl. No.: 11/572,634

(22) PCT Filed: Jul. 18, 2005

(86) PCT No.: PCT/US2005/025276

§ 371 (c)(1),
(2), (4) Date: Jan. 25, 2007

(87) PCT Pub. No.: WO2006/020114

PCT Pub. Date: Feb. 23, 2006

(65) Prior Publication Data

US 2007/0224188 A1    Sep. 27, 2007

Related U.S. Application Data

(60) Provisional application No. 60/598,855, filed on Aug. 4, 2004, provisional application No. 60/602,953, filed on Aug. 19, 2004, provisional application No. 60/604,339, filed on Aug. 25, 2004, provisional application No. 60/609,101, filed on Sep. 10, 2004, provisional application No. 60/638,442, filed on Dec. 23, 2004, provisional application No. 60/643,718, filed on Jan. 13, 2005.

(51) Int. Cl.
*A61K 39/395* (2006.01)
*C07K 16/28* (2006.01)
*C07K 16/30* (2006.01)
*C12N 15/13* (2006.01)
*C12N 15/63* (2006.01)
*C12N 15/16* (2006.01)

(52) U.S. Cl. .............. 424/133.1; 424/144.1; 424/153.1; 424/155.1; 424/156.1; 424/173.1; 424/174.1; 424/143.1; 435/69.6; 435/320.1; 435/325; 435/326; 435/328; 435/343.1; 435/344; 435/344.1; 435/358; 530/387.3; 530/388.22; 530/388.73; 530/38.8; 530/388.85; 536/23.53

(58) Field of Classification Search .................. None
See application file for complete search history.

(56) References Cited

U.S. PATENT DOCUMENTS

| | | | |
|---|---|---|---|
| 4,861,579 A | 8/1989 | Meyer et al. |
| 5,348,876 A | 9/1994 | Michaelsen et al. |
| 5,354,847 A | 10/1994 | Liu et al. |
| 5,545,404 A | 8/1996 | Page |
| 5,545,405 A | 8/1996 | Page |
| 5,550,362 A | 8/1996 | Sherman |
| 5,595,721 A | 1/1997 | Kaminski et al. |
| 5,624,821 A | 4/1997 | Winter et al. |
| 5,648,260 A | 7/1997 | Winter et al. |
| 5,677,180 A | 10/1997 | Robinson et al. |
| 5,721,108 A | 2/1998 | Robinson et al. |
| 5,736,137 A | 4/1998 | Anderson et al. |
| 5,776,456 A | 7/1998 | Anderson et al. |
| 5,843,398 A | 12/1998 | Kaminski et al. |
| 5,843,439 A | 12/1998 | Anderson et al. |
| 5,985,599 A | 11/1999 | McKenzie et al. |
| 6,015,542 A | 1/2000 | Kaminski et al. |
| 6,090,365 A | 7/2000 | Kaminski et al. |
| 6,120,767 A | 9/2000 | Robinson et al. |
| 6,121,022 A | 9/2000 | Presta et al. |
| 6,165,745 A | 12/2000 | Ward et al. |
| 6,171,586 B1 | 1/2001 | Lam et al. |
| 6,183,744 B1 | 2/2001 | Goldenberg |
| 6,187,287 B1 | 2/2001 | Leung et al. |
| 6,194,551 B1 | 2/2001 | Idusogie et al. |
| 6,204,023 B1 | 3/2001 | Robinson et al. |
| 6,224,866 B1 | 5/2001 | Barbera-Guillem |
| 6,242,195 B1 | 6/2001 | Idusogie et al. |
| 6,277,375 B1 | 8/2001 | Ward |
| 6,287,537 B1 | 9/2001 | Kaminski et al. |
| 6,306,393 B1 | 10/2001 | Goldenberg |

(Continued)

FOREIGN PATENT DOCUMENTS

WO    WO 88/04936    7/1988

(Continued)

OTHER PUBLICATIONS

Carter et al., "Humanization of an anti-p185HER2 Antibody for Human Cancer Therapy," Proc. Natl. Acad. Sci. USA, vol. 89, No. 10, pp. 4285-4289 (May 1992).

(Continued)

*Primary Examiner*—Ron Schwadron
(74) *Attorney, Agent, or Firm*—Robert L. Sharp; MaryAnn Wiskerchen

(57) ABSTRACT

The present invention provides humanized anti-CD20 antibodies comprising a human IgG1 Fc region comprising an isoleucine at position 247 and a glutamine at position 339 as well as nucleic acids encoding the antibodies and methods of using the antibodies for treating lymphoma. Furthermore, the invention provides compositions comprising the antibodies and methods of producing them.

13 Claims, 8 Drawing Sheets

U.S. PATENT DOCUMENTS

| | | |
|---|---|---|
| 6,399,061 B1 | 6/2002 | Anderson et al. |
| 6,455,043 B1 | 9/2002 | Grillo-Lopez |
| 6,528,624 B1 | 3/2003 | Idusogie et al. |
| 6,538,124 B1 | 3/2003 | Idusogie et al. |
| 6,565,827 B1 | 5/2003 | Kaminski et al. |
| 6,652,852 B1 | 11/2003 | Robinson et al. |
| 6,682,734 B1 | 1/2004 | Anderson et al. |
| 6,737,056 B1 | 5/2004 | Presta |
| 6,821,505 B2 | 11/2004 | Ward |
| 6,893,625 B1 | 5/2005 | Robinson et al. |
| 7,083,784 B2 | 8/2006 | Dall'Acqua et al. |
| 2002/0164326 A1 | 11/2002 | Young et al. |
| 2002/0197256 A1 | 12/2002 | Grewal |
| 2003/0219433 A1 | 11/2003 | Hansen et al. |
| 2004/0002587 A1 | 1/2004 | Watkins et al. |
| 2004/0185045 A1 | 9/2004 | Koenig et al. |
| 2005/0054832 A1 | 3/2005 | Lazar et al. |
| 2005/0202023 A1 | 9/2005 | Ledbetter et al. |
| 2006/0024300 A1 | 2/2006 | Adams et al. |
| 2006/0034836 A1 | 2/2006 | Gillies et al. |
| 2006/0246004 A1 | 11/2006 | Adams et al. |
| 2006/0251652 A1 | 11/2006 | Watkins et al. |

FOREIGN PATENT DOCUMENTS

| | | |
|---|---|---|
| WO | WO 88/07089 | 9/1988 |
| WO | WO 92/07466 | 5/1992 |
| WO | WO 92/16562 | 10/1992 |
| WO | WO 94/11026 | 5/1994 |
| WO | WO 94/29351 | 12/1994 |
| WO | WO 95/03770 | 2/1995 |
| WO | WO 95/05468 | 2/1995 |
| WO | WO 97/28267 | 8/1997 |
| WO | WO 97/34631 | 9/1997 |
| WO | WO 97/44362 | 11/1997 |
| WO | WO 98/05787 | 2/1998 |
| WO | WO 98/23289 | 6/1998 |
| WO | WO 98/52975 | 11/1998 |
| WO | WO 98/56418 | 12/1998 |
| WO | WO 98/58964 | 12/1998 |
| WO | WO 99/22764 | 5/1999 |
| WO | WO 99/51642 | 10/1999 |
| WO | WO 99/58572 | 11/1999 |
| WO | WO 00/09160 | 2/2000 |
| WO | WO 00/09560 | 2/2000 |
| WO | WO 00/20864 | 4/2000 |
| WO | WO 00/27428 | 5/2000 |
| WO | WO 00/27433 | 5/2000 |
| WO | WO 00/29584 | 5/2000 |
| WO | WO 00/42072 | 7/2000 |
| WO | WO 00/44788 | 8/2000 |
| WO | WO 00/67795 | 11/2000 |
| WO | WO 00/67796 | 11/2000 |
| WO | WO 00/74718 | 12/2000 |
| WO | WO 00/76542 A1 | 12/2000 |
| WO | WO 01/03734 A1 | 1/2001 |
| WO | WO 01/10460 A1 | 2/2001 |
| WO | WO 01/10462 | 2/2001 |
| WO | WO 01/13945 A1 | 3/2001 |
| WO | WO 01/74388 | 10/2001 |
| WO | WO 01/79299 | 10/2001 |
| WO | WO 01/80884 A1 | 11/2001 |
| WO | WO 01/97858 A2 | 12/2001 |
| WO | WO 02/34790 A1 | 5/2002 |
| WO | WO 02/060919 A2 | 8/2002 |
| WO | WO 02/060955 A2 | 8/2002 |
| WO | WO 02/079255 A1 | 10/2002 |
| WO | WO 03/002607 A1 | 1/2003 |
| WO | WO 03/061694 A1 | 7/2003 |
| WO | WO 03/068821 A2 | 8/2003 |
| WO | WO 03/074679 A2 | 9/2003 |
| WO | WO 2004/029207 A2 | 4/2004 |
| WO | WO 2004/035607 A2 | 4/2004 |
| WO | WO 2004/056312 A2 | 7/2004 |
| WO | WO 2004/063351 A2 | 7/2004 |
| WO | WO 2004/074455 A2 | 9/2004 |
| WO | WO 2004/091657 A2 | 10/2004 |
| WO | WO 2004/099249 A2 | 11/2004 |
| WO | WO 2004/103404 A1 | 12/2004 |
| WO | WO 2005/000901 A2 | 1/2005 |
| WO | WO 2005/016969 A2 | 2/2005 |
| WO | WO 2005/044859 A2 | 5/2005 |
| WO | WO 2005/056606 A2 | 6/2005 |
| WO | WO 2005/070963 A1 | 8/2005 |
| WO | WO 2005/103081 A2 | 11/2005 |
| WO | WO 2006/019447 A1 | 2/2006 |
| WO | WO 2006/020114 A2 | 2/2006 |
| WO | WO 2006/042240 A2 | 4/2006 |
| WO | WO 2006/053301 A2 | 5/2006 |
| WO | WO 2006/064121 A2 | 6/2006 |
| WO | WO 2006/076651 A2 | 7/2006 |
| WO | WO 2006/084264 A2 | 8/2006 |
| WO | WO 2006/085967 A2 | 8/2006 |
| WO | WO 2006/105338 A2 | 10/2006 |

OTHER PUBLICATIONS

Clynes et al., "Inhibitory Fc Receptors Modulate In Vivo Cytoxicity Against Tumor Targets," Nature Med., vol. 6, No. 4, pp. 443-446 (Apr. 2000).

Eisenberg, R, et al., "The therapeutic potential of anti-CD20 What do B-cells do?," Clinical Immunology, vol. 117, pp. 207-213, 2005.

Glennie, MJ, et al., "Renaissance of cancer therapeutic antibodies," Drug Discovery Today, vol. 8, No. 11, pp. 503-510, (Jun. 1, 2003).

Gopal, AK, et al., "Clinical applications of anti-CD20 antibodies," Journal of Laboratory and Clinical Medicine, vol. 134, No. 5, pp. 445-450, 1999.

Grossbard, ML, et al., "Monoclonal Antibody-Based Therapies of Leukemia and Lymphoma," Blood, vol. 80, No. 4, pp. 863-878 (Aug. 15, 1992).

Hong, K, et al , "Simple quantitative live cell and anti-idiotypic based ELISA for humanized antibody directed to cell surface protein CD20," Journal of Immunological Methods vol. 294, pp. 189-197 (2004).

Idusogie, EE, et al., "Mapping of the C1q Binding Site on Rituxan, A Chimeric Antibody with a Human IgG1 Fc," Journal of Immunology, vol. 164, No. 8, pp, 4178-4184 (2000).

Idusogie, EE, et al., "Engineered Antibodies with Increased Activity to Recruit Complement," Journal of Immunology, vol. 166, No. 4, pp, 2571-2575 (Feb. 15, 2001).

Jones, PT, et al., "Replacing the Complementarity-Determining Regions in a Human Antibody with Those From a Mouse" Nature 321:522-525 (May 29, 1986).

Liu, AY, et al., "Production of a Mouse-Human Chimeric Monoclonal Antibody to CD20 with Potent Fc-Dependent Biologic Activity," Journal of Immunology, vol. 139, No. 10, pp. 3521-3526 (1987).

Longo, DL, "Immunotherapy for non-Hodgkin's lymphoma", Current Opinion in Oncology, vol. 8, pp. 353-359, 1996.

Maloney, DG, et al., "Newer Treatments for Non-Hoggkin's Lymphoma: Monoclonal Antibodies", Oncology, vol. 12, No. 10, Supplement No. 8, pp, 63-76, (Oct. 1998).

Martin, F, et al., "Pathogenic roles of B cells in Human Autoimmunity; Insights from the Clinic," Immunity, vol. 20, No. 5, pp. 517-527 (May 2004).

Nadler, LM, et al., "A Unique Cell Surface Antigen Identifying Lymphoid Malignancies of B Cell Origin," J. Clin. Invest, vol. 67, pp. 134-140, (Jan. 1981).

Paul, WE, "Fv Structure and Diversity in Three Dimensions," Fundamental Immunology, 3$^{rd}$ Edition, pp. 292-295, (1993).

Riechman, L, et al., "Reshaping human antibodies for therapy," Nature, vol. 332, pp. 323-327, (Mar. 1988).

Rudikoff, S, et al., "Single Amino Acid Substitution Altering Antigen-Binding Specificity," Proceedings of the National Academy of Sciences, vol. 79, pp. 1979-1983 (1982).

Shields, RL, et al., "High Resolution Mapping of the Binding Site on Human IgG1 for FcγRI, FcγRII, and FcRn and Design of IgGi Variants with Improved Binding to the FcγR*," Journal of Biological Chemistry, vol. 276, No. 9, pp. 6591-6604, Mar. 2, 2001.

Tedder, TF, et al., "Isolation and Structure of a cDNA Encoding the B1 (CD20) Cell-Surface Antigen of Human B Lymphocytes," Proc. Natl. Acad. Sci. USA, vol. 85, pp. 208-212 (Jan. 1988).

Teeling JL, et al., "Characterization of new human CD20 monoclonal antibodies with potent cytolytic activity against non-Hodgkin's lymphomas," Blood, vol. 104, No. 6, pp. 1793-1800 (Sep. 15, 2004).

Teeling JL, et al., "The Biological Activity of Human CD20 Monoclonal Antibodies Is Linked to Unique Epitopes on CD20[1.]" Journal of Immunology, pp. 362-371 (2006).

Valentine, MA, et al., "Structure and function of the B-cell specific 35-37 kDa CD20 protein," Leukocyte Typing III, McMichael, Ed., Oxford University Press, pp. 440-443 (1987).

Brown, B.A. et al., "Tumor-Specific Genetically Engineered Murine/Human Chimenc Monoclonal Antibody," Cancer Research, vol. 47: pp. 3577-3583 (Jul. 1987).

Datta-Mannan, et al., "Humanized IgGI Variants With Differential Binding Properties to the Neonatal Fc Receptor: Relationship to Pharmacokinetics in Mice and Primates" (2007) *Drug Metabolism and Disposition*, 35:1-9.

Datta-Mannan, et al.. "Monoclonal Antibody Clearance: Impact of modulating the interaction of IgG with FcRn*" *Journal of Biological Chemistry*, 282(3), pp. 1709-17-17 (2007).

Datta-Mannan, et al., Vanant Mabs with enhanced FcRn binding: Disposition in mice and cynomolgus monkeys *2006 AAPS National Biotechnology Meeting*.

Liang, Y, et al., "CD20 as an Immunotherapy Target," *CD20 Wiley Encyclopedia of Molecular Medicine*, pp. 562-564 (Jan. 15, 2002).

Press et al., "Monoclonal Antibody I F5 (Anti-CD20) Serotherapy of Human B Cell Lymphomas" *Blood*, vol. 69:2, pp. 584-591 (Feb. 1987).

FIG. 2

```
                    230                                                      280
humIgG1    PAPELLLGGPSVFLFPPKPKDTLMISRTPEVTCVVVDVSHEDPEVKFNWYV  DGVEVHNAKTKPREEQYNSTYRVVSVLTVLHQDWLNGKEYKCKVSNKALP
humIgG2    PAP-PVAGPSVFLFPPKPKDTLMISRTPEVTCVVVDVSHEDPEVQFNWYV   DGVEVHNAKTKPREEQFNSTFRVSVLTVVVHQDWLNGKEYKCKVSNKGLP
humIgG3    PAPELLGGPSVFLFPPKPKDTLMISRTPEVTCVVVDVSHEDPEVQFKWYV   DGVEVHNAKTKPREEQFNSTFRVVSVLTVLHQDWLNGKEYKCKVSNKALP
humIgG4    PAPEFLGGPSVFLFPPKPKDTLMISRTPEVTCVVVDVSQEDPEVQFNWYV   DGVEVHNAKTKPREEQFNSTYRVVSVLTVLHQDWLNGKEYKCKVSNKGLP
murIgG1    ---TVPEVSSVFIFPPKPKDVLTITLTPKVTCVVVDISKDDPEVQFSWFV   DDVEVHTAQTQPREEQFNSTFRSVSELPIMHQDCLNGKEFKCRVNSAAFP
murIgG2A   PAPNLLGGPSVFIFPPKIKDVLMISLSPIVTCVVVDVSEDDPDVQISWFV   NNVEVHTAQTQTHREDYNSTLRVVSALPIQHQDWMSGKEFKCKVNKDLP
murIgG2B   PAPNLEGGPSVFIFPPNIKDVLMISLTPKVTCVVVDVSEDDPDVQISWFV   NNVEVHTAQTQTHREDYNSTIRVVSHLPIQHQDWMSGKEFKCKVNNKDLP
murIgG3    PPGNLLGGPSVFIFPPKPKDALMISLTPKVTCVVVDVSEDDPDVHVSWFV   DNKEVHTAWTQPREAQYNSTFRVVSALPIQHQDWMRGKEFKCKVNNKALP 330                                                      380
humIgG1    APIEKTISKAKGQPREPQVYTLPPSREEMTKNQVSLTCLVKGFYPSDIAV   EWESNGQPENNYKTTPPVLDSDGSFFLYSKLTVDKSRWQQGNVFSCSVMH
                  D  L
humIgG2    APIEKTISKTKGQPREPQVYTLPPSREEMTKNQVSLTCLVKGFYPSDIAV   EWESSGQPENNYNTTPPMLDSDGSFFLYSKLTVDKSRWQQGNIFSCSVMH
humIgG3    APIEKTISKTKGQPREPQVYTLPPSREEMTKNQVSLTCLVKGFYPSDIAV   EWESNGQPENNYKTTPPVLDSDGSFFLYSKLTVDKSRWQEGNVFSCSVMH
humIgG4    SSIEKTISKAKGQPREPQVYTLPPSQEEMTKNQVSLTCLVKGFYPSDIAV   EWQWNGQPAENYKNTQPIMDTDGSYFVYSKLNVQKSNWEAGNTFTCSVLH
murIgG1    APIEKTISKTKGRPKAPQVYTIPPPKEQMAKDKVSLTCMITDFFPEDITV   EWTNNGKTELNYKNTEPVLDSDGSYFMYSKLRVEKKNWVERNSYSCSVVH
murIgG2A   APIERTISKPKGSVRAPQVYVLPPPEEEMTKKQVTLTCMVTDFMPEDIYV   EWTSNGHTEENYKDTAPVLDSDGSYFIYSKLNMKTSKWEKTDSFSCNVRH
murIgG2B   SPIERTISKPKGLVRAPQVYTLPPPAEQLSRKDVSLTCLVVGFNPGDISV   EWTSNGHTEENYKDTAPVLDSDGSYFIYSKLNMKTSKWEKTDSFSCNVRH
murIgG3    APIERTISKPKGRAQTPQVYTIPPPREQMSKKKKVSLTCLVTNFFSEAISV  EWERNGELEQDYKNTPPILLDSDGTYFLYSKLTVDTDSWLQGEIFTCSVVH 430
humIgG1     EALHNHYTQKSLSLSPGK    (SEQ ID NO:1)
humIgG2     EALHNHYTQKSLSLSPGK    (SEQ ID NO:2)
humIgG3     EALHNRFTQKSLSLSPGK    (SEQ ID NO:3)
humIgG4     EALHNHYTQKSLSLSLGK    (SEQ ID NO:4)
murIgG1     EGLHNHHTEKSLSHSPGK    (SEQ ID NO:5)
murIgG2A    EGLHNHHTTKSFSRTPGK    (SEQ ID NO:6)
murIgG2B    EGLKNYYLKKTISRSPGK    (SEQ ID NO:7)
murIgG3     EALHNHHTQKNLSRSPGK    (SEQ ID NO:8)
```

FIG. 3

A. Parental CH2 (SEQ ID NO:9)

APELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK

B. Parental CH3 (SEQ ID NO:10)
GQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK C. Parental Polypeptide (f allotype) (SEQ ID NO:11)

ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYYCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK

D. Parental Polypeptide (a, z allotype) (SEQ ID NO:12)

ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFFLYSKLTVDKSRW
QQNVFSCSVMHEALHNHYTQKSLSLSPGK

FIG. 4

A. (SEQ ID NO: 13)

EIVLTQSPGT LSLSPGERAT LSCRASSSVP YIHWYQQKPG QAPRLLIYAT
SALASGIPDR FSGSGSGTDF TLTISRLEPE DFAVYYCQQW LSNPPTF

B. (SEQ ID NO: 14)

EVQLVQSGAE VKKPGESLKI SCKGSGRTFT SYNMHWVRQM PGKGLEWMGA
IYPLTGDTSY NQKSKLQVTI SADKSISTAY LQWSSLKASD TAMYYCARST
YVGGDWQFDV W

C. Anti-CD20 LCVR (II) (SEQ ID NO: 15)

QIVLSQSPAI LSASPGEKVT MTCRASSSVS YIHWFQQKPG SSPKPWIYAT
SNLASGVPVR FSGSGSGTSY SLTISRVEAE DAATYYCQQW TSNPPTF

D. Anti-CD20 HCVR (II) (SEQ ID NO: 16)

QVQLQQPGAE LVKAGASVKM SCKASGYTFT SYNMHWVKQT PGRGLEWIGA
IYPGNGDTSY NQKFKGKATL TADKSSSTAY MQLSSLTSED SAVYYCARST
YYGGDWYFNV W

E. Anti-CD20 (I)
   LCVR CDR1 (SEQ ID NO: 17): RASSSVPYIH
   LCVR CDR2 (SEQ ID NO: 18): ATSALAS
   LCVR CDR3 (SEQ ID NO: 19): QQWLSNPPT HCVR CDR1 (SEQ ID NO: 20): GRTFTSYNMH
   HCVR CDR2 (SEQ ID NO: 21): AIYPLTGDTSYNQKSKL
   HCVR CDR3 (SEQ ID NO: 22): STYVGGDWQFDV Anti-CD20 (II)
   LCVR CDR1 (SEQ ID NO: 23): RASSSVSYIH
   LCVR CDR2 (SEQ ID NO: 24): ATSNLAS
   LCVR CDR3 (SEQ ID NO: 25): QQWTSNPPT HCVR CDR1 (SEQ ID NO: 26): GYTFTSYNMH
   HCVR CDR2 (SEQ ID NO: 27): AIYPGNGDTSYNQKFKG
   HCVR CDR3 (SEQ ID NO: 28): STYYGGDWYFNV

FIG. 5

A. SEQ ID NO:29: AME 133 complete light chain amino acid sequence

EIVLTQSPGTLSLSPGERATLSCRASSSVPYIHWYQQKPGQAPRLLIYATSALASGIPDR
FSGSGSGTDFTLTISRLEPEDFAVYYCQQWLSNPPTFGQGTKLEIK<u>RTVAAPSVFIFPPS
DEQLKSGTASVVCLLNNFYPREAKVQWKVDNALQSGNSQESVTEQDSKDSTYSLSSTLTL
SKADYEKHKVYACEVTHQGLSSPVTKSFNRGEC</u>

- Constant Region is underlined

B. SEQ ID NO:30: AME 133 complete light chain nucleic acid sequence

GAAATTGTGTTGACGCAGTCTCCAGGCACCCTGTCTTTGTCTCCAGGGGAAAGAGCCACC
CTCTCCTGCAGGGCCAGCTCAAGTGTACCGTACATCCACTGGTACCAGCAGAAACCTGGC
CAGGCTCCCAGGCTCCTCATCTATGCCACATCCGCTCTGGCTTCTGGCATCCCAGACAGG
TTCAGTGGCAGTGGGTCTGGGACAGACTTCACTCTCACCATCAGCAGACTGGAGCCTGAA
GATTTTGCAGTGTATTACTGTCAGCAGTGGCTGAGTAACCCACCCACTTTTGGCCAGGGG
ACCAAGCTGGAGATCAAACGAACTGTGGCTGCACCATCTGTCTTCATCTTCCCGCCATCT
GATGAGCAGTTGAAATCTGGAACTGCCTCTGTTGTGTGCCTGCTGAATAACTTCTATCCC
AGAGAGGCCAAAGTACAGTGGAAGGTGGATAACGCCCTCCAATCGGGTAACTCCCAGGAG
AGTGTCACAGAGCAGGACAGCAAGGACAGCACCTACAGCCTCAGCAGCACCCTGACGCTG
AGCAAAGCAGACTACGAGAAACACAAAGTCTACGCCTGCGAAGTCACCCATCAGGGCCTG
AGCTCGCCCGTCACAAAGAGCTTCAACAGGGGAGAGTGTTAG

FIG. 6

A. SEQ ID NO:31: AME 133 (247I/339Q variant) complete heavy chain amino acid sequence

EVQLVQSGAEVKKPGESLKISCKGSGRTFTSYNMHWVRQMPGKGLEWMGAIYPLTGDTSY
NQKSKLQVTISADKSISTAYLQWSSLKASDTAMYYCARSTYVGGDWQFDVWGKGTTVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELLG
GPSVFLFPPKIKDTLMISRTPEVTCVVVDVSHEDPEVKFNWYVDGVEVHNAKTKPREEQY
NSTYRVVSVLTVLHQDWLNGKEYKCKVSNKALPAPIEKTISKQKGQPREPQVYTLPPSRD
ELTKNQVSLTCLVKGFYPSDIAVEWESNGQPENNYKTTPPVLDSDGSFFLYSKLTVDKSR
WQQGNVFSCSVMHEALHNHYTQKSLSLSPGK

- Constant Region is underlined; variants are bolded

B. SEQ ID NO:32: AME 133 (247I/339Q variant) complete heavy chain nucleic acid sequence

GAGGTGCAGCTGGTGCAGTCTGGAGCAGAGGTGAAAAAGCCCGGGGAGTCTCTGAAGATC
TCCTGTAAGGGTTCTGGCCGTACATTTACCAGTTACAATATGCACTGGGTGCGCCAGATG
CCCGGGAAAGGCCTGGAGTGGATGGGGGCTATTTATCCCTTGACGGGTGATACTTCCTAC
AATCAGAAGTCGAAACTCCAGGTCACCATCTCAGCCGACAAGTCCATCAGCACCGCCTAC
CTGCAGTGGAGCAGCCTGAAGGCCTCGGACACCGCCATGTATTACTGTGCGAGATCGACT
TACGTGGGCGGTGACTGGCAGTTCGATGTCTGGGGCAAGGGGACCACGGTCACCGTCTCC
TCAGCCTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAAGGTTGAG
CCCAAATCTTGTGACAAAACTCACACATGCCCACCGTGCCCAGCACCTGAACTCCTGGGG
GGACCGTCAGTCTTCCTCTTCCCCCCAAAAATCAAGGACACCCTCATGATCTCCCGGACC
CCTGAGGTCACATGCGTGGTGGTGGACGTGAGCCACGAAGACCCTGAGGTCAAGTTCAAC
TGGTACGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGAATGGC
AAGGAGTACAAGTGCAAGGTCTCCAACAAAGCCCTCCCAGCCCCCATCGAGAAAACCATC
TCCAAACAGAAAGGGCAGCCCCGAGAACCACAGGTGTACACCCTGCCCCCATCCCGGGAC
GAGCTGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCC
GTGCTGGACTCCGACGGCTCCTTCTTCCTCTATAGCAAGCTCACCGTGGACAAGAGCAGG
TGGCAGCAGGGGAACGTCTTCTCATGCTCCGTGATGCATGAGGCTCTGCACAACCACTAC
ACGCAGAAGAGCCTCTCCCTGTCTCCGGGTAAATGA

- Variants are bolded and underlined

FIG. 6

C. SEQ ID NO:33: AME 133 (247I/339D) variant complete heavy chain amino acid sequence

EVQLVQSGAEVKKPGESLKISCKGSGRTFTSYNMHWVRQMPGKGLEWMGAIYPLTGDTSY
NQKSKLQVTISADKSISTAYLQWSSLKASDTAMYYCARSTYVGGDWQFDVWGKGTTVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELLG
GPSVFLFPPKIKDTLMISRTPEVTCVVVDVSHEDPEVKFNWYVDGVEVHNAKTKPREEQY
NSTYRVVSVLTVLHQDWLNGKEYKCKVSNKALPAPIEKTISKDKGQPREPQVYTLPPSRD
ELTKNQVSLTCLVKGFYPSDIAVEWESNGQPENNYKTTPPVLDSDGSFFLYSKLTVDKSR
WQQGNVFSCSVMHEALHNHYTQKSLSLSPGK

- Constant Region is underlined; variants are bolded

D. SEQ ID NO:34: AME 133 (247I/339D) variant complete heavy chain nucleic acid sequence

GAGGTGCAGCTGGTGCAGTCTGGAGCAGAGGTGAAAAAGCCCGGGGAGTCTCTGAAGATC
TCCTGTAAGGGTTCTGGCCGTACATTTACCAGTTACAATATGCACTGGGTGCGCCAGATG
CCCGGGAAAGGCCTGGAGTGGATGGGGGCTATTTATCCCTTGACGGGTGATACTTCCTAC
AATCAGAAGTCGAAACTCCAGGTCACCATCTCAGCCGACAAGTCCATCAGCACCGCCTAC
CTGCAGTGGAGCAGCCTGAAGGCCTCGGACACCGCCATGTATTACTGTGCGAGATCGACT
TACGTGGGCGGTGACTGGCAGTTCGATGTCTGGGGCAAGGGGACCACGGTCACCGTCTCC
TCAGCCTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAAGGTTGAG
CCCAAATCTTGTGACAAAACTCACACATGCCCACCGTGCCCAGCACCTGAACTCCTGGGG
GGACCGTCAGTCTTCCTCTTCCCCCCAAAAATCAAGGACACCCTCATGATCTCCCGGACC
CCTGAGGTCACATGCGTGGTGGTGGACGTGAGCCACGAAGACCCTGAGGTCAAGTTCAAC
TGGTACGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGAATGGC
AAGGAGTACAAGTGCAAGGTCTCCAACAAAGCCCTCCCAGCCCCCATCGAGAAAACCATC
TCCAAAGACAAAGGGCAGCCCCGAGAACCACAGGTGTACACCCTGCCCCCATCCCGGGAC
GAGCTGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCC
GTGCTGGACTCCGACGGCTCCTTCTTCCTCTATAGCAAGCTCACCGTGGACAAGAGCAGG
TGGCAGCAGGGGAACGTCTTCTCATGCTCCGTGATGCATGAGGCTCTGCACAACCACTAC
ACGCAGAAGAGCCTCTCCCTGTCTCCGGGTAAATGA

- Variants are bolded and underlined

FIG. 6

E. SEQ ID NO:35: AME 133 (378D) variant complete heavy chain amino acid sequence

EVQLVQSGAEVKKPGESLKISCKGSGRTFTSYNMHWVRQMPGKGLEWMGAIYPLTGDTSY
NQKSKLQVTISADKSISTAYLQWSSLKASDTAMYYCARSTYVGGDWQFDVWGKGTTVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSRD
ELTKNQVSLTCLVKGFYPSDIDVEWESNGQPENNYKTTPPVLDSDGSFFLYSKLTVDKSR
WQQGNVFSCSVMHEALHNHYTQKSLSLSPGK

- Constant Region is underlined; variant is bolded

F. SEQ ID NO:36: AME 133 (378D) variant complete heavy chain nucleic acid sequence

GAGGTGCAGCTGGTGCAGTCTGGAGCAGAGGTGAAAAAGCCCGGGGAGTCTCTGAAGATC
TCCTGTAAGGGTTCTGGCCGTACATTTACCAGTTACAATATGCACTGGGTGCGCCAGATG
CCCGGGAAAGGCCTGGAGTGGATGGGGGCTATTTATCCCTTGACGGGTGATACTTCCTAC
AATCAGAAGTCGAAACTCCAGGTCACCATCTCAGCCGACAAGTCCATCAGCACCGCCTAC
CTGCAGTGGAGCAGCCTGAAGGCCTCGGACACCGCCATGTATTACTGTGCGAGATCGACT
TACGTGGGCGGTGACTGGCAGTTCGATGTCTGGGGCAAGGGGACCACGGTCACCGTCTCC
TCAGCCTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAAGGTTGAG
CCCAAATCTTGTGACAAAACTCACACATGCCCACCGTGCCCAGCACCTGAACTCCTGGGG
GGACCGTCAGTCTTCCTCTTCCCCCCAAAACCCAAGGACACCCTCATGATCTCCCGGACC
CCTGAGGTCACATGCGTGGTGGTGGACGTGAGCCACGAAGACCCTGAGGTCAAGTTCAAC
TGGTACGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGAATGGC
AAGGAGTACAAGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCCCATCCCGGGAC
GAGCTGACCAAGAACCAGGTCAGCCTGACCTGCCTGGTCAAAGGCTTCTATCCCAGCGAC
ATCGACGTGGAGTGGGAGAGCAATGGGCAGCCGGAGAACAACTACAAGACCACGCCTCCC
GTGCTGGACTCCGACGGCTCCTTCTTCCTCTATAGCAAGCTCACCGTGGACAAGAGCAGG
TGGCAGCAGGGGAACGTCTTCTCATGCTCCGTGATGCATGAGGCTCTGCACAACCACTAC
ACGCAGAAGAGCCTCTCCCTGTCTCCGGGTAAATGA

- Variant is bolded and underlined

SEQUENCE LISTING

```
<160> NUMBER OF SEQ ID NOS: 36

<210> SEQ ID NO 1
<211> LENGTH: 218
<212> TYPE: PRT
<213> ORGANISM: Homo sapiens

<400> SEQUENCE: 1

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175
```

```
Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215
```

<210> SEQ ID NO 2
<211> LENGTH: 217
<212> TYPE: PRT
<213> ORGANISM: Homo sapiens

<400> SEQUENCE: 2

```
Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Lys Val Ser Asn Lys
                85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 3
<211> LENGTH: 218
<212> TYPE: PRT
<213> ORGANISM: Homo sapiens

<400> SEQUENCE: 3

```
Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60
```

```
Glu Gln Phe Asn Ser Thr Phe Arg Val Val Ser Val Leu Thr Val Leu
 65                  70                  75                  80

His Gln Asp Trp Leu Asn Gly Lys Glu Tyr Lys Cys Lys Val Ser Asn
                 85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
        195                 200                 205

Gln Lys Ser Leu Ser Leu Ser Pro Gly Lys
    210                 215

<210> SEQ ID NO 4
<211> LENGTH: 218
<212> TYPE: PRT
<213> ORGANISM: Homo sapiens

<400> SEQUENCE: 4

Pro Ala Pro Glu Phe Leu Gly Gly Pro Ser Val Phe Leu Phe Pro Pro
  1               5                  10                  15

Lys Pro Lys Asp Thr Leu Met Ile Ser Arg Thr Pro Glu Val Thr Cys
             20                  25                  30

Val Val Val Asp Val Ser Gln Glu Asp Pro Glu Val Gln Phe Asn Trp
         35                  40                  45

Tyr Val Asp Gly Val Glu Val His Asn Ala Lys Thr Lys Pro Arg Glu
 50                  55                  60

Glu Gln Phe Asn Ser Thr Tyr Arg Val Val Ser Val Leu Thr Val Leu
 65                  70                  75                  80

His Gln Asp Trp Leu Asn Gly Lys Glu Tyr Lys Cys Lys Val Ser Asn
                 85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
```

<210> SEQ ID NO 5
<211> LENGTH: 215
<212> TYPE: PRT
<213> ORGANISM: Mus sp.

<400> SEQUENCE: 5

Thr Val Pro Glu Val Ser Ser Val Phe Ile Phe Pro Pro Lys Pro Lys
1               5                   10                  15

Asp Val Leu Thr Ile Thr Leu Thr Pro Lys Val Thr Cys Val Val Val
            20                  25                  30

Asp Ile Ser Lys Asp Asp Pro Glu Val Gln Phe Ser Trp Phe Val Asp
        35                  40                  45

Asp Val Glu Val His Thr Ala Gln Thr Gln Pro Arg Glu Glu Gln Phe
    50                  55                  60

Asn Ser Thr Phe Arg Ser Val Ser Glu Leu Pro Ile Met His Gln Asp
65                  70                  75                  80

Cys Leu Asn Gly Lys Glu Phe Lys Cys Arg Val Asn Ser Ala Ala Phe
                85                  90                  95

Pro Ala Pro Ile Glu Lys Thr Ile Ser Lys Thr Lys Gly Arg Pro Lys
            100                 105                 110

Ala Pro Gln Val Tyr Thr Ile Pro Pro Lys Glu Gln Met Ala Lys
        115                 120                 125

Asp Lys Val Ser Leu Thr Cys Met Ile Thr Asp Phe Phe Pro Glu Asp
    130                 135                 140

Ile Thr Val Glu Trp Gln Trp Asn Gly Gln Pro Ala Glu Asn Tyr Lys
145                 150                 155                 160

Asn Thr Gln Pro Ile Met Asp Thr Asp Gly Ser Tyr Phe Val Tyr Ser
                165                 170                 175

Lys Leu Asn Val Gln Lys Ser Asn Trp Glu Ala Gly Asn Thr Phe Thr
            180                 185                 190

Cys Ser Val Leu His Glu Gly Leu His Asn His His Thr Glu Lys Ser
        195                 200                 205

Leu Ser His Ser Pro Gly Lys
    210                 215

<210> SEQ ID NO 6
<211> LENGTH: 218
<212> TYPE: PRT
<213> ORGANISM: Mus sp.

<400> SEQUENCE: 6

Pro Ala Pro Asn Leu Leu Gly Gly Pro Ser Val Phe Ile Phe Pro Pro
1               5                   10                  15

Lys Ile Lys Asp Val Leu Met Ile Ser Leu Ser Pro Ile Val Thr Cys
            20                  25                  30

Val Val Val Asp Val Ser Glu Asp Asp Pro Asp Val Gln Ile Ser Trp
        35                  40                  45

Phe Val Asn Asn Val Glu Val His Thr Ala Gln Thr Gln Thr His Arg
    50                  55                  60

Glu Asp Tyr Asn Ser Thr Leu Arg Val Val Ser Ala Leu Pro Ile Gln
65                  70                  75                  80

His Gln Asp Trp Met Ser Gly Lys Glu Phe Lys Cys Lys Val Asn Asn
                85                  90                  95

Lys Asp Leu Pro Ala Pro Ile Glu Arg Thr Ile Ser Lys Pro Lys Gly

```
                    100                 105                 110
Ser Val Arg Ala Pro Gln Val Tyr Val Leu Pro Pro Glu Glu Glu
            115                 120                 125

Met Thr Lys Lys Gln Val Thr Leu Thr Cys Met Val Thr Asp Phe Met
130                 135                 140

Pro Glu Asp Ile Tyr Val Glu Trp Thr Asn Asn Gly Lys Thr Glu Leu
145                 150                 155                 160

Asn Tyr Lys Asn Thr Glu Pro Val Leu Asp Ser Asp Gly Ser Tyr Phe
                165                 170                 175

Met Tyr Ser Lys Leu Arg Val Glu Lys Lys Asn Trp Val Glu Arg Asn
            180                 185                 190

Ser Tyr Ser Cys Ser Val Val His Glu Gly Leu His Asn His His Thr
            195                 200                 205

Thr Lys Ser Phe Ser Arg Thr Pro Gly Lys
            210                 215

<210> SEQ ID NO 7
<211> LENGTH: 218
<212> TYPE: PRT
<213> ORGANISM: Mus sp.

<400> SEQUENCE: 7

Pro Ala Pro Asn Leu Glu Gly Gly Pro Ser Val Phe Ile Phe Pro Pro
1               5                   10                  15

Asn Ile Lys Asp Val Leu Met Ile Ser Leu Thr Pro Lys Val Thr Cys
            20                  25                  30

Val Val Val Asp Val Ser Glu Asp Asp Pro Asp Val Gln Ile Ser Trp
        35                  40                  45

Phe Val Asn Asn Val Glu Val His Thr Ala Gln Thr Gln Thr His Arg
    50                  55                  60

Glu Asp Tyr Asn Ser Thr Ile Arg Val Val Ser His Leu Pro Ile Gln
65                  70                  75                  80

His Gln Asp Trp Met Ser Gly Lys Glu Phe Lys Cys Lys Val Asn Asn
                85                  90                  95

Lys Asp Leu Pro Ser Pro Ile Glu Arg Thr Ile Ser Lys Pro Lys Gly
            100                 105                 110

Leu Val Arg Ala Pro Gln Val Tyr Thr Leu Pro Pro Ala Glu Gln
            115                 120                 125

Leu Ser Arg Lys Asp Val Ser Leu Thr Cys Leu Val Val Gly Phe Asn
            130                 135                 140

Pro Gly Asp Ile Ser Val Glu Trp Thr Ser Asn Gly His Thr Glu Glu
145                 150                 155                 160

Asn Tyr Lys Asp Thr Ala Pro Val Leu Asp Ser Asp Gly Ser Tyr Phe
                165                 170                 175

Ile Tyr Ser Lys Leu Asn Met Lys Thr Ser Lys Trp Glu Lys Thr Asp
            180                 185                 190

Ser Phe Ser Cys Asn Val Arg His Glu Gly Leu Lys Asn Tyr Tyr Leu
            195                 200                 205

Lys Lys Thr Ile Ser Arg Ser Pro Gly Lys
            210                 215

<210> SEQ ID NO 8
<211> LENGTH: 218
<212> TYPE: PRT
<213> ORGANISM: Mus sp.
```

<400> SEQUENCE: 8

```
Pro Pro Gly Asn Ile Leu Gly Gly Pro Ser Val Phe Ile Phe Pro Pro
1               5                   10                  15
Lys Pro Lys Asp Ala Leu Met Ile Ser Leu Thr Pro Lys Val Thr Cys
            20                  25                  30
Val Val Val Asp Val Ser Glu Asp Asp Pro Asp Val His Val Ser Trp
        35                  40                  45
Phe Val Asp Asn Lys Glu Val His Thr Ala Trp Thr Gln Pro Arg Glu
50                  55                  60
Ala Gln Tyr Asn Ser Thr Phe Arg Val Val Ser Ala Leu Pro Ile Gln
65                  70                  75                  80
His Gln Asp Trp Met Arg Gly Lys Glu Phe Lys Cys Lys Val Asn Asn
                85                  90                  95
Lys Ala Leu Pro Ala Pro Ile Glu Arg Thr Ile Ser Lys Pro Lys Gly
            100                 105                 110
Arg Ala Gln Thr Pro Gln Val Tyr Thr Ile Pro Pro Arg Glu Gln
        115                 120                 125
Met Ser Lys Lys Lys Val Ser Leu Thr Cys Leu Val Thr Asn Phe Phe
130                 135                 140
Ser Glu Ala Ile Ser Val Glu Trp Glu Arg Asn Gly Glu Leu Glu Gln
145                 150                 155                 160
Asp Tyr Lys Asn Thr Pro Pro Ile Leu Asp Ser Asp Gly Thr Tyr Phe
                165                 170                 175
Leu Tyr Ser Lys Leu Thr Val Asp Thr Asp Ser Trp Leu Gln Gly Glu
            180                 185                 190
Ile Phe Thr Cys Ser Val Val His Glu Ala Leu His Asn His His Thr
        195                 200                 205
Gln Lys Asn Leu Ser Arg Ser Pro Gly Lys
210                 215
```

<210> SEQ ID NO 9
<211> LENGTH: 110
<212> TYPE: PRT
<213> ORGANISM: Homo sapiens

<400> SEQUENCE: 9

```
Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys
            100                 105                 110
```

<210> SEQ ID NO 10
<211> LENGTH: 107
<212> TYPE: PRT
<213> ORGANISM: Homo sapiens

```
<400> SEQUENCE: 10

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 11
<211> LENGTH: 330
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Tyr Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 12
<211> LENGTH: 329
<212> TYPE: PRT
<213> ORGANISM: Homo sapiens

<400> SEQUENCE: 12

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Asn Val
    290                 295                 300
```

-continued

```
Phe Ser Cys Ser Val Met His Glu Ala Leu His Asn His Tyr Thr Gln
305                 310                 315                 320

Lys Ser Leu Ser Leu Ser Pro Gly Lys
            325
```

<210> SEQ ID NO 13
<211> LENGTH: 97
<212> TYPE: PRT
<213> ORGANISM: Artificial Sequence
<220> FEATURE:
<223> OTHER INFORMATION: Synthetic Construct

<400> SEQUENCE: 13

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Pro Tyr Ile
            20                  25                  30

His Trp Tyr Gln Gln Lys Pro Gly Gln Ala Pro Arg Leu Leu Ile Tyr
        35                  40                  45

Ala Thr Ser Ala Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Leu Ser Asn Pro Pro Thr
                85                  90                  95

Phe
```

<210> SEQ ID NO 14
<211> LENGTH: 111
<212> TYPE: PRT
<213> ORGANISM: Artifical Sequence

<400> SEQUENCE: 14

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Arg Thr Phe Thr Ser Tyr
            20                  25                  30

Asn Met His Trp Val Arg Gln Met Pro Gly Lys Gly Leu Glu Trp Met
        35                  40                  45

Gly Ala Ile Tyr Pro Leu Thr Gly Asp Thr Ser Tyr Asn Gln Lys Ser
    50                  55                  60

Lys Leu Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Thr Tyr Val Gly Gly Asp Trp Gln Phe Asp Val Trp
            100                 105                 110
```

<210> SEQ ID NO 15
<211> LENGTH: 97
<212> TYPE: PRT
<213> ORGANISM: Artificial Sequence
<220> FEATURE:
<223> OTHER INFORMATION: Synthetic Construct

<400> SEQUENCE: 15

```
Gln Ile Val Leu Ser Gln Ser Pro Ala Ile Leu Ser Ala Ser Pro Gly
1               5                   10                  15
```

```
Glu Lys Val Thr Met Thr Cys Arg Ala Ser Ser Val Ser Tyr Ile
             20                  25                  30

His Trp Phe Gln Gln Lys Pro Gly Ser Ser Pro Lys Pro Trp Ile Tyr
         35                  40                  45

Ala Thr Ser Asn Leu Ala Ser Gly Val Pro Val Arg Phe Ser Gly Ser
     50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe
```

<210> SEQ ID NO 16
<211> LENGTH: 111
<212> TYPE: PRT
<213> ORGANISM: Artificial Sequence
<220> FEATURE:
<223> OTHER INFORMATION: Synthetic Construct

<400> SEQUENCE: 16

```
Gln Val Gln Leu Gln Gln Pro Gly Ala Glu Leu Val Lys Ala Gly Ala
 1               5                  10                  15

Ser Val Lys Met Ser Cys Lys Ala Ser Gly Tyr Thr Phe Thr Ser Tyr
             20                  25                  30

Asn Met His Trp Val Lys Gln Thr Pro Gly Arg Gly Leu Glu Trp Ile
         35                  40                  45

Gly Ala Ile Tyr Pro Gly Asn Gly Asp Thr Ser Tyr Asn Gln Lys Phe
     50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Thr Tyr Tyr Gly Gly Asp Trp Tyr Phe Asn Val Trp
                100                 105                 110
```

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

```
Arg Ala Ser Ser Ser Val Pro Tyr Ile His
 1               5                  10
```

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

```
Ala Thr Ser Ala Leu Ala Ser
 1               5
```

<210> SEQ ID NO 19
<211> LENGTH: 9
<212> TYPE: PRT
<213> ORGANISM: Artificial Sequence

```
<220> FEATURE:
<223> OTHER INFORMATION: Synthetic Construct

<400> SEQUENCE: 19

Gln Gln Trp Leu Ser Asn Pro Pro Thr
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Gly Arg Thr Phe Thr Ser Tyr Asn Met His
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

Ala Ile Tyr Pro Leu Thr Gly Asp Thr Ser Tyr Asn Gln Lys Ser Lys
1               5                   10                  15

Leu

<210> SEQ ID NO 22
<211> LENGTH: 12
<212> TYPE: PRT
<213> ORGANISM: Artificial Sequence
<220> FEATURE:
<223> OTHER INFORMATION: Synthetic Construct

<400> SEQUENCE: 22

Ser Thr Tyr Val Gly Gly Asp Trp Gln Phe Asp Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic Construct

<400> SEQUENCE: 23

Arg Ala Ser Ser Ser Val Ser Tyr Ile His
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct

<400> SEQUENCE: 24

Ala Thr Ser Asn Leu Ala Ser
1               5

<210> SEQ ID NO 25
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 25

Gln Gln Trp Thr Ser Asn Pro Pro Thr
1               5

<210> SEQ ID NO 26
<211> LENGTH: 10
<212> TYPE: PRT
<213> ORGANISM: Artificial
<220> FEATURE:
<223> OTHER INFORMATION: Synthetic Construct

<400> SEQUENCE: 26

Gly Tyr Thr Phe Thr Ser Tyr Asn Met His
1               5                   10

<210> SEQ ID NO 27
<211> LENGTH: 17
<212> TYPE: PRT
<213> ORGANISM: Artificial Sequence
<220> FEATURE:
<223> OTHER INFORMATION: Synthetic Construct

<400> SEQUENCE: 27

Ala Ile Tyr Pro Gly Asn Gly Asp Thr Ser Tyr Asn Gln Lys Phe Lys
1               5                   10                  15

Gly

<210> SEQ ID NO 28
<211> LENGTH: 12
<212> TYPE: PRT
<213> ORGANISM: Artificial Sequence
<220> FEATURE:
<223> OTHER INFORMATION: Synthetic Construct

<400> SEQUENCE: 28

Ser Thr Tyr Tyr Gly Gly Asp Trp Tyr Phe Asn Val
1               5                   10

<210> SEQ ID NO 29
<211> LENGTH: 213
<212> TYPE: PRT
<213> ORGANISM: Artificial Sequence
<220> FEATURE:
<223> OTHER INFORMATION: Synthetic Construct

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Pro Tyr Ile
            20                  25                  30

His Trp Tyr Gln Gln Lys Pro Gly Gln Ala Pro Arg Leu Leu Ile Tyr
        35                  40                  45

Ala Thr Ser Ala Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Leu Ser Asn Pro Pro Thr
                85                  90                  95

Phe Gly Gln Gly Thr Lys Leu Glu Ile Lys Arg Thr Val Ala Ala Pro
```

-continued

```
                100                 105                 110
Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 30
<211> LENGTH: 642
<212> TYPE: DNA
<213> ORGANISM: Artificial Sequence
<220> FEATURE:
<223> OTHER INFORMATION: Synthetic Construct

<400> SEQUENCE: 30
gaaattgtgt tgacgcagtc tccaggcacc ctgtctttgt ctccagggga aagagccacc      60
ctctcctgca gggccagctc aagtgtaccg tacatccact ggtaccagca gaaacctggc     120
caggctccca ggctcctcat ctatgccaca tccgctctgg cttctggcat cccagacagg     180
ttcagtggca gtgggtctgg gacagacttc actctcacca tcagcagact ggagcctgaa     240
gattttgcag tgtattactg tcagcagtgg ctgagtaacc cacccacttt tggccagggg     300
accaagctgg agatcaaacg aactgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtt ag                      642

<210> SEQ ID NO 31
<211> LENGTH: 451
<212> TYPE: PRT
<213> ORGANISM: Artificial Sequence
<220> FEATURE:
<223> OTHER INFORMATION: Synthetic Construct

<400> SEQUENCE: 31

Glu Val Gln Leu Val Gln Ser Gly Ala Glu Val Lys Lys Pro Gly Glu
1               5                   10                  15

Ser Leu Lys Ile Ser Cys Lys Gly Ser Gly Arg Thr Phe Thr Ser Tyr
            20                  25                  30

Asn Met His Trp Val Arg Gln Met Pro Gly Lys Gly Leu Glu Trp Met
        35                  40                  45

Gly Ala Ile Tyr Pro Leu Thr Gly Asp Thr Ser Tyr Asn Gln Lys Ser
    50                  55                  60

Lys Leu Gln Val Thr Ile Ser Ala Asp Lys Ser Ile Ser Thr Ala Tyr
65                  70                  75                  80
```

-continued

```
Leu Gln Trp Ser Ser Leu Lys Ala Ser Asp Thr Ala Met Tyr Tyr Cys
                 85                  90                  95

Ala Arg Ser Thr Tyr Val Gly Gly Asp Trp Gln Phe Asp Val Trp Gly
            100                 105                 110

Lys Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Ile Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Gln Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 32
<211> LENGTH: 1356
<212> TYPE: DNA
<213> ORGANISM: Artificial Sequence
<220> FEATURE:
```

<223> OTHER INFORMATION: Synthetic Construct

<400> SEQUENCE: 32

```
gaggtgcagc tggtgcagtc tggagcagag gtgaaaaagc ccggggagtc tctgaagatc    60
tcctgtaagg gttctggccg tacatttacc agttacaata tgcactgggt gcgccagatg   120
cccgggaaag gcctggagtg gatgggggct atttatccct tgacgggtga tacttcctac   180
aatcagaagt cgaaactcca ggtcaccatc tcagccgaca gtccatcagc accgcctac    240
ctgcagtgga gcagcctgaa ggcctcggac accgccatgt attactgtgc gagatcgact   300
tacgtgggcg gtgactggca gttcgatgtc tggggcaagg gaccacggt caccgtctcc    360
tcagcctcca ccaagggccc atcggtcttc cccctggcac cctcctccaa gagcacctct   420
gggggcacag cggccctggg ctgcctggtc aaggactact ccccgaacc ggtgacggtg    480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gaaggttgag   660
cccaaatctt gtgacaaaac tcacacatgc ccaccgtgcc cagcacctga actcctgggg   720
ggaccgtcag tcttcctctt ccccccaaaa atcaaggaca ccctcatgat ctcccggacc   780
cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacgt accgtgtggt cagcgtcctc accgtcctgc accaggactg gctgaatggc   960
aaggagtaca agtgcaaggt ctccaacaaa gccctcccag cccccatcga gaaaaccatc  1020
tccaaacaga agggcagcc ccgagaacca caggtgtaca ccctgccccc atcccgggac   1080
gagctgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tatagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaatga                            1356
```

<210> SEQ ID NO 33
<211> LENGTH: 451
<212> TYPE: PRT
<213> ORGANISM: Artificial Sequence
<220> FEATURE:
<223> OTHER INFORMATION: Synthetic Construct

<400> SEQUENCE: 33

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Arg Thr Phe Thr Ser Tyr
            20                  25                  30

Asn Met His Trp Val Arg Gln Met Pro Gly Lys Gly Leu Glu Trp Met
        35                  40                  45

Gly Ala Ile Tyr Pro Leu Thr Gly Asp Thr Ser Tyr Asn Gln Lys Ser
    50                  55                  60

Lys Leu Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Thr Tyr Val Gly Gly Asp Trp Gln Phe Asp Val Trp Gly
```

-continued

```
                     100                 105                 110
Lys Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Ile Lys Asp Thr Leu Met
            245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Asp Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
    435                 440                 445

Pro Gly Lys
    450
```

<210> SEQ ID NO 34
<211> LENGTH: 1356
<212> TYPE: DNA
<213> ORGANISM: Artificial
<220> FEATURE:
<223> OTHER INFORMATION: Synthetic Construct

<400> SEQUENCE: 34
gaggtgcagc tggtgcagtc tggagcagag gtgaaaaagc ccggggagtc tctgaagatc    60

```
tcctgtaagg gttctggccg tacatttacc agttacaata tgcactgggt gcgccagatg    120
cccgggaaag gcctggagtg gatgggggct atttatccct tgacgggtga tacttcctac    180
aatcagaagt cgaaactcca ggtcaccatc tcagccgaca agtccatcag caccgcctac    240
ctgcagtgga gcagcctgaa ggcctcggac accgccatgt attactgtgc gagatcgact    300
tacgtgggcg gtgactggca gttcgatgtc tggggcaagg gaccacggt caccgtctcc    360 tcagcctcca ccaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaggttgag    660
cccaaatctt gtgacaaaac tcacacatgc ccaccgtgcc cagcacctga actcctgggg    720
ggaccgtcag tcttcctctt ccccccaaaa atcaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc    1020
tccaaagaca aagggcagcc ccgagaacca caggtgtaca ccctgccccc atcccgggac    1080
gagctgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tatagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaatga                              1356
```

<210> SEQ ID NO 35
<211> LENGTH: 451
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Val Gln Ser Gly Ala Glu Val Lys Lys Pro Gly Glu
1               5                   10                  15

Ser Leu Lys Ile Ser Cys Lys Gly Ser Gly Arg Thr Phe Thr Ser Tyr
            20                  25                  30

Asn Met His Trp Val Arg Gln Met Pro Gly Lys Gly Leu Glu Trp Met
        35                  40                  45

Gly Ala Ile Tyr Pro Leu Thr Gly Asp Thr Ser Tyr Asn Gln Lys Ser
    50                  55                  60

Lys Leu Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Thr Tyr Val Gly Gly Asp Trp Gln Phe Asp Val Trp Gly
            100                 105                 110

Lys Gly Thr Thr Val Thr Val Ser Ser Ala Ser Thr Lys Gly Pro Ser
        115                 120                 125

-continued

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Asp Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 36
<211> LENGTH: 1356
<212> TYPE: DNA
<213> ORGANISM: Artificial Sequence
<220> FEATURE:
<223> OTHER INFORMATION: Synthetic Construct

<400> SEQUENCE: 36
gaggtgcagc tggtgcagtc tggagcagag gtgaaaaagc cggggagtc tctgaagatc      60 tcctgtaagg gttctggccg tacatttacc agttacaata tgcactgggt gcgccagatg     120
cccgggaaag gcctggagtg gatgggggct atttatcct tgacgggtga tacttcctac     180
```

-continued

```
aatcagaagt cgaaactcca ggtcaccatc tcagccgaca agtccatcag caccgcctac    240
ctgcagtgga gcagcctgaa ggcctcggac accgccatgt attactgtgc gagatcgact    300
tacgtgggcg gtgactggca gttcgatgtc tggggcaagg ggaccacggt caccgtctcc    360
tcagcctcca ccaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaggttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggac   1080
gagctgacca agaaccaggt cagcctgacc tgcctggtca aaggcttcta tcccagcgac   1140
atcgacgtgg agtgggagag caatgggcag ccggagaaca actacaagac cacgcctccc   1200
gtgctggact ccgacggctc cttcttcctc tatagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaatga                             1356
```

VARIANT FC REGIONS

This application claims the benefit of U.S. Provision Applications with Serial Nos.; and PCT Application Ser. Nos.: 60/598,855 filed Aug. 4, 2004; 60/602,953 filed Aug. 19, 2004; 60/604,339 filed Aug. 25, 2004; 60/609,101 filed Sep. 10, 2004; 60/638,442 filed Dec. 23, 2004; 60/643,718 filed Jan. 13, 2005; International Application Number: PCT/US2005/025276 filed Jul. 18, 2005; all of which are expressly incorporated herein by reference in their entirely.

FIELD OF THE INVENTION

The present invention relates to polypeptides comprising a novel, variant Fc region. Specifically, a novel, variant Fc region of the present invention comprises at least one amino acid substitution described herein that confers an altered effector function or altered serum half-life upon an immunoglobulin comprising the variant Fc region as compared to the parent immunoglobulin lacking that amino acid substitution. Furthermore, the invention provides a method for altering an effector function of a monoclonal antibody or extending the serum half-life of a polypeptide to which a variant Fc region of the invention is operably attached. Therapeutic uses of polypeptides, proteins, particularly monoclonal antibodies, comprising a variant Fc region of the invention are disclosed.

BACKGROUND OF THE INVENTION

There are at least seventeen monoclonal antibodies currently approved in the United States for use as human therapeutics. Additionally, there are several hundred monoclonal antibodies in clinical trials and thousands in pre-clinical testing for treatment of various diseases or disorders including, e.g., transplant rejection, cancer, inflammatory diseases, sepsis, nephritis, Alzheimer's disease, allergies, diabetes, autoimmune diseases, arthritis, multiple sclerosis, and infectious diseases. The field of therapeutic monoclonal antibodies is positioned for rapid growth in the coming years. After vaccines, antibodies (or immunoglobulins, "Ig") constitute the second most common type of biopharmaceutical agent being tested clinically (Stockwin, L. H. et al. *Biochemical Society Transactions*, 31:433-436, 2003).

Genetic engineering has contributed substantially to growth of the field of therapeutic monoclonal antibodies. The effectiveness of a potential therapeutic monoclonal antibody will often vary with modest changes to the protein sequence of the antibody. A single amino acid change in the variable region of a monoclonal antibody has the potential to alter the affinity with which the antibody binds the antigenic epitope, as well as antibody properties such as $K_{on}$ rate or $K_{off}$ rate. Such amino acid changes may determine the success or failure of a monoclonal antibody as a therapeutic. Similarly, modest changes in the amino acid sequence of the Fc region of a monoclonal antibody may yield profound changes in the antibody's effector function properties or the half-life of a protein to which the Fc region is operably linked.

The Fc region of an antibody (i.e., the carboxy-terminal ends of the heavy chains of an antibody spanning domains CH2, CH3 and a portion of the hinge region (see FIG. 1)), is limited in variability and is involved in effecting the physiological roles played by the antibody. The effector functions attributable to the Fc region of an antibody vary with the class and subclass of antibody and include (i) binding of the antibody via the Fc region to a specific Fc receptor ("FcR") on a cell which triggers various biological responses including, e.g., phagocytosis and destruction of antibody-coated particles, clearance of immune complexes, release of inflammatory mediators, placental transfer of the antibody and control of immunoglobulin production, (ii) complement-dependent cytotoxicity ("CDC") in which the Fc region binds the C1q component of complement and thereby initiates the classical pathway of complement activation which leads to lysis of the target, (iii) antibody dependent cell-mediated cytotoxicity ("ADCC") in which certain human immune system cells, e.g., phagocytes and NK cells, via an Fcγ receptor, bind to the Fc region of an antibody via specific antibody-binding receptors on the immune cells and subsequently signal destruction of the entity to which the antibody is bound, and, (iv) binding to mast cells, basophils, and eosinophils. The affinity with which an Fc region can bind a particular FcR (e.g., FcRn), or the level with which an Fc region can mediate CDC or ADCC activity are important factors for determining the efficacy and half-life of therapeutic proteins, particularly monoclonal antibodies.

Particularized modification of amino acids in the Fc region of human IgG is an active area of study yielding structure-function relationship information relevant to development of therapeutic proteins, particularly monoclonal antibodies (see, e.g., U.S. Pat. No. 6,165,745 and PCT Publication No. WO2004/035752 regarding alteration of serum half-life of a polypeptide operably linked to an Fc region and U.S. Pat. No. 6,737,056 and PCT Publication No. WO2004/029207 regarding alteration of an effector function of a monoclonal antibody comprising a modified Fc region).

The development of novel therapeutic proteins, particularly monoclonal antibodies, would benefit from the ability to rationally design an Fc region with particular amino acid modifications that confer a desired beneficial property upon the antibody of interest. All monoclonal antibodies would not be expected to be improved as a therapeutic due to the same particular amino acid modification in the Fc region. A therapeutic monoclonal antibody that binds one target antigen may benefit from an increase in a particular effector function while a different therapeutic monoclonal antibody that binds a different target antigen may benefit from an increase in a different effector function, or even a decrease. One therapeutic monoclonal antibody may benefit from the ability to bind a particular Fc receptor with greater affinity while another antibody may be improved as a therapeutic by binding that Fc receptor at a lower affinity and therefore being cleared from the body at a faster rate. Furthermore, a particular Fc region amino acid modification or substitution and resulting effect that would benefit a therapeutic antibody may depend upon the antigenic target to which the antibody binds and/or the disease or disorder to be ameliorated by the antibody.

Methods and compositions that alter particular effector functions associated with the Fc region of an antibody are necessary to improve the properties of existing therapeutic antibodies as well as to generate novel therapeutic antibodies with desired properties. Monoclonal antibodies with variant Fc regions may be used to treat various diseases or disorders including, e.g., inflammatory disorders, cancer, autoimmune disorders, cell-signalling disorders and infectious diseases. Additionally, methods and compositions that alter the serum half-life of a therapeutic protein, either increasing the half-life and thereby allowing for fewer doses or decreasing the half-life and thereby allowing for more rapid clearance from the body, would benefit the generation of therapeutic antibodies as well as other therapeutic proteins.

What is needed in order to improve the efficacy of a therapeutic protein, particularly a monoclonal antibody, are variant Fc regions with improved properties.

SUMMARY OF THE INVENTION

The present invention provides variant Fc regions, i.e., Fc regions comprising an amino acid substitution described herein (e.g., see Table 1), that confer beneficial properties upon polypeptides comprising said variant Fc regions.

Fc positions of a parent Fc region at which any amino acid substitution may be made to generate a variant Fc region of the invention include positions 279, 341, 343 and 373 of the Fc region, wherein the numbering of the residues, i.e., their position number, in the Fc region is that of the EU index as in Kabat (see FIG. 2 herein). The present invention provides variant Fc regions comprising an amino acid substitution at position 279, 341, 343 or 373 of a parent Fc region, or any combination thereof. The parent Fc region may optionally have non-native amino acid residues at positions other than 279, 341, 343 and 373. The native amino acid residues at these positions for human IgG are valine (279), glycine (341), proline (343) and tyrosine (373).

In preferred embodiments throughout the present invention, the amino acid residue substituted for that present in the parent Fc region is a naturally occurring amino acid residue. Unless otherwise stated, the parent Fc region may be a native or non-native Fc region, preferably of human origin or substantially of human origin. The amino acid sequence of the parent Fc region is preferably that as shown in SEQ ID NOs: 1, 2, 3 or 4. Preferably the parent Fc region has a native amino acid residue present at the position which is to be substituted to generate a variant Fc region of the invention. Furthermore, throughout, it is understood that a variant Fc region is a parent Fc region modified to comprise at least one amino acid substitution as described herein. Additionally, it is understood that a parent Fc region may be a full-length Fc or a portion thereof comprising the amino acid residue to be substituted to generate the variant Fc region.

The present invention further provides polypeptides, preferably monoclonal antibodies, comprising a variant Fc region (or a functional fragment thereof) comprising at least one amino acid substitution at position 279, 341, 343 or 373 as compared to the parent Fc region. The variant Fc region comprising at least one amino acid substitution at Fc position 279, 341, 343 or 373 may further comprise at least one additional amino acid substitution in the Fc region as compared to the amino acid residue present in the native Fc region of the same type as the variant Fc region.

In one embodiment, a variant Fc region (i.e., a variant of a parent Fc region) comprises at least 1, 2, 3 or more amino acid substitutions selected from the following: 235G, 235R, 236F, 236R, 236Y, 237K, 237N, 237R, 238E, 238G, 238H, 238I, 238L, 238V, 238W, 238Y, 244L, 245R, 247A, 247D, 247E, 247F, 247M, 247N, 247Q, 247R, 247S, 247T, 247W, 247Y, 248F, 248P, 248Q, 248W, 249L, 249M, 249N, 249P, 249Y, 251H, 251I, 251W, 254D, 254E, 254F, 254G, 254H, 254I, 254K, 254L, 254M, 254N, 254P, 254Q, 254R, 254V, 254W, 254Y, 255K, 255N, 256H, 256I, 256K, 256L, 256V, 256W, 256Y, 257A, 257I, 257M, 257N, 257S, 258D, 260S, 262L, 264S, 265K, 265S, 267H, 267I, 267K, 268K, 269N, 269Q, 271T, 272H, 272K, 272L, 272R, 279A, 279D, 279F, 279G, 279H, 279I, 279K, 279L, 279M, 279N, 279Q, 279R, 279S, 279T, 279W, 279Y, 280T, 283F, 283G, 283H, 283I, 283K, 283L, 283M, 283R, 283T, 283W, 283Y, 285N, 286F, 288N, 288P, 292E, 292F, 292G, 292I, 293S, 293V, 301W, 304E, 307E, 307M, 312P, 315F, 315K, 315L, 315P, 315R, 316F, 316K, 317P, 317T, 318N, 318P, 318T, 332F, 332G, 332L, 332M, 332S, 332V, 332W, 339D, 339E, 339F, 339G, 339H, 339I, 339K, 339L, 339M, 339N, 339Q, 339R, 339S, 339W, 339Y, 341D, 341E, 341F, 341H, 341I, 341K, 341L, 341M, 341N, 341P, 341Q, 341R, 341S, 341T, 341V, 341W, 341Y, 343A, 343D, 343E, 343F, 343G, 343H, 343I, 343K, 343L, 343M, 343N, 343Q, 343R, 343S, 343T, 343V, 343W, 343Y, 373D, 373E, 373F, 373G, 373H, 373I, 373K, 373L, 373M, 373N, 373Q, 373R, 373S, 373T, 373V, 373W, 375R, 376E, 376F, 376G, 376H, 376I, 376L, 376M, 376N, 376P, 376Q, 376R, 376S, 376T, 376V, 376W, 376Y, 377G, 377K, 377P, 378N, 379N, 379Q, 379S, 379T, 380D, 380N, 380S, 380T, 382D, 382F, 382H, 382I, 382K, 382L, 382M, 382N, 382P, 382Q, 382R, 382S, 382T, 382V, 382W, 382Y, 385E, 385P, 386K, 423N, 424H, 424M, 424V, 426D, 426L, 427N, 429A, 429F, 429M, 430A, 430D, 430F, 430G, 430H, 430I, 430K, 430L, 430M, 430N, 430P, 430Q, 430R, 430S, 430T, 430V, 430W, 430Y, 431H, 431K, 431P, 432R, 432S, 438G, 438K, 438L, 438T, 438W, 439E, 439H, 439Q, 440D, 440E, 440F, 440G, 440H, 440I, 440K, 440L, 440M, 440Q, 440T, 440V or 442K.

In a preferred embodiment, a variant Fc region comprises at least 1, 2, 3 or more amino acid substitutions selected from the following: 235G, 236F, 236R, 236Y, 237K, 237N, 237R, 238E, 238G, 238H, 238I, 238L, 238V, 238W, 238Y, 245R, 247A, 247D, 247E, 247F, 247M, 247N, 247Q, 247R, 247T, 247W, 247Y, 248F, 248P, 248Q, 248W, 249L, 249M, 249N, 249P, 249Y, 251H, 251I, 251W, 254D, 254E, 254F, 254G, 254H, 254I, 254K, 254L, 254M, 254N, 254P, 254Q, 254R, 254V, 254W, 254Y, 255K, 255N, 256H, 256I, 256K, 256L, 256W, 257A, 257I, 257M, 257N, 257S, 258D, 260S, 262L, 264S, 265K, 265S, 267H, 267I, 267K, 268K, 269N, 269Q, 271T, 272H, 272K, 272R, 279A, 279D, 279G, 279H, 279N, 279Q, 279S, 279T, 279W, 279Y, 280T, 283F, 283H, 283K, 283M, 283R, 283W, 285N, 286F, 288N, 288P, 292E, 292G, 292I, 301W, 304E, 307E, 307M, 312P, 315F, 315L, 315P, 316F, 317P, 317T, 318N, 318P, 318T, 332L, 332M, 332R, 332S, 332W, 339D, 339F, 339I, 339K, 339M, 339N, 339Q, 339R, 339S, 339W, 339Y, 341D, 341E, 341F, 341H, 341I, 341K, 341L, 341M, 341N, 341P, 341Q, 341R, 341S, 341T, 341V, 341W, 341Y, 343D, 343E, 343G, 343H, 343K, 343N, 343Q, 343R, 343S, 343T, 343W, 343Y, 373D, 373E, 373G, 373H, 373I, 373K, 373L, 373M, 373Q, 373R, 373S, 373T, 373W, 375R, 376G, 376N, 376P, 376Q, 376R, 376S, 376T, 376V, 376W, 376Y, 377G, 377K, 377P, 378D, 378N, 379N, 379Q, 379T, 380N, 380S, 380T, 382D, 382F, 382I, 382K, 382L, 382Q, 382R, 382S, 382T, 382V, 382W, 382Y, 385E, 386K, 423N, 424H, 424M, 424V, 426D, 426L, 427N, 429A, 429F, 429M, 430A, 430D, 430F, 430G, 430H, 430I, 430K, 430L, 430M, 430N, 430P, 430Q, 430R, 430S, 430T, 430V, 430W, 430Y, 431H, 431K, 431P, 432R, 432S, 438K, 438L, 438T, 438W, 439E, 440D, 440I or 440L.

The variant Fc regions of the present invention are preferably characterized using one of more of the experimental methods described herein. Such variant Fc regions confer an altered effector function or altered serum half-life upon a monoclonal antibody that comprises the variant Fc region or an altered serum half-life upon a polypeptide to which the variant Fc region is operably attached.

Preferably the parent Fc region of a variant Fc region of the invention is a native or germline-encoded Fc region of human origin selected from the group consisting of IgG, IgA, IgE, IgM and IgD or a polymorphic variant thereof, or a functional fragment thereof. Preferably the parent Fc region is an IgG Fc region, and more preferably, an IgG1, IgG3, or IgG4 Fc region. The parent Fc region may optionally comprise one or more additional amino acid substitution(s) as compared to the native Fc region, other than those described herein (i.e., those substitutions listed in Table 1), particularly one or more amino acid substitutions known in the art or as described in U.S. Pat. Nos. 6,165,745 or 6,737,056; or PCT Publication Nos. WO2004/035752 or WO2004/029207 (all of which are incorporated herein in their entirety); such amino acid substitution(s), if present in the parent Fc region, would then also be present in the variant Fc region of the invention and in a polypeptide comprising a variant Fc region of the invention, unless it was at a position subsequently substituted to generate the variant Fc region.

The invention provides a polypeptide, preferably a monoclonal antibody, comprising a variant Fc region of the invention, or a functional fragment thereof. In a preferred embodiment, a monoclonal antibody comprising a variant Fc region of the invention is a chimeric antibody. In a more preferred embodiment, a monoclonal antibody comprising a variant Fc region of the invention is a humanized antibody or a human antibody in which framework sequence and constant region sequence present in the antibody is substantially of human origin. The chimeric, humanized or human antibody is preferably a full-length antibody or a single chain antibody. When a monoclonal antibody comprising a variant Fc region of the invention is to be used as a human therapeutic, the Fc region is preferably substantially of human origin.

Preferably a polypeptide comprising, or operably attached to, a variant Fc region of the invention (i.e., "variant polypeptide") has at least one amino acid substitution in the variant Fc region as compared to the parent Fc region, and displays an altered effector function or altered serum half-life as compared to that of the polypeptide comprising the parent Fc region of said variant Fc region, wherein the "at least one amino acid substitution in the variant Fc region" is (i) any amino acid substitution at position 279, 341, 343 or 373 of the Fc region or (ii) at least one of the following amino acid substitutions in the Fc region: 235G, 235R, 236F, 236R, 236Y, 237K, 237N, 237R, 238E, 238G, 238H, 238I, 238L, 238V, 238W, 238Y, 244L, 245R, 247A, 247D, 247E, 247F, 247M, 247N, 247Q, 247R, 247S, 247T, 247W, 247Y, 248F, 248P, 248Q, 248W, 249L, 249M, 249N, 249P, 249Y, 251H, 251I, 251W, 254D, 254E, 254F, 254G, 254H, 254I, 254K, 254L, 254M, 254N, 254P, 254Q, 254R, 254V, 254W, 254Y, 255K, 255N, 256H, 256I, 256K, 256L, 256V, 256W, 256Y, 257A, 257I, 257M, 257N, 257S, 258D, 260S, 262L, 264S, 265K, 265S, 267H, 267I, 267K, 268K, 269N, 269Q, 271T, 272H, 272K, 272L, 272R, 279A, 279D, 279F, 279G, 279H, 279I, 279K, 279L, 279M, 279N, 279Q, 279R, 279S, 279T, 279W, 279Y, 280T, 283F, 283G, 283H, 283I, 283K, 283L, 283M, 283P, 283R, 283T, 283W, 283Y, 285N, 286F, 288N, 288P, 292E, 292F, 292G, 292I, 292L, 293S, 293V, 301W, 304E, 307E, 307M, 312P, 315F, 315K, 315L, 315P, 315R, 316F, 316K, 317P, 317T, 318N, 318P, 318T, 332F, 332G, 332L, 332M, 332S, 332V, 332W, 339D, 339E, 339F, 339G, 339H, 339I, 339K, 339L, 339M, 339N, 339Q, 339R, 339S, 339W, 339Y, 341D, 341E, 341F, 341H, 341I, 341K, 341L, 341M, 341N, 341P, 341Q, 341R, 341S, 341T, 341V, 341W, 341Y, 343A, 343D, 343E, 343F, 343G, 343H, 343I, 343K, 343L, 343M, 343N, 343Q, 343R, 343S, 343T, 343V, 343W, 343Y, 373D, 373E, 373F, 373G, 373H, 373I, 373K, 373L, 373M, 373N, 373Q, 373R, 373S, 373T, 373V, 373W, 375R, 376E, 376F, 376G, 376H, 376I, 376L, 376M, 376N, 376P, 376Q, 376R, 376S, 376T, 376V, 376W, 376Y, 377G, 377K, 377P, 378N, 379N, 379Q, 379S, 379T, 380D, 380N, 380S, 380T, 382D, 382F, 382H, 382I, 382K, 382L, 382M, 382N, 382P, 382Q, 382R, 382S, 382T, 382V, 382W, 382Y, 385E, 385P, 386K, 423N, 424H, 424M, 424V, 426D, 426L, 427N, 429A, 429F, 429M, 430A, 430D, 430F, 430G, 430H, 430I, 430K, 430L, 430M, 430N, 430P, 430Q, 430R, 430S, 430T, 430V, 430W, 430Y, 431H, 431K, 431P, 432R, 432S, 438G, 438K, 438L, 438T, 438W, 439E, 439H, 439Q, 440D, 440E, 440F, 440G, 440H, 440I, 440K, 440L, 440M, 440Q, 440T, 440V or 442K, or (iii) at least two amino acid substitutions as listed in (i) or (ii) above, or (iv) at least 1, 2 or 3 amino acid substitutions as listed in (i) or (ii) above in addition to at least one Fc region amino acid substitution not listed in (i) or (ii) above. Preferably the altered effector function is an increase in ADCC, a decrease in ADCC, an increase in CDC, a decrease in CDC, an increase in C1q binding affinity, a decrease in C1q binding affinity, an increase in FcR (preferably FcRn) binding affinity or a decrease in FcR (preferably FcRn) binding affinity as compared to said polypeptide lacking the amino acid substitution in the Fc region (i.e., parent Fc region).

The invention provides a monoclonal antibody comprising a variant Fc region comprising at least one of the following amino acid substitutions in the Fc region: 247A, 247F, 247M, 247T, 247V, 247Y, 249E, 249Y, 254F, 254M, 254Y, 256A, 258D, 279A, 283A, 283I, 283K, 283M, 283R, 288N, 292A, 311A, 311D, 311N, 311T, 311V, 311Y, 315L, 318N, 318P, 318T, 318V, 332T, 332V, 339D, 339F, 339G, 339I, 339K, 339M, 339N, 339Q, 339R, 339S, 339T, 376A, 376V, 377G, 377K, 379N, 380N, 380S, 382A, 382I, 385E, 427N, 429M, 434W, 436I, 440G, 440H, 440I or 440L, [preferably 247A, 247F, 247M, 247T, 247V, 247Y, 254F, 254Y, 258D, 279A, 283M, 288N, 292A, 311D, 311N, 311T, 315L, 318N, 318P, 318T, 318V, 339D, 339I, 339K, 339M, 339N, 339Q, 339R, 339S, 376A, 376V, 377K, 379N, 380N, 382A, 440I or 440L], wherein the monoclonal antibody comprising the variant Fc region displays enhanced ADCC as compared to the monoclonal antibody comprising the parent Fc region.

The invention provides a monoclonal antibody comprising a variant Fc region comprising at least one of the following amino acid substitutions in the Fc region: 235Q, 235R, 235S, 236F, 236R, 236Y, 237E, 237K, 237N, 237R, 238E, 238G, 238H, 238I, 238L, 238V, 238W, 238Y, 247G, 247R, 249L, 249P, 250K, 250M, 250R, 251H, 251I, 251W, 252Y, 254L, 254P, 254Q, 254T, 254V, 256V, 257A, 257I, 257M, 257N, 257S, 257V, 260S, 262L, 264S, 265H, 265K, 265S, 267G, 267H, 267I, 267K, 269N, 269Q, 270A, 270G, 270K, 270M, 270N, 271T, 272H, 272K, 272L, 272N, 272R, 279D, 279F, 279N, 279L, 279W, 283D, 283F, 283G, 283H, 283L, 283W, 283Y, 285N, 288P, 292E, 292F, 292G, 292I, 293S, 293V, 301W, 304E, 307A, 307E, 307M, 311F, 311I, 311K, 311S, 312P, 314F, 314I, 314V, 314W, 315F, 315P, 316F, 317P, 327T, 328V, 329Y, 332G, 332K, 332L, 332R, 332W, 341D, 341E, 341F, 341H, 341I, 341K, 341L, 341M, 341N, 341P, 341Q, 341R, 341S, 341T, 341W, 341Y, 343A, 343D, 343E, 343F, 343G, 343H, 343L, 343M, 343N, 343Q, 343R, 343S, 343T, 343V, 343W, 343Y, 373A, 373D, 373E, 373F, 373G, 373I, 373K, 373L, 373M, 373N, 373Q, 373R, 373S, 373T, 373V, 373W, 375R, 376A, 376E, 376F, 376G, 376H, 376W, 376Y, 379Q, 382D, 382S, 430H, 430K, 430N, 430Q, 430R, 430W, 432R, 432S, 434I, 440D, 440T, 440V or 442K, [preferably 235R, 236F, 236Y, 237E, 237K, 237N, 237R, 238E, 238G, 238H, 238I, 238L, 238V, 238W, 238Y, 247R, 250K, 251H, 254T, 257I, 257M, 257N, 257S, 257V, 265H, 265K, 265S, 267G, 267H, 267I, 267K, 269N, 269Q, 270A, 270G, 270K, 270M, 270N, 271T, 272N, 272R, 288P, 292E, 301W, 304E, 316F, 317P, 327T, 328V, 329Y, 332K, 332R, 341F, 341I, 341M, 341P, 341Q, 341R, 341T, 341W, 341Y, 343W, 373A, 373E, 373S, 376A, 376W, 432R or 432S], wherein the monoclonal antibody comprising the variant Fc region displays diminished ADCC activity as compared to the monoclonal antibody comprising the parent Fc region.

The invention provides a monoclonal antibody comprising a variant Fc region comprising at least one of the following amino acid substitutions in the Fc region: 238L, 244L, 245R, 249P, 252Y, 256P, 257A, 257I, 257M, 257N, 257S, 257V, 258D, 260S, 262L, 270K, 272L, 272R, 279A, 279D, 279G, 279H, 279M, 279N, 279Q, 279R, 279S, 279T, 279W, 279Y, 283A, 283D, 283F, 283G, 283H, 283I, 283K, 283L, 283N, 283P, 283Q, 283R, 283S, 283T, 283W, 283Y, 285N, 286F, 288N, 288P, 293V, 307E, 307M, 311A, 311I, 311K, 311L, 311M, 311V, 311W, 312P, 316K, 317P, 318N, 318T, 332F, 332H, 332K, 332L, 332M, 332R, 332S, 332W, 339N, 339T, 339W, 341P, 343E, 343H, 343K, 343Q, 343R, 343T, 343Y, 375R, 376G, 376I, 376M, 376P, 376T, 376V, 377K, 378D, 378N, 380N, 380S, 380T, 382F, 382H, 382I, 382K, 382L, 382M, 382N, 382Q, 382R, 382S, 382T, 382V, 382W, 382Y, 423N, 427N, 430A, 430F, 430G, 430H, 430I, 430K, 430L, 430M, 430N, 430Q, 430R, 430S, 430T, 430V, 430Y, 431H, 431K, 434F, 434G, 434H, 434W, 434Y, 436I, 436L, 436T, 438K, 438L, 438T, 438W, 440K or 442K, [preferably 245R, 252Y, 256P, 257A, 257I, 257M, 257N, 257S, 257V, 258D, 260S, 262L, 279A, 279D, 279G, 279H, 279N, 279Q, 279S, 279T, 279W, 279Y, 283F, 283H, 283K, 283R, 285N, 286F, 307E, 307M, 311I, 311K, 311L, 311M, 312P, 318N, 318T, 332S, 339W, 343E, 343H, 343K, 343Q, 343R, 375R, 377K, 378D, 378N, 380S, 380T, 382F, 382K, 382Q, 382R, 382S, 382T, 382V, 382W, 382Y, 423N, 427N, 430A, 430F, 430H, 430I, 430L, 430M, 430N, 430Q, 430R, 430S, 430V, 430Y, 431H, 431K, 434F. 434G, 434H, 434W, 434Y, 436I, 436L, 438K, 438L or 438W] wherein the monoclonal antibody comprising the variant Fc region displays enhanced FcRn binding affinity as compared to the monoclonal antibody comprising the parent Fc region.

The invention provides a monoclonal antibody comprising a variant Fc region comprising at least one of the following amino acid substitutions in the Fc region: 235Q, 236Y, 237K, 237R, 238E, 238G, 238H, 238W, 247A, 247D, 247E, 247F, 247G, 247H, 247I, 247L, 247M, 247N, 247Q, 247R, 247S, 247W, 247Y, 248A, 248F, 248P, 248Q, 248W, 249E, 249L, 249M, 249Y, 251F, 251H, 251I, 251W, 254D, 254E, 254F, 254G, 254H, 254I, 254K, 254L, 254M, 254N, 254P, 254Q, 254R, 254T, 254V, 254W, 254Y, 255K, 255N, 256F, 256H, 256I, 256K, 256M, 256R, 256W, 256Y, 264S, 265S, 265Y, 267G, 267I, 268D, 268K, 270A, 270M, 279I, 279K, 279L, 280T, 292E, 292F, 292G, 292I, 292L, 311D, 311E, 311F, 311G, 311N, 311R, 311Y, 315F, 315K, 315P, 316F, 317T, 326W, 327T, 339E, 339G, 339L, 339R, 341D, 341E, 341F, 341I, 341K, 341L, 341M, 341N, 341Q, 341R, 341S, 341T, 341V, 341W, 341Y, 343M, 343V, 343W, 373A, 373D, 373G, 373K, 373L, 373M, 373N, 373Q, 373S, 373T, 373V, 373W, 376H, 376L, 376W, 376Y, 424M, 424V, 426D, 429A, 429F, 429M, 430D, 430W, 431P, 432R, 432S, 439Q, 440A, 440D, 440E, 440F or 440M, [preferably 237R, 247D, 247E, 247F, 247H, 247I, 247L, 247M, 247N, 247Q, 247W, 247Y, 248A, 248F, 248P, 248Q, 248W, 249L, 249M, 249Y, 251H, 251I, 251W, 254D, 254E, 254F, 254G, 254H, 254I, 254K, 254M, 254N, 254P, 254Q, 254R, 254T, 254V, 254W, 254Y, 255K, 255N, 256F, 256H, 256K, 256M, 256R, 256W, 265Y, 280T, 292G, 292I, 311D, 311E, 311G, 311N, 315F, 315P, 316T, 317T, 327T, 341D, 341E, 341F, 341I, 341L, 341Y, 343W, 373A, 373G, 373M, 373Q, 376W, 376Y, 424M, 424V, 430D, 430W, 431P or 432S], wherein the monoclonal antibody comprising the variant Fc region displays diminished FcRn binding affinity as compared to the monoclonal antibody comprising the parent Fc region.

The invention provides a monoclonal antibody comprising a variant Fc region comprising at least one of the following amino acid substitutions in the Fc region: 236Y, 244L, 247A, 247D, 247E, 247G, 247N, 247Q, 247R, 247S, 247W, 248F, 248P, 248Q, 248W, 249E, 249L, 249M, 249N, 249P, 249Y, 251F, 251H, 251I, 251W, 254A, 254F, 254K, 254L, 254M, 254R, 254Y, 255K, 256A, 256G, 256I, 256L, 256M, 256P, 256Q, 256W, 256Y, 260S, 268D, 279Q, 279S, 279W, 279Y, 280K, 280T, 283F, 283G, 283H, 283I, 283K, 283L, 283M, 283N, 283P, 283R, 283S, 283W, 292L, 307A, 307M, 311F, 311I, 311K, 311L, 311M, 311T, 311V, 311W, 311Y, 312P, 314F, 314I, 314V, 314W, 314Y, 315F, 315K, 315L, 315P, 315R, 316K, 317P, 317T, 318N, 318T, 332A, 332D, 332E, 332F, 332G, 332L, 332M, 332Q, 332S, 332T, 332V, 332W, 332Y, 339D, 339F, 339G, 339H, 339I, 339K, 339N, 339Q, 339R, 339S, 339T, 339W, 339Y, 341D, 341E, 341F, 341H, 341I, 341K, 341L, 341M, 341N, 341P, 341Q, 341R, 341S, 341T, 341V, 341W, 341Y, 343A, 343D, 343E, 343G, 343H, 343K, 343L, 343M, 343N, 343Q, 343R, 343S, 343T, 343W, 343Y, 373D, 373E, 373F, 373H, 373I, 373K, 373L, 373M, 373N, 373Q, 373R, 373T, 373V, 373W, 375R, 376A, 376F, 376G, 376H, 376L, 376N, 376P, 376Q, 376R, 376S, 376T, 376V, 377P, 379N, 379Q, 379S, 379T, 380A, 380N, 380S, 380T, 382I, 382L, 382Q, 382V, 386K, 426D, 426L, 429A, 429F, 429M, 430A, 430D, 430F, 430G, 430H, 430I, 430K, 430L, 430M, 430N, 430P, 430R, 430S, 430T, 430V, 430W, 430Y, 431H, 431P, 432R, 432S, 434W, 434Y, 438L, 438W, 440Q or 440Y, [preferably 236Y, 248F, 248P, 248Q, 248W, 249E, 249L, 249M, 249N, 249Y, 251H, 251I, 251W, 254F, 254K, 254L, 254M, 254R, 254Y, 255K, 256A, 256G, 256I, 256L, 256M, 256P, 256Q, 256W, 260S, 280K, 283W, 307M, 311F, 311I, 311K, 311L, 311M, 311T, 311V, 311W, 311Y, 314I, 314V, 314W, 314Y, 315P, 317P, 332D, 332L, 332M, 332S, 332W, 339D, 339F, 339I, 339K, 339N, 339S, 339W, 339Y, 341D, 341E, 341F, 341H, 341I, 341K, 341L, 341M, 341N, 341P, 341Q, 341R, 341S, 341T, 341V, 341W, 341Y, 343D, 343E, 343G, 343H, 343K, 343N, 343Q, 343R, 343S, 343T, 343W, 343Y, 373E, 373F, 373H, 373I, 373K, 373L, 373Q, 373R, 373T, 373W, 376A, 376G, 376N, 376P, 376Q, 376R, 376S, 376T, 376V, 377P, 379N, 379Q, 379T, 382I, 382L, 386K, 426D, 426L, 429F, 429M, 430A, 430D, 430F, 430G, 430H, 430I, 430K, 430L, 430M, 430N, 430P, 430R, 430S, 430T, 430V, 430W, 430Y, 431H, 431P, 434Y, 438L or 440Y] wherein the monoclonal antibody comprising the variant Fc region displays enhanced CDC activity as compared to the monoclonal antibody comprising the parent Fc region.

The invention provides a monoclonal antibody comprising a variant Fc region comprising at least one of the following amino acid substitutions in the Fc region: 235G, 235S, 236R, 237E, 237K, 237N, 237R, 238A, 238E, 238G, 238H, 238I, 238L, 238V, 238W, 238Y, 245R, 247H, 247I, 247L, 247T, 247Y, 250M, 252Y, 254D, 254E, 254I, 254P, 254Q, 254T, 254V, 255N, 257A, 257I, 257M, 257N, 257S, 257V, 262L, 264S, 265H, 265Y, 267G, 267H, 267I, 267K, 268K, 269N, 269Q, 270G, 270M, 270N, 271T, 272H, 272L, 272N, 292A, 293S, 301W, 307E, 311E, 311S, 316F, 318P, 327T, 328V, 329Y, 330K, 330R, 332E, 332M, 343I, 373S, 378D, 380D, 382D, 382F, 382N, 382P, 382R, 382S, 382W, 382Y, 385E, 385P, 423N, 424H, 424M or 427N [preferably 235G, 235S, 236R, 237E, 237K, 237N, 237R, 238A, 238E, 238G, 238H, 238I, 238L, 238V, 238W, 238Y, 245R, 247I, 247L, 247T, 250M, 257A, 257I, 257M, 262L, 264S, 267G, 267H, 267I, 267K, 268K, 269N, 269Q, 270G, 270M, 270N, 271T, 272H, 301W, 311S, 327T, 329Y, 330K, 378D, 385E, 423N or 424H] wherein the monoclonal antibody comprising the variant Fc region displays diminished CDC activity as compared to the monoclonal antibody comprising the parent Fc region.

The invention further embodies a monoclonal antibody comprising a variant Fc region of the invention, wherein said antibody specifically binds a human target antigen. Preferably the target antigen is selected from the group consisting of CD3, CD20, CD25, TNFα, Her2/neu, CD33, CD52, EGFR, EpCAM, MUC1, GD3, CEA, CA125, HLA-DR, TGFβ, VEGF, GDF8, GDF11, ghrelin, or any precursor or functional fragment thereof.

The invention provides a variant polypeptide comprising a variant Fc region comprising at least one of the following amino acid substitution in the Fc region: 238L, 244L, 245R, 249P, 252Y, 256P, 257A, 257I, 257M, 257N, 257S, 257V, 258D, 260S, 262L, 270K, 272L, 272R, 279A, 279D, 279G, 279H, 279M, 279N, 279Q, 279R, 279S, 279T, 279W, 279Y, 283A, 283D, 283F, 283G, 283H, 283I, 283K, 283L, 283N, 283P, 283Q, 283R, 283S, 283T, 283W, 283Y, 285N, 286F, 288N, 288P, 293V, 307E, 307M, 311A, 311I, 311K, 311L, 311M, 311V, 311W, 312P, 316K, 317P, 318N, 318T, 332F, 332H, 332K, 332L, 332M, 332R, 332S, 332W, 339N, 339T, 339W, 341P, 343E, 343H, 343K, 343Q, 343R, 343T, 343Y, 375R, 376G, 376I, 376M, 376P, 376T, 376V, 377K, 378D, 378N, 380N, 380S, 380T, 382F, 382H, 382I, 382K, 382L, 382M, 382N, 382Q, 382R, 382S, 382T, 382V, 382W, 382Y, 423N, 427N, 430A, 430F, 430G, 430H, 430I, 430K, 430L, 430M, 430N, 430Q, 430R, 430S, 430T, 430V, 430Y, 431H, 431K, 434F, 434G, 434H, 434W, 434Y, 436I, 436L, 436T, 438K, 438L, 438T, 438W, 440K or 442K, [preferably 245R, 252Y, 256P, 257A, 257I, 257M, 257N, 257S, 257V, 258D, 260S, 262L, 279A, 279D, 279G, 279H, 279N, 279Q, 279S, 279T, 279W, 279Y, 283F, 283H, 283K, 283R, 285N, 286F, 307E, 307M, 311I, 311K, 311L, 311M, 312P, 318N, 318T, 332S, 339W, 343E, 343H, 343K, 343Q, 343R, 375R, 377K, 378D, 378N, 380S, 380T, 382F, 382K, 382Q, 382R, 382S, 382T, 382V, 382W, 382Y, 423N, 427N, 430A, 430F, 430H, 430I, 430L, 430M, 430N, 430Q, 430R, 430S, 430V, 430Y, 431H, 431K, 434F, 434G, 434H, 434W, 434Y, 436I, 436L, 438K, 438L or 438W], wherein the variant polypeptide displays enhanced serum half-life as compared to the parent polypeptide (i.e., a polypeptide identical to the variant polypeptide but lacking the amino acid substitution listed hereinabove).

The invention provides a variant polypeptide comprising a variant Fc region comprising at least one of the following amino acid substitution in the Fc region: 235Q, 236Y, 237K, 237R, 238E, 238G, 238H, 238W, 247A, 247D, 247E, 247F, 247G, 247H, 247I, 247L, 247M, 247N, 247Q, 247R, 247S, 247W, 247Y, 248A, 248F, 248P, 248Q, 248W, 249E, 249L, 249M, 249Y, 251F, 251H, 251I, 251W, 254D, 254E, 254F, 254G, 254H, 254I, 254K, 254L, 254M, 254N, 254P, 254Q, 254R, 254T, 254V, 254W, 254Y, 255K, 255N, 256F, 256H, 256I, 256K, 256M, 256R, 256W, 256Y, 264S, 265S, 265Y, 267G, 267I, 268D, 268K, 270A, 270M, 279I, 279K, 279L, 280T, 292E, 292F, 292G, 292I, 292L, 311D, 311E, 311F, 311G, 311N 311R, 311Y, 315F, 315K, 315P, 316F, 317T, 326W, 327T, 339E, 339G, 339L, 339R, 341D, 341E, 341F, 341I, 341K, 341L, 341M, 341N, 341Q, 341R, 341S, 341T, 341V, 341W, 341Y, 343M, 343V, 343W, 373A, 373D, 373G, 373K, 373L, 373M, 373N, 373Q, 373S, 373T, 373V, 373W, 376H, 376L, 376W, 376Y, 424M, 424V, 426D, 429A, 429F, 429M, 430D, 430W, 431P, 432R, 432S, 439Q, 440D, 440E, 440F or 440M [preferably 237R, 247D, 247E, 247F, 247H, 247L, 247M, 247N, 247Q, 247W, 247Y, 248A, 248F, 248P, 248Q, 248W, 249L, 249M, 249Y, 251H, 251I, 251W, 254D, 254E, 254F, 254G, 254H, 254I, 254K, 254L, 254M, 254N, 254P, 254Q, 254R, 254T, 254V, 254W, 254Y, 255K, 255N, 256F, 256H, 256K, 256M, 256R, 256W, 265Y, 280T, 292G, 292I, 311D, 311E, 311G, 311N, 315F, 315P, 316F, 317T, 327T, 341D, 341E, 341F, 341I, 341L, 341Y, 343W, 373A, 373G, 373M, 373Q, 376W, 376Y, 424M, 424V, 430D, 430W, 431P or 432S], wherein the variant polypeptide displays diminished serum half-life as compared to the parent polypeptide (i.e., a polypeptide identical to the variant polypeptide but lacking the amino acid substitution listed hereinabove).

In one embodiment the invention provides a method for increasing the ADCC activity of a monoclonal antibody, preferably a therapeutic monoclonal antibody (or functional fragment thereof), comprising engineering a nucleic acid comprising a nucleic acid encoding a variant Fc region comprising at least one of the following amino acid substitutions: 247A, 247F, 247H, 247I, 247L, 247M, 247T, 247V, 247Y, 249E, 249Y, 251F, 254F, 254M, 254Y, 256A, 256M, 258D, 268D, 268E, 279A, 280A, 280K, 283A, 283I, 283K, 283M, 283R, 288N, 292A, 311A, 311D, 311N, 311T, 311V, 311Y, 315L, 318N, 318P, 318T, 318V, 330K, 332T, 332V, 339D, 339F, 339G, 339I, 339K, 339M, 339N, 339Q, 339R, 339S, 339T, 376A, 376V, 377G, 377K, 379N, 380N, 380S, 382A, 382I, 385E, 427N, 429M, 434W, 436I, 440G, 440H, 440I or 440L [preferably 247A, 247F, 247M, 247T, 247V, 247Y, 254F, 254Y, 258D, 279A, 283M, 288N, 292A, 311D, 311N, 311T, 315L, 318N, 318P, 318T, 318V, 339D, 339I, 339K, 339M, 339N, 339Q, 339R, 339S, 376A, 376V, 377K, 379N, 380N, 382A, 440I or 440L]. The nucleic acid molecule encoding the variant Fc region may be engineered (e.g., from a nucleic acid molecule encoding a parent Fc region or a native Fc region) to comprise at least one amino acid substitution as listed above either while the nucleic acid molecule is operably attached to additional antibody-encoding nucleic acid, (e.g., the nucleic acid sequence encoding the remainder of the Ig heavy chain), or the method may further comprise subsequently operably attaching the nucleic acid encoding the variant Fc region (i.e., after introduction of at least one amino acid substitution listed above) to additional antibody-encoding nucleic acid. The method may further comprise expression and purification of the monoclonal antibody comprising the variant Fc region. The method may further comprise expression and purification of the monoclonal antibody comprising the parent Fc region. The method may further comprise measuring ADCC activity of the monoclonal antibody comprising the variant Fc region and of the monoclonal antibody comprising the parent Fc region by any method available in the art or as described herein. The method may further comprise selecting a monoclonal antibody comprising a variant Fc region with ADCC activity greater than that of the monoclonal antibody comprising the parent Fc region (i.e., enhanced, preferably by at least 5%, 10%, 12%, 14%, 16%, 18%, 20% or more). The invention further embodies a monoclonal antibody, or functional fragment thereof, comprising a variant Fc region produced by the method.

In one embodiment the invention provides a method for decreasing the ADCC activity of a monoclonal antibody, preferably a therapeutic monoclonal antibody (or functional fragment thereof), comprising engineering a nucleic acid comprising a nucleic acid encoding a variant Fc region comprising at least one of the following amino acid substitutions: 235Q, 235R, 235S, 236F, 236R, 236Y, 237E, 237K, 237N, 237R, 238E, 238G, 238H, 238I, 238L, 238V, 238W, 238Y, 247G, 247R, 249L, 249P, 250K, 250M, 250R, 251H, 251I, 251W, 252Y, 254L, 254P, S254Q, 254T, 254V, 256V, 257A, 257I, 257M, 257N, 257S, 257V, 260S, 262L, 264S, 265H, 265K, 265S, 267G, S267H, 267I, 267K, 269N, 269Q, 270A, 270G, 270K, 270M, 270N, 271T, 272H, 272K, 272L, 272N, 272R, 279D, 279F, 279K, 279L, 279W, 283D, 283F, 283G, 283H, 283I, 283T, 283W, 283Y, 285N, 288P, 292E, 292F, 292G, 292I, 293S, 293V, 301W, 304E, 307A, 307E, 307M, 311F, 311I, 311K, 311S, 312P, 314F, 314I, 314V, 314Y, 315F, 315P, 316F, 317P, 327T, 328V, 329Y, 332G, 332K, 332L, 332R, 332W, 341D, 341E, 341F, 341H, 341I, 341K, 341L, 341M, 341N, 341P, 341Q, 341R, 341S, 341T, 341W, 341Y, 343A, 343D, 343E, 343F, 343G, 343H, 343L, 343M, 343N, 343Q, 343R, 343S, 343T, 343V, 343W, 343Y, 373A, 373D, 373E, 373F, 373G, 373I, 373K, 373L, 373M, 373N, 373Q, 373R, 373S, 373T, 373V, 373W, 375R, 376A, 376E, 376F, 376G, 376H, 376W, 376Y, 379Q, 382D, 382S, 429A, 429F, 430H, 430K, 430N, 430Q, 430R, 430W, 432R, 432S, 434I, 440D, 440T, 440V or 442K [preferably 235R, 236F, 236R, 236Y, 237E, 237K, 237N, 237R, 238E, 238G, 238H, 238I, 238L, 238V, 238W, 238Y, 247R, 249P, 250K, 251H, 254T, 257I, 257M, 257N, 257S, 257V, 265H, 265K, 265S, 267G, 267H, 267I, 267K, 269N, 269Q, 270A, 270G, 270K, 270M, 270N, 271T, 272R, 288P, 292E, 301W, 304E, 316F, 317P, 327T, 329Y, 332K, 332R, 341F, 341I, 341M, 341P, 341Q, 341R, 341T, 341W, 341Y, 343W, 373A, 373E, 373G, 373S, 376W, 429A, 432R or 432S]. The nucleic acid molecule encoding the variant Fc region may be engineered (e.g., from a nucleic acid molecule encoding a parent Fc region or a native Fc region) to comprise at least one amino acid substitution as listed above either while the nucleic acid molecule is operably attached to additional antibody-encoding nucleic acid, (e.g., the nucleic acid sequence encoding the remainder of the Ig heavy chain), or the method may further comprise subsequently operably attaching the nucleic acid encoding the variant Fc region (i.e., after introduction of at least one amino acid substitution listed above) to additional antibody-encoding nucleic acid. The method may further comprise expression and purification of the monoclonal antibody comprising the variant Fc region. The method may further comprise expression and purification of the monoclonal antibody comprising the parent Fc region. The method may further comprise measuring ADCC activity of the monoclonal antibody comprising the variant Fc region and of the monoclonal antibody comprising the parent Fc region by any method available in the art or as described herein. The method may further comprise selecting a monoclonal antibody comprising a variant Fc region with ADCC activity less than that of the monoclonal antibody comprising the parent Fc region (i.e., diminished, preferably by at least 5%, 10%, 12%, 14%, 16%, 18%, 20% or more). The invention further embodies a monoclonal antibody, or functional fragment thereof, comprising a variant Fc region produced by the method.

In one embodiment the invention provides a method for increasing the FcRn binding affinity of a monoclonal antibody, preferably a therapeutic monoclonal antibody (or functional fragment thereof), comprising engineering a nucleic acid comprising a nucleic acid encoding a variant Fc region comprising at least one of the following amino acid substitutions: 238L, 244L, 245R, 249P, 252Y, 256P, 257A, 257I, 257M, 257N, 257S, 257V, 258D, 260S, 262L, 270K, 272L, 272R, 279A, 279D, 279G, 279H, 279M, 279N, 279Q, 279R, 279S, 279T, 279W, 279Y, 283A, 283D, 283F, 283G, 283H, 283I, 283K, 283L, 283N, 283P, 283Q, 283R, 283S, 283T, 283W, 283Y, 285N, 286F, 288N, 288P, 293V, 307A, 307E, 307M, 311A, 311I, 311K, 311L, 311M, 311V, 311W, 312P, 316K, 317P, 318N, 318T, 332F, 332H, 332K, 332L, 332M, 332R, 332S, 332W, 339N, 339T, 339W, 341P, 343E, 343H, 343K, 343Q, 343R, 343T, 343Y, 375R, 376G, 376I, 376M, 376P, 376T, 376V, 377K, 378D, 378N, 380N, 380S, 380T, 382F, 382H, 382I, 382K, 382L, 382M, 382N, 382Q, 382R, 382S, 382T, 382V, 382W, 382Y, 423N, 427N, 430A, 430F, 430G, 430H, 430I, 430K, 430L, 430M, 430N, 430Q, 430R, 430S, 430T, 430V, 430Y, 431H, 431K, 434F, 434G, 434H, 434W, 434Y, 436I, 436L, 436T, 438K, 438L, 438T, 438W, 440K or 442K [preferably 245R, 252Y, 256P, 257A, 257I, 257M, 257N, 257S, 257V, 258D, 262L, 279A, 279D, 279G, 279H, 279N, 279Q, 279S, 279T, 279W, 279Y, 283F, 283H, 283K, 283R, 285N, 286F, 307A, 307E, 307M, 311I, 311K, 311L, 311M, 312P, 318N, 318T, 332S, 339W, 343E, 343H, 343K, 343Q, 343R, 375R, 377K, 378D, 378N, 380S, 380T, 382F, 382K, 382Q, 382R, 382S, 382T, 382V, 382W, 382Y, 423N, 427N, 430A, 430F, 430H, 430I, 430L, 430M, 430N, 430Q, 430R, 430S, 430V, 430Y, 431H, 431K, 434F, 434G, 434H, 434W, 434Y, 436I, 436L, 438K, 438L or 438W]. The nucleic acid molecule encoding the variant Fc region may be engineered (e.g., from a nucleic acid molecule encoding a parent Fc region or a native Fc region) to comprise at least one amino acid substitution as listed above either while the nucleic acid molecule is operably attached to additional antibody-encoding nucleic acid, (e.g., the nucleic acid sequence encoding the remainder of the Ig heavy chain), or the method may further comprise subsequently operably attaching the nucleic acid encoding the variant Fc region (i.e., after introduction of at least one amino acid substitution listed above) to additional antibody-encoding nucleic acid. The method may further comprise expression and purification of the monoclonal antibody comprising the variant Fc region. The method may further comprise expression and purification of the monoclonal antibody comprising the parent Fc region. The method may further comprise measuring FcRn binding affinity of the monoclonal antibody comprising the variant Fc region and of the monoclonal antibody comprising the parent Fc region by any method available in the art or as described herein. The method may further comprise selecting a monoclonal antibody comprising a variant Fc region with FcRn binding affinity greater than the FcRn binding affinity of the monoclonal antibody comprising the parent Fc region (i.e., enhanced, preferably by at least 5%, 10%, 12%, 14%, 16%, 18%, 20% or more). The invention further embodies a monoclonal antibody, or functional fragment thereof, comprising a variant Fc region produced by the method.

In one embodiment the invention provides a method for increasing the in vivo serum half-life of a polypeptide, preferably a therapeutic polypeptide, comprising engineering a nucleic acid comprising a nucleic acid encoding a variant Fc region comprising at least one of the following amino acid substitutions: 238L, 244L, 245R, 249P, 252Y, 256P, 257A, 257I, 257M, 257N, 257S, 257V, 258D, 260S, 262L, 270K, 272L, 272R, 279A, 279D, 279G, 279H, 279M, 279N, 279Q, 279R, 279S, 279T, 279W, 279Y, 283A, 283D, 283F, 283G, 283H, 283I, 283K, 283L, 283N, 283P, 283Q, 283R, 283S, 283T, 283W, 283Y, 285N, 286F, 288N, 288P, 293V, 307A, 307E, 307M, 311A, 311I, 311K, 311L, 311M, 311V, 311W, 312P, 316K, 317P, 318N, 318T, 332F, 332H, 332K, 332L, 332M, 332R, 332S, 332W, 339N, 339T, 339W, 341P, 343E, 343H, 343K, 343Q, 343R, 343T, 343Y, 375R, 376G, 376I, 376M, 376P, 376T, 376V, 377K, 378D, 378N, 380N, 380S, 380T, 382F, 382H, 382I, 382K, 382L, 382M, 382N, 382Q, 382R, 382S, 382T, 382V, 382W, 382Y, 423N, 427N, 430A, 430F, 430G, 430H, 430I, 430K, 430L, 430M, 430N, 430Q, 430R, 430S, 430T, 430V, 430Y, 431H, 431K, 434F, 434G, 434H, 434W, 434Y, 436I, 436L, 436T, 438K, 438L, 438T, 438W, 440K or 442K, [preferably 245R, 252Y, 256P, 257A, 257I, 257M, 257N, 257S, 257V, 258D, 262L, 279A, 279D, 279G, 279H, 279N, 279Q, 279S, 279T, 279W, 279Y, 283F, 283H, 283K, 283R, 285N, 286F, 307A, 307E, 307M, 311I, 311K, 311L, 311M, 312P, 318N, 318T, 332S, 339W, 343E, 343H, 343K, 343Q, 343R, 375R, 377K, 378D, 378N, 380S, 380T, 382F, 382K, 382Q, 382R, 382S, 382T, 382V, 382W, 382Y, 423N, 427N, 430A, 430F, 430H, 430I, 430L, 430M, 430N, 430Q, 430R, 430S, 430V, 430Y, 431H, 431K, 434F, 434G, 434H, 434W, 434Y, 436I, 436L, 438K, 438L or 438W]. The nucleic acid molecule encoding the variant Fc region may be operably linked to a nucleic acid molecule encoding a therapeutic protein. The nucleic acid molecule encoding a variant Fc region may be engineered (e.g., from a nucleic acid molecule encoding a parent Fc region or a native Fc region) to comprise at least one amino acid substitution as listed above while the nucleic acid molecule is operably attached to additional polypeptide-encoding nucleic acid, (e.g., the nucleic acid sequence encoding the non-Fc region of the fusion protein), or the method may further comprise subsequently operably attaching the nucleic acid encoding the variant Fc region after introduction of the at least one amino acid substitution listed above to nucleic acid encoding a non-Fc fusion partner. The method may further comprise expression and purification of the polypeptide comprising the variant Fc region. The method may further comprise expression and purification of the polypeptide comprising the parent Fc region. The method may further comprise measuring in vivo serum half-life of the polypeptide comprising the variant Fc region and of the polypeptide comprising the parent Fc region by any method available in the art or as described herein. The method may further comprise selecting a polypeptide comprising a variant Fc region wherein the polypeptide has increased in vivo serum half life as compared to that of the polypeptide comprising the parent Fc region (i.e., enhanced, preferably by at least 5%, 10%, 12%, 14%, 16%, 18%, 20% or more). The invention further embodies a polypeptide (i.e., a fusion polypeptide) comprising a variant Fc region produced by the method.

In one embodiment the invention provides a method for decreasing the FcRn binding affinity of a monoclonal antibody, preferably a therapeutic monoclonal antibody (or functional fragment thereof), comprising engineering a nucleic acid encoding a variant Fc region comprising at least one of the following amino acid substitutions: 235Q, 236Y, 237K, 237R, 238E, 238G, 238H, 238W, 247A, 247D, 247E, 247F, 247G, 247H, 247I, 247L, 247M, 247N, 247Q, 247R, 247S, 247W, 247Y, 248A, 248F, 248P, 248Q, 248W, 249E, 249L, 249M, 249Y, 251F, 251H, 251I, 251W, 254D, 254E, 254F, 254G, 254H, 254I, 254K, 254L, 254M, 254N, 254P, 254Q, 254R, 254T, 254V, 254W, 254Y, 255K, 255N, 256F, 256H, 256I, 256K, 256M, 256R, 256W, 256Y, 264S, 265S, 265Y, S267G, 267I, 268D, 268K, 270A, 270M, 279I, 279K, 279L, 280T, 292E, 292F, 292G, 292I, 292L, 311D, 311E, 311F, 311G, 311N, 311R, 311Y, 315F, 315K, 315P, 316F, 317T, 326W, 327T, 339E, 339G, 339L, 339R, 341D, 341E, 341F, 341I, 341K, 341L, 341M, 341N, 341Q, 341R, 341S, 341T, 341V, 341W, 341Y, 343M, 343V, 343W, 373A, 373D, 373G, 373K, 373L, 373M, 373N, 373Q, 373S, 373T, 373V, 373W, 376H, 376L, 376W, 376Y, 424M, 424V, 426D, 429A, 429F, 429M, 430D, 430W, 431P, 432R, 432S, 434I, 439Q, 440A, 440D, 440E, 440F or 440M [preferably 237R, 247D, 247E, 247F, 247H, 247L, 247M, 247N, 247Q, 247W, 247Y, 248A, 248F, 248P, 248Q, 248Q, 249L, 249M, 249Y, 251H, 251I, 251W, 254D, 254E, 254F, 254G, 254H, 254I, 254K, 254M, 254N, 254P, 254R, 254T, 254V, 254W, 254Y, 255K, 255N, 256F, 256H, 256K, 256M, 256R, 256W, 265Y, 280T, 292G, 292I, 311D, 311E, 311G, 311N, 315F, 315P, 316T, 317T, 327T, 341D, 341E, 341F, 341L, 341Y, 343W, 373A, 373G, 373M, 373Q, 376W, 376Y, 424M, 424V, 430D, 430W, 431P or 432S]. The nucleic acid molecule encoding a variant Fc region may be engineered (e.g., from a nucleic acid molecule encoding a parent Fc region or a native Fc region) to comprise at least one amino acid substitution as listed above while the nucleic acid encoding the variant Fc region is operably attached to nucleic acid encoding additional antibody sequence, (e.g., the nucleic acid sequence encoding the remainder of the Ig heavy chain), or the method may further comprise subsequently operably attaching the nucleic acid encoding the variant Fc region after introduction of the at least one amino acid substitution listed above to additional antibody-encoding nucleic acid. The method may further comprise expression and purification of the monoclonal antibody comprising the variant Fc region. The method may further comprise expression and purification of the monoclonal antibody comprising the parent Fc region. The method may further comprise measuring FcRn binding affinity of the monoclonal antibody comprising the variant Fc region and of the monoclonal antibody comprising the parent Fc region by any method available in the art or as described herein. The method may further comprise selecting a monoclonal antibody comprising a variant Fc region with FcRn binding affinity less than that of the monoclonal antibody comprising the parent Fc region (i.e., diminished, preferably by at least 5%, 10%, 12%, 14%, 16%, 18%, 20% or more). The invention further embodies a monoclonal antibody (comprising a variant Fc region) produced by the method.

In another embodiment the invention provides a method for decreasing the in vivo serum half-life of a polypeptide, preferably a therapeutic polypeptide, comprising engineering a nucleic acid encoding a variant Fc region comprising at least one of the following amino acid substitutions: 235Q, 236Y, 237K, 237R, 238E, 238G, 238H, 238W, 247A, 247D, 247E, 247F, 247G, 247H, 247I, 247L, 247M, 247N, 247Q, 247R, 247S, 247W, 247Y, 248A, 248F, 248P, 248Q, 248W, 249E, 249L, 249M, 249Y, 251F, 251H, 251I, 251W, 254D, 254E, 254F, 254G, 254H, 254I, 254K, 254L, 254M, 254N, 254P, 254Q, 254R, 254T, 254V, 254W, 254Y, 255K, 255N, 256F, 256H, 256I, 256K, 256M, 256R, 256W, 256Y, 264S, 265S, 265Y, S267G, 267I, 268D, 268K, 270A, 270M, 279I, 279K, 279L, 280T, 292E, 292F, 292G, 292I, 292L, 311D, 311E, 311F, 311G, 311N, 311R, 311Y, 315F, 315K, 315P, 316F, 317T, 326W, 327T, 339E, 339G, 339L, 339R, 341D, 341E, 341F, 341I, 341K, 341L, 341M, 341N, 341Q, 341R, 341S, 341T, 341V, 341W, 341Y, 343M, 343V, 343W, 373A, 373D, 373G, 373K, 373L, 373M, 373N, 373Q, 373S, 373T, 373V, 373W, 376H, 376L, 376W, 376Y, 424M, 424V, 426D, 429A, 429F, 429M, 430D, 430W, 431P, 432R, 432S, 434I, 439Q, 440A, 440D, 440E, 440F or 440M [preferably 237R, 247D, 247E, 247F, 247H, 247L, 247M, 247N, 247Q, 247W, 247Y, 248A, 248F, 248P, 248Q, 248Q, 249L, 249M, 249Y, 251H, 251I, 251W, 254D, 254E, 254F, 254G, 254H, 254I, 254K, 254M, 254N, 254P, 254R, 254T, 254V, 254W, 254Y, 255K, 255N, 256F, 256H, 256K, 256M, 256R, 256W, 265Y, 280T, 292G, 292I, 311D, 311E, 311G, 311N, 315F, 315P, 316T, 317T, 327T, 341D, 341E, 341F, 341L, 341Y, 343W, 373A, 373G, 373M, 373Q, 376W, 376Y, 424M, 424V, 430D, 430W, 431P or 432S]. The nucleic acid encoding the Fc variant region may be operably linked to nucleic acid encoding a therapeutic protein. The nucleic acid molecule encoding a variant Fc region may be engineered (e.g., from a nucleic acid molecule encoding a parent Fc region or a native Fc region) to comprise at least one amino acid substitution as listed above while the nucleic acid molecule is operably attached to additional polypeptide-encoding nucleic acid, (e.g., the nucleic acid sequence encoding the non-Fc region of the fusion protein), or the method may further comprise subsequently operably attaching the nucleic acid encoding the variant Fc region after introduction of the at least one amino acid substitution listed above to nucleic acid encoding a non-Fc fusion partner. The method may further comprise expression and purification of the polypeptide comprising the variant Fc region. The method may further comprise expression and purification of the polypeptide comprising the parent Fc region. The method may further comprise measuring in vivo serum half-life of the polypeptide comprising the variant Fc region and of the polypeptide comprising the parent Fc region by any method available in the art or as described herein. The method may further comprise selecting a polypeptide comprising a variant Fc region wherein the polypeptide has decreased in vivo serum half life as compared to that of the polypeptide comprising the parent Fc region (i.e., diminished, preferably by at least 5%, 10%, 12%, 14%, 16%, 18%, 20% or more). The invention further embodies a polypeptide (i.e., a fusion polypeptide) comprising a variant Fc region produced by the method.

In another embodiment the invention provides a method for increasing the CDC activity of a monoclonal antibody, preferably a therapeutic monoclonal antibody, comprising constructing the Fc region of the antibody to comprise at least one of the following amino acid substitutions: 236Y, 244L, 247A, 247D, 247E, 247G, 247N, 247Q, 247R, 247S, 247W, 248F, 248P, 248Q, 248W, 249E, 249L, 249M, 249N, 249P, 249Y, 250K, 250R, 251F, 251H, 251I, 251W, 254A, 254F, 254K, 254L, 254M, 254R, 254Y, 255K, 256A, 256G, 256I, 256L, 256M, 256P, 256Q, 256W, 256Y, 260S, 268D, 279Q, 279S, 279W, 279Y, 280K, 280T, 283F, 283G, 283H, 283I, 283K, 283L, 283M, 283N, 283P, 283R, 283S, 283W, 292L, 307A, 307M, 311F, 311I, 311K, 311L, 311M, 311T, 311V, 311W, 311Y, 312P, 314F, 314I, 314V, 314W, 314Y, 315F, 315K, 315L, 315P, 315R, 316K, 317P, 317T, 318N, 318T, 332A, 332D, 332E, 332F, 332G, 332H, 332L, 332M, 332N, 332Q, 332S, 332T, 332V, 332W, 332Y, 339D, 339F, 339G, 339H, 339I, 339K, 339N, 339Q, 339R, 339S, 339T, 339W, 339Y, 341D, 341E, 341F, 341H, 341I, 341K, 341L, 341M, 341N, 341P, 341Q, 341R, 341S, 341T, 341V, 341W, 341Y, 343A, 343D, 343E, 343G, 343H, 343K, 343L, 343M, 343N, 343Q, 343R, 343S, 343T, 343W, 343Y, 373D, 373E, 373F, 373H, 373I, 373K, 373L, 373M, 373N, 373Q, 373R, 373T, 373V, 373W, 375R, 376A, 376F, 376G, 376H, 376L, 376N, 376P, 376Q, 376R, 376S, 376T, 376V, 377P, 379N, 379Q, 379S, 379T, 380A, 380N, 380S, 380T, 382I, 382L, 382Q, 382V, 386K, 426D, 426L, 429A, 429F, 429M, 430A, 430D, 430F, 430G, 430H, 430I, 430K, 430L, 430M, 430N, 430P, 430R, 430S, 430T, 430V, 430W, 430Y, 431H, 431P, 432R, 432S, 434W, 434Y, 438L, 438W, 440Q or 440Y [preferably 236Y, 248F, 248P, 248Q, 248W, 249E, 249L, 249M, 249N, 249Y, 250K, 250R, 251H, 251I, 251W, 254A, 254F, 254K, 254L, 254M, 254R, 254Y, 255K, 256A, 256G, 256I, 256L, 256M, 256P, 256Q, 256W, 260S, 280K, 283W, 307M, 311F, 311I, 311K, 311L, 311M, 311T, 311V, 311W, 311Y, 314I, 314V, 314W, 314Y, 315P, 317P, 332D, 332L, 332M, 332S, 332W, 332Y, 339D, 339F, 339I, 339K, 339N, 339S, 339T, 339W, 339Y, 341D, 341E, 341F, 341H, 341I, 341K, 341L, 341M, 341N, 341P, 341Q, 341R, 341S, 341T, 341V, 341W, 341Y, 343D, 343E, 343G, 343H, 343K, 343N, 343Q, 343R, 343S, 343T, 343W, 343Y, 373D, 373E, 373H, 373I, 373K, 373L, 373Q, 373R, 373T, 373W, 376A, 376G, 376N, 376P, 376Q, 376R, 376S, 376T, 376V, 377P, 379N, 379Q, 379T, 382I, 382L, 386K, 426D, 426L, 429F, 429M, 430A, 430D, 430F, 430G, 430H, 430I, 430K, 430L, 430M, 430N, 430P, 430R, 430S, 430T, 430V, 430W, 430Y, 431H, 431P, 432R, 434Y, 438L or 440Y]. The nucleic acid molecule encoding a variant Fc region may be engineered (e.g., from a nucleic acid molecule encoding a parent Fc region or a native Fc region) to comprise at least one amino acid substitution as listed above while the nucleic acid molecule is operably attached to additional antibody-encoding nucleic acid, (e.g., the nucleic acid sequence encoding the remainder of the Ig heavy chain), or the method may further comprise subsequently operably attaching the nucleic acid encoding the variant Fc region after introduction of the at least one amino acid substitution listed above to additional antibody-encoding nucleic acid. The method may further comprise expression and purification of the monoclonal antibody comprising the variant Fc region. The method may further comprise expression and purification of the monoclonal antibody comprising the parent Fc region. The method may further comprise measuring CDC activity of the monoclonal antibody comprising the variant Fc region and of the monoclonal antibody comprising the parent Fc region by any method available in the art or as described herein. The method may further comprise selecting a monoclonal antibody comprising a variant Fc region with CDC activity greater than that of the monoclonal antibody comprising the parent Fc region (i.e., enhanced, preferably by at least 5%, 10%, 12%, 14%, 16%, 18%, 20% or more). The invention further embodies a monoclonal antibody comprising a variant Fc region produced by the method.

In another embodiment the invention provides a method for decreasing the CDC response of a monoclonal antibody, preferably a therapeutic monoclonal antibody, comprising constructing the Fc region of the antibody to comprise at least one of the following amino acid substitutions: 235G, 235S, 236R, 237E, 237K, 237N, 237R, 238A, 238E, 238G, 238H, 238I, 238L, 238V, 238W, 238Y, 245R, 247H, 247I, 247L, 247T, 247Y, 250M, 252Y, 254D, 254E, 254I, 254P, 254Q, 254T, 254V, 255N, 257A, 257I, 257M, 257N, 257S, 257V, 262L, 264S, 265H, 265Y, 267G, 267H, 267I, 267K, 268K, 269N, 269Q, 270G, 270M, 270N, 271T, 272H, 272L, 272N, 292A, 293S, 301W, 307E, 311E, 311S, 316F, 318P, 327T, 328V, 329Y, 330K, 330R, 332K, 339E, 339M, 343I, 373S, 378D, 380D, 382D, 382F, 382N, 382P, 382R, 382S, 382W, 382Y, 385E, 385P, 423N, 424H, 424M or 427N [preferably 235G, 235S, 236R, 237E, 237K, 237N, 237R, 238A, 238E, 238G, 238H, 238I, 238L, 238V, 238W, 238Y, 245R, 247I, 247L, 247T, 250M, 257A, 257I, 257M, 262L, 264S, 267G, 267H, 267I, 267K, 268K, 269N, 269Q, 270G, 270M, 270N, 271T, 272H, 301W, 311S, 327T, 329Y, 330K, 330R, 378D, 385E, 423N or 424H]. The nucleic acid molecule encoding a variant Fc region may be engineered (e.g., from a nucleic acid molecule encoding a parent Fc region or a native Fc region) to comprise at least one amino acid substitution as listed above while the nucleic acid molecule is operably attached to additional antibody-encoding nucleic acid, (e.g., the nucleic acid sequence encoding the remainder of the Ig heavy chain), or the method may further comprise subsequently operably attaching the nucleic acid encoding the variant Fc region after introduction of the at least one amino acid substitution listed above to additional antibody-encoding nucleic acid. The method may further comprise expression and purification of the monoclonal antibody comprising the variant Fc region. The method may further comprise expression and purification of the monoclonal antibody comprising the parent Fc region. The method may further comprise measuring CDC activity of the monoclonal antibody comprising the variant Fc region and of the monoclonal antibody comprising the parent Fc region by any method available in the art or as described herein. The method may further comprise selecting a monoclonal antibody comprising a variant Fc region with CDC activity less than that of the monoclonal antibody comprising the parent Fc region (i.e., diminished, preferably by at least 5%, 10%, 12%, 14%, 16%, 18%, 20% or more). The invention further embodies a monoclonal antibody comprising a variant Fc region produced by the method.

In another embodiment, the invention provides an isolated nucleic acid molecule that comprises a nucleic acid molecule that encodes a variant Fc region of the invention or a functional fragment thereof. More preferably the isolated nucleic acid molecule comprises a nucleic acid that encodes a polypeptide comprising a variant Fc region of the invention.

Preferably the variant Fc region polypeptide encoded by said nucleic acid has an amino acid substitution as shown in Table 1 as compared to the parent Fc region of the variant. Preferably, the polypeptide is a monoclonal antibody, and even more preferably, the monoclonal antibody is a full length antibody or a single-chain antibody. The monoclonal antibody may be a chimeric, humanized, or human monoclonal antibody.

In another embodiment, the invention provides a vector, preferably (but not limited to) a plasmid, a recombinant expression vector, a yeast expression vector, or a retroviral expression vector comprising a polynucleotide encoding a polypeptide comprising a variant Fc region polypeptide of the invention.

In another embodiment, the invention provides a host cell comprising a nucleic acid molecule of the present invention. Preferably a host cell of the invention comprises one or more vectors or constructs comprising a nucleic acid molecule of the present invention. The host cell of the invention is a cell into which a vector of the invention has been introduced (e.g., via transformation, transduction, infection, transfection, electroporation and the like), said vector comprising a polynucleotide encoding a polypeptide comprising a variant Fc region polypeptide of the invention. Optionally, the vector may be stably incorporated into the host cell chromosome. The host cell types include mammalian, bacterial, plant and yeast cells. Preferably the host cell is a CHO cell, a COS cell, a SP2/0 cell, a NS0 cell, a yeast cell or a derivative or progeny of any preferred cell type.

In another embodiment, the invention provides a pharmaceutical composition comprising a polypeptide comprising a variant Fc region of the invention, or functional fragment thereof. Preferably the polypeptide is a monoclonal antibody, even more preferably, a therapeutic monoclonal antibody. The monoclonal antibody may be a chimeric, humanized, or human monoclonal antibody. Alternatively, the polypeptide may be a polypeptide other than an antibody which benefits from an altered serum half life conferred upon the polypeptide by being operably linked to, and coexpressed with, a variant Fc region of the invention. The pharmaceutical composition of the invention may further comprise a pharmaceutically acceptable carrier. In said pharmaceutical composition, the polypeptide comprising the variant Fc region is the active ingredient. Preferably the pharmaceutical composition comprises a homogeneous or substantially homogeneous population of monoclonal antibody comprising a variant Fc region of the invention. The pharmaceutical composition for therapeutic use is preferably sterile and may be lyophilized.

The invention provides a method of inhibiting activity of a protein in a mammal, preferably a human, in need thereof comprising administering a therapeutically effective amount, or prophylactically effective amount, of a polypeptide (preferably a monoclonal antibody) comprising a variant Fc region of the invention to said mammal. Preferably, the polypeptide comprising the variant Fc region is a binding partner of the protein to be inhibited. The invention further provides a method of treating or preventing a disease or disorder ameliorated by the inhibition of signal transduction resulting from the binding of a monoclonal antibody comprising a variant Fc region of the invention to its antigenic epitope that comprises administering to a patient (e.g., a human) in need of such treatment or prevention a therapeutically or prophylactically effective amount of a monoclonal antibody of the invention.

The invention embodies an article of manufacture comprising a packaging material and a polypeptide comprising a variant Fc region polypeptide of the invention contained within said packaging material. The invention further embodies compositions comprising monoclonal antibodies and heterologous polypeptides that comprise a variant Fc region described herein, and a physiologically or pharmaceutically acceptable carrier or diluent.

In some embodiments, the present invention provides a polypeptide comprising: i) an unmodified human framework region ("FR") (e.g., no alterations have been made to a naturally occurring human framework), and ii) a variant Fc region. In certain embodiments, the unmodified human framework is a human germline framework. In other embodiments, the present invention provides compositions comprising a polypeptide, wherein the polypeptide comprises: i) at least one randomized CDR sequence and ii) a variant Fc region of the invention. In further embodiments, the present invention provides compositions comprising a polypeptide, wherein the polypeptide comprises: i) an unmodified human framework (e.g., human germline framework), ii) at least one randomized CDR sequence, and iii) a variant Fc region of the invention.

The present invention contemplates therapeutic and diagnostic uses for monoclonal antibodies heterologous polypeptides that comprise a variant Fc region of the invention, disclosed herein.

DESCRIPTION OF THE FIGURES

FIG. 2 shows an alignment of various parental Fc amino acid sequences, including human IgG1 ((SEQ ID NO:1) with non-a and a allotypes shown), human IgG2 (SEQ ID NO:2), human IgG3 (SEQ ID NO:3), human IgG4 (SEQ ID NO:4), murine IgG1 (SEQ ID NO:5), murine IgG2A (SEQ ID NO:6), murine IgG2B (SEQ ID NO:7), and murine IgG3 (SEQ ID NO:8).

FIGS. 3 A-D shows various amino acid sequences, including the CH2 region (SEQ ID NO:9), and CH3 region (SEQ ID NO: 10) of human IgG1, as well as an f allotype (SEQ ID NO: 11) and a,z allotype (SEQ ID NO:12) sequences of human IgG1 that include the CH1, hinge, CH2 and CH3 regions.

FIGS. 4 A-D shows various amino acid sequences comprised within: (a) the Light Chain Variable Region (LCVR) of anti-CD20 antibody (I) (SEQ ID NO: 13); (b) Heavy Chain Variable Region (HCVR) of anti-CD20 antibody (I) (SEQ ID NO: 14); (c) LCVR of anti-CD20 antibody (II) (SEQ ID NO: 15); and HCVR of anti-CD20 antibody (II) (SEQ ID NO: 16). FIG. 4e shows amino acid sequences comprised within the variable region of an anti-CD20 antibody. (see U.S. provisional application 60/471,958, filed May 20, 2003 and U.S. Pat. No. 5,843,439, both incorporated herein).

FIG. 5a shows the complete light chain amino acid sequence for the anti-CD20 antibody AME 133. FIG. 5b shows the complete light chain nucleic acid sequence for AME 133.

FIG. 6 shows amino acid and nucleic acid sequences for the complete heavy chain of three preferred variants of the anti-CD20 antibody AME 133. Specifically, FIG. 6a shows the amino acid sequence of the complete heavy chain of the 247I/339Q variant. FIG. 6b shows the nucleic acid sequence of the complete heavy chain of the 247I/339Q variant. FIG. 6c shows the amino acid sequence of the complete heavy chain of the 247I/339D variant. FIG. 6d shows the nucleic acid sequence of the complete heavy chain of the 247I/339D variant. FIG. 6e shows the amino acid sequence of the complete heavy chain of the 378D variant. FIG. 6f shows the nucleic acid sequence of the complete heavy chain of the 378D variant.

DETAILED DESCRIPTION

Figure 1:
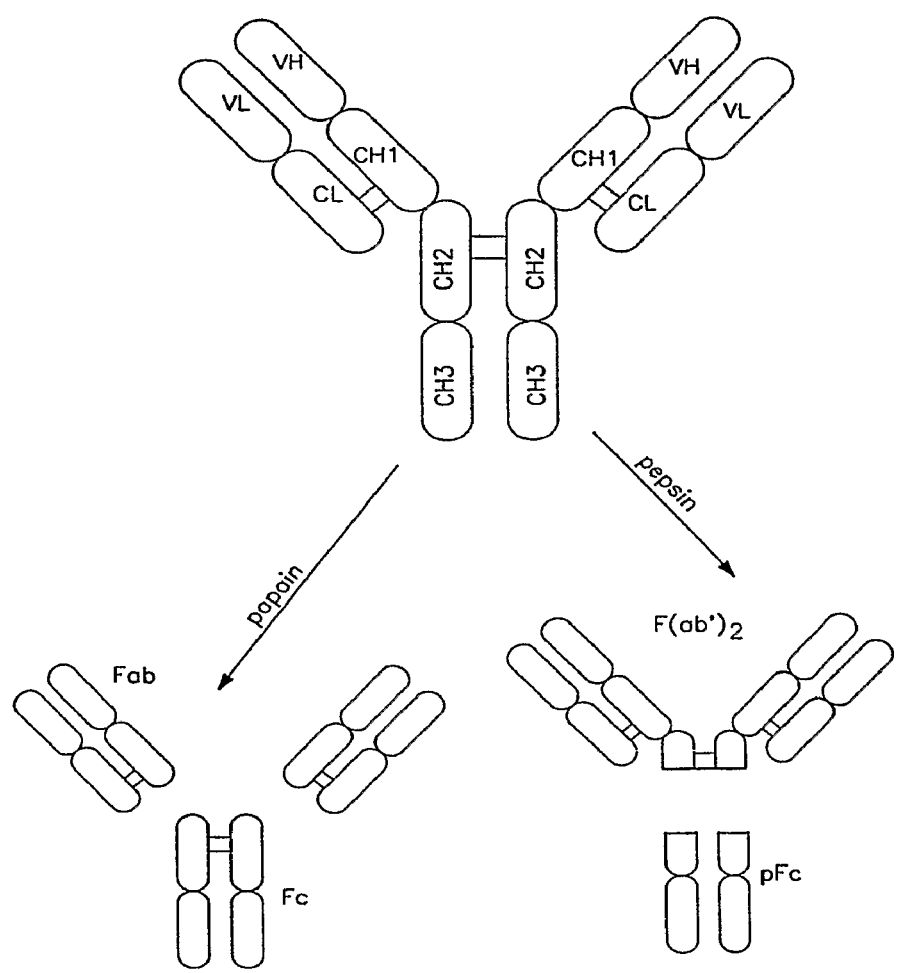
FIG. 1 shows a schematic representation of an IgG molecule with the various regions and sections labeled.

Throughout the present specification and claims, the numbering of the amino acid residues in an immunoglobulin heavy chain (Fc region) is that of the EU index as in Kabat et al., *Sequences of Proteins of Immunological Interest*, 5$^{th}$ Ed. Public Health Service, National Institutes of Health, Bethesda, Md. (1991). The "EU index as in Kabat" refers to the residue numbering of the human IgG antibody and is reflected herein in FIG. 2. For example, at position 438, human IgG1, IgG2, IgG3, IgG4 and murine IgG3 all have a Q amino acid, while murine IgG1 has an I amino acid, murine IgG2a has a T amino acid, and murine IgG2B has a K amino acid. Furthermore, substitutions are named herein by the amino acid position number at which the substitution occurs followed by the amino acid substituted for that present in the parent Fc region at the same position (e.g., 249G indicates a glycine residue substituted for that present at position 249 of the parent Fc region). The number refers to the position in human IgG1 regardless of whether or not the parent Fc region is human IgG1; if the parent Fc region is not human IgG1, the number refers to the homologous position in the parent Fc region if it were aligned with human IgG1 at that position.

As used herein, the terms "subject" and "patient" refer to any animal in which a polypeptide comprising a variant Fc region of the invention may be used therapeutically including a human as well as other mammals (such as e.g., domestic animals (e.g., canine, feline), sports animals (e.g., equine) and food-source animals (e.g., bovine, porcine and ovine)) who may benefit from such therapy.

As used herein, "treating or preventing" refers to a disease or disorder associated with abnormal levels of a protein or benefited by altering an activity or level of a protein.

The term "isolated" when used in relation to a nucleic acid is a nucleic acid that is identified and separated from at least one contaminant nucleic acid with which it is ordinarily associated in its natural source. Isolated nucleic acid is in a form or setting different from that in which it is found in nature. Isolated nucleic acid molecules therefore are distinguished from the nucleic acid molecule as it exists in natural cells. An isolated nucleic acid molecule includes a nucleic acid molecule contained in cells that ordinarily express the polypeptide encoded therein where, for example, the nucleic acid molecule is in a plasmid or a chromosomal location different from that of natural cells. The isolated nucleic acid may be present in single-stranded or double-stranded form. When an isolated nucleic acid molecule is to be utilized to express a protein, the oligonucleotide or polynucleotide will contain at a minimum the sense or coding strand, but may contain both the sense and anti-sense strands (i.e., may be double-stranded).

A nucleic acid molecule is "operably linked" or "operably attached" when it is placed into a functional relationship with another nucleic acid molecule. For example, a promoter or enhancer is operably linked to a coding sequence of nucleic acid if it affects the transcription of the sequence; or a ribosome binding site is operably linked to a coding sequence of nucleic acid if it is positioned so as to facilitate translation. A nucleic acid molecule encoding a variant Fc region is operably linked to a nucleic acid molecule encoding a heterologous protein (i.e., a protein or functional fragment thereof which does not, as it exists in nature, comprise an Fc region) if it is positioned such that the expressed fusion protein comprises the heterologous protein or functional fragment thereof adjoined either upstream or downstream to the variant Fc region polypeptide; the heterologous protein may by immediately adjacent to the variant Fc region polypeptide or may be separated therefrom by a linker sequence of any length and composition. Likewise, a polypeptide (used synonymously herein with "protein") molecule is "operably linked" or "operably attached" when it is placed into a functional relationship with another polypeptide.

As used herein the term "functional fragment" when in reference to a polypeptide or protein (e.g., a variant Fc region, or a monoclonal antibody) refers to fragments of that protein which retain at least one function of the full-length polypeptide. The fragments may range in size from six amino acids to the entire amino acid sequence of the full-length polypeptide minus one amino acid. A functional fragment of a variant Fc region polypeptide of the present invention retains at least one "amino acid substitution" as herein defined. A functional fragment of a variant Fc region polypeptide retains at least one function known in the art to be associated with the Fc region (e.g., ADCC, CDC, Fc receptor binding, Clq binding, down regulation of cell surface receptors or may, e.g., increase the in vivo or in vitro half-life of a polypeptide to which it is operably attached).

The term "purified" or "purify" refers to the substantial removal of at least one contaminant from a sample. For example, an antigen-specific antibody may be purified by complete or substantial removal (at least 90%, 91%, 92%, 93%, 94%, 95%, or more preferably at least 96%, 97%, 98% or 99%) of at least one contaminating non-immunoglobulin protein; it may also be purified by the removal of immunoglobulin protein that does not bind to the same antigen. The removal of non-immunoglobulin proteins and/or the removal of immunoglobulins that do not bind a particular antigen results in an increase in the percent of antigen-specific immunoglobulins in the sample. In another example, a polypeptide (e.g., an immunoglobulin) expressed in bacterial host cells is purified by the complete or substantial removal of host cell proteins; the percent of the polypeptide is thereby increased in the sample.

The term "native" as it refers to a polypeptide (e.g., Fc region) is used herein to indicate that the polypeptide has an amino acid sequence consisting of the amino acid sequence of the polypeptide as it commonly occurs in nature or a naturally occurring polymorphism thereof. A native polypeptide (e.g., native Fc region) may be produced by recombinant means or may be isolated from a naturally occurring source.

The term "expression vector" as used herein refers to a recombinant DNA molecule containing a desired coding sequence and appropriate nucleic acid sequences necessary for the expression of the operably linked coding sequence in a particular host organism.

As used herein, the term "host cell" refers to any eukaryotic or prokaryotic cell (e.g., bacterial cells such as *E. coli*, CHO cells, yeast cells, mammalian cells, avian cells, amphibian cells, plant cells, fish cells, and insect cells), whether located in vitro or in situ, or in vivo. For example, host cells may be located in a transgenic animal.

As used herein a "parent polypeptide" is a polypeptide comprising an amino acid sequence that may be changed or altered (e.g., an amino acid substitution) to produce a variant (i.e., variant polypeptide). In preferred embodiments, the parent polypeptide comprises at least a portion of a native or non-native Fc region, i.e., a naturally occurring Fc region or an Fc region with at least one amino acid sequence modification. In some embodiments, variants that are shorter or longer than the parent polypeptide are specifically contemplated. In particularly preferred embodiments, the parent polypeptide differs in function (e.g., enhanced or diminished effector function, receptor binding, in vivo or in vitro half-life, etc.) as compared to the variant.

As used herein, the term "variant of a parent polypeptide" refers to a polypeptide comprising an amino acid sequence that differs from that of the parent polypeptide by at least one amino acid substitution. In certain embodiments, the variant comprises at least 40%, 45%, 50%, 55%, 60%, 65%, 70%, 75%, 80%, 85% or 90% or most preferably at least 95%, 97% or 99% of an Fc region (i.e., a "portion" of the Fc region). In preferred embodiments, a variant Fc region of a parent polypeptide comprises at least one amino acid substitution from the parent polypeptide, the substitution being in the Fc region. The parent polypeptide may or may not be a native polypeptide.

As used herein, the term "Fc region" refers to a C-terminal region of an immunoglobulin heavy chain (e.g., as shown in FIG. 1). The "Fc region" may be a native sequence Fc region or a variant Fc region. Although the generally accepted boundaries of the Fc region of an immunoglobulin heavy chain might vary, the human IgG heavy chain Fc region is usually defined to stretch from an amino acid residue at position Cys226, or from Pro230, to the carboxyl-terminus thereof. In some embodiments, variants comprise only portions of the Fc region and can include or not include the carboxy-terminus. The Fc region of an immunoglobulin generally comprises two constant domains, CH2 and CH3, as shown, e.g., in FIG. 1. In some embodiments, variants having one or more of the constant domains are contemplated. In other embodiments, variants without such constant domains (or with only portions of such constant domains) are contemplated.

The "CH2 domain" of a human IgG Fc region (also referred to as "Cγ2" domain) usually extends from about amino acid 231 to about amino acid 340 (see FIG. 2). The CH2 domain is unique in that it is not closely paired with another domain. Two N-linked branched carbohydrate chains are interposed between the two CH2 domains of an intact native IgG molecule.

The "CH3 domain" of a human IgG Fc region (also referred to as "Cγ3" domain) generally is the stretch of residues C-terminal to a CH2 domain in an Fc region extending from about amino acid residue 341 to about amino acid residue 447 (see FIG. 2).

A "functional Fc region" possesses an "effector function" of a native sequence Fc region. At least one effector function of a polypeptide comprising a variant Fc region of the present invention may be enhanced or diminished with respect to a polypeptide comprising a native Fc region or the parent Fc region of the variant. Examples of effector functions include, but are not limited to: C1q binding; complement dependent cytotoxicity (CDC); Fc receptor binding; antibody-depended cell-mediated cytotoxicity (ADCC); phagocytosis; down regulation of cell surface receptors (e.g., B cell receptor; BCR), etc. Such effector functions may require the Fc region to be operably linked to a binding domain (e.g., an antibody variable domain) and can be assessed using various assays (e.g., Fc binding assay, ADCC assays, CDC assays, target cell depletion from whole or fractionated blood samples, etc.).

A "native sequence Fc region" or "wild type Fc region" refers to an amino acid sequence that is identical to the amino acid sequence of an Fc region commonly found in nature. Exemplary native sequence human Fc regions are shown in FIG. 2 and include a native sequence human IgG1 Fc region. (f and a,z allotypes, i.e., non-A and A allotypes); native sequence human IgG2 Fc region; native sequence human IgG3 Fc region; and native sequence human IgG4 Fc region as well as naturally occurring variants thereof. Native sequence murine Fc regions are also shown in FIG. 2.

A "variant Fc region" comprises an amino acid sequence that differs from that of a native sequence Fc region (or fragment thereof) by virtue of at least one "amino acid substitution" as defined herein. In preferred embodiments, the variant Fc region has at least one amino acid substitution compared to a native sequence Fc region or in the Fc region of a parent polypeptide, preferably 1, 2, 3, 4 or 5 amino acid substitutions in a native sequence Fc region or in the Fc region of the parent polypeptide. In an alternative embodiment, a variant Fc region may be generated according to the methods herein disclosed and this variant Fc region can be fused to a heterologous polypeptide of choice, such as an antibody variable domain or a non-antibody polypeptide, e.g., binding domain of a receptor or ligand.

As used herein, the term "derivative" in the context of polypeptides refers to a polypeptide that comprises and amino acid sequence which has been altered by introduction of an amino acid residue substitution. The term "derivative" as used herein also refers to a polypeptide which has been modified by the covalent attachment of any type of molecule to the polypeptide. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide may be produced by chemical modifications using techniques known to those of skill in the art, including, but not limited to specific chemical cleavage, acetylation, formylation, metabolic synthesis of tunicamycin, etc. Further, a derivative polypeptide possesses a similar or identical function as the polypeptide from which it was derived. It is understood that a polypeptide comprising a variant Fc region of the present invention may be a derivative as defined herein, preferably the derivatization occurs within the Fc region.

"Substantially of human origin" as used herein in reference to a polypeptide (e.g., an Fc region or a monoclonal antibody), indicates the polypeptide has an amino acid sequence at least 80%, at least 85%, more preferably at least 90%, 91%, 92%, 93%, 94% or even more preferably at least 95%, 95%, 97%, 98% or 99% homologous to that of a native human amino polypeptide.

The terms "Fc receptor" or "FcR" are used to describe a receptor that binds to an Fc region (e.g., the Fc region of an antibody). The preferred FcR is a native sequence FcR. Moreover, a preferred FcR is one which binds an IgG antibody (a gamma receptor) and includes receptors of the FcγRI, FcγRII, FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, *Annu. Rev. Immunol.* 9:457-92 (1991); Capel, et al., *Immunomethods* 4:25-34 (1994); and de Haas et al., *J. Lab. Clin. Med.* 126: 330-41 (1995). Another preferred FcR includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)). Other FcRs, including those to be identified in the future, are encompassed by the term "FcR" herein.

The phrase "antibody-dependent cell-mediated cytotoxicity" and "ADCC" refer to a cell-mediated reaction in which nonspecific cytotoxic cells (e.g., nonspecific) that express FcRs (e.g., Natural Killer ("NK") cells, neutrophils, and macrophages) recognize bound antibody on a target cell and subsequently cause lysis of the target cells. The primary cells for mediating ADCC, NK cells, express FcγRIII only, whereas monocytes express FcγRI, FcγRII and FcγRIII.

As used herein, the phrase "effector cells" refers to leukocytes (preferably human) which express one or more FcRs and perform effector functions. Preferably, the cells express at least FcγRIII and perform ADCC effector function. Examples of leukocytes which mediate ADCC include PBMC, NK cells, monocytes, cytotoxic T cells and neutrophils. The effector cells may be isolated from a native source (e.g., from blood or PBMCs).

A variant polypeptide with "altered" FcRn binding affinity is one which has either enhanced (i.e., increased, greater or higher) or diminished (i.e., reduced, decreased or lesser) FcRn binding affinity compared to the variant's parent polypeptide or to a polypeptide comprising a native Fc region when measured at pH 6.0. A variant polypeptide which displays increased binding or increased binding affinity to an FcRn binds FcRn with greater affinity than the parent polypeptide. A variant polypeptide which displays decreased binding or decreased binding affinity to an FcRn, binds FcRn with lower affinity than its parent polypeptide. Such variants which display decreased binding to an FcRn may possess little or no appreciable binding to an FcRn, e.g., 0-20% binding to the FcRn compared to a parent polypeptide. A variant polypeptide which binds an FcRn with "enhanced affinity" as compared to its parent polypeptide, is one which binds FcRn with higher binding affinity than the parent polypeptide, when the amounts of variant polypeptide and parent polypeptide in a binding assay are essentially the same, and all other conditions are identical. For example, a variant polypeptide with enhanced FcRn binding affinity may display from about 1.10 fold to about 100 fold (more typically from about 1.2 fold to about 50 fold) increase in FcRn binding affinity compared to the parent polypeptide, where FcRn binding affinity is determined, for example, in an ELISA assay or other method available to one of ordinary skill in the art.

As used herein, an "amino acid substitution" refers to the replacement of at least one existing amino acid residue in a given amino acid sequence with another different "replacement" amino acid residue. The replacement residue or residues may be "naturally occurring amino acid residues" (i.e., encoded by the genetic code) and selected from: alanine (Ala); arginine (Arg); asparagine (Asn); aspartic acid (Asp); cysteine (Cys); glutamine (Gln); glutamic acid (Glu); glycine (Gly); histidine (His); isoleucine (Ile); leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues (s) in a polypeptide chain. Examples of non-naturally occurring amino acid residues include norleucine, ornithine, norvaline, homoserine and other amino acid residue analogues such as those described in Ellman et al. Meth. Enzym. 202: 301-336 (1991).

The term "assay signal" refers to the output from any method of detecting protein-protein interactions, including but not limited to, absorbance measurements from colorimetric assays, fluorescent intensity, or disintegrations per minute. Assay formats could include ELISA, facs, or other methods. A change in the "assay signal" may reflect a change in cell viability and/or a change in the kinetic off-rate, the kinetic on-rate, or both. A "higher assay signal" refers to the measured output number being larger than another number (e.g., a variant may have a higher (larger) measured number in an ELISA assay as compared to the parent polypeptide). A "lower" assay signal refers to the measured output number being smaller than another number (e.g., a variant may have a lower (smaller) measured number in an ELISA assay as compared to the parent polypeptide).

The term "binding affinity" refers to the equilibrium dissociation constant (expressed in units of concentration) associated with each Fc receptor-Fc binding interaction. The binding affinity is directly related to the ratio of the kinetic off-rate (generally reported in units of inverse time, e.g., seconds$^{-1}$) divided by the kinetic on-rate (generally reported in units of concentration per unit time, e.g., molar/second). In general it is not possible to unequivocally state whether changes in equilibrium dissociation constants are due to differences in on-rates, off-rates or both unless each of these parameters are experimentally determined (e.g., by BIACORE or SAPIDYNE measurements).

As used herein, the term "hinge region" refers to the stretch of amino acids in human IgG1 stretching from Glu216 to Pro230 of human IgG1. Hinge regions of other IgG isotypes may be aligned with the IgG1 sequence by placing the first and last cysteine residues forming inter-heavy chain S—S bonds in the same positions.

"C1q" is a polypeptide that includes a binding site for the Fc region of an immunoglobulin. C1q together with two serine proteases, C1r and C1s, forms the complex C1, the first component of the CDC pathway.

As used herein, the term "antibody" is used interchangeably with "immunoglobulin" or "Ig," is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity or functional activity. Single chain antibodies, and chimeric, human, humanized or primatized (CDR-grafted) antibodies, as well as chimeric or CDR-grafted single chain antibodies, and the like, comprising portions derived from different species, are also encompassed by the present invention and the term "antibody". The various portions of these antibodies can be joined together chemically by conventional techniques, synthetically, or can be prepared as a contiguous protein using genetic engineering techniques. For example, nucleic acids encoding a chimeric or humanized chain can be expressed to produce a contiguous protein. See, e.g., U.S. Pat. No. 4,816,567; European Patent No. 0,125,023 B1; U.S. Pat. No. 4,816,397; European Patent No. 0,120,694 B1; WO 86/01533; European Patent No. 0,194,276 B1; U.S. Pat. No. 5,225,539; European Patent No. 0,239,400 B1 and U.S. Pat. Nos. 5,585,089 and 5,698,762. See also, Newman, R. et al. *BioTechnology*, 10: 1455-1460, 1993, regarding primatized antibody, and Ladner et al., U.S. Pat. No. 4,946,778 and Bird, R. E. et al., *Science*, 242:423-426, 1988, regarding single chain antibodies. It is understood that all forms of the antibodies comprising an Fc region (or portion thereof) are encompassed herein within the term "antibody." Furthermore, the antibody may be labeled with a detectable label, immobilized on a solid phase and/or conjugated with a heterologous compound (e.g., an enzyme or toxin) according to methods known in the art.

As used herein, the term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments. The antibody fragments preferably retain at least part of the hinge and optionally the CH1 region of an IgG heavy chain. In other preferred embodiments, the antibody fragments comprise at least a portion of the CH2 region or the entire CH2 region.

As used herein, the term "functional fragment", when used in reference to a monoclonal antibody, is intended to refer to a portion of the monoclonal antibody that still retains a functional activity. A functional activity can be, for example, antigen binding activity or specificity, receptor binding activity or specificity, effector function activity and the like. Monoclonal antibody functional fragments include, for example, individual heavy or light chains and fragments thereof, such as VL, VH and Fd; monovalent fragments, such as Fv, Fab, and Fab'; bivalent fragments such as F(ab')2; single chain Fv (scFv); and Fc fragments. Such terms are described in, for example, Harlowe and Lane, Antibodies: A Laboratory Manual, Cold Spring Harbor Laboratory, New York (1989); Molec. Biology and Biotechnology: A Comprehensive Desk Reference (Myers, R. A. (ed.), New York: VCH Publisher, Inc.); Huston et al., Cell Biophysics, 22:189-224 (1993); Pluckthun and Skerra, Meth. Enzymol., 178:497-515 (1989) and in Day, E. D., Advanced Immunochemistry, Second Ed., Wiley-Liss, Inc., New York, N.Y. (1990). The term functional fragment is intended to include, for example, fragments produced by protease digestion or reduction of a monoclonal antibody and by recombinant DNA methods known to those skilled in the art.

As used herein, the term "fragment" refers to a polypeptide comprising an amino acid sequence of at least 5, 15, 20, 25, 40, 50, 70, 90, 100 or more contiguous amino acid residues of the amino acid sequence of another polypeptide. In a preferred embodiment, a fragment of a polypeptide retains at least one function of the full-length polypeptide.

As used herein, the term "chimeric antibody" includes monovalent, divalent or polyvalent immunoglobulins. A monovalent chimeric antibody is a dimer formed by a chimeric heavy chain associated through disulfide bridges with a chimeric light chain. A divalent chimeric antibody is a tetramer formed by two heavy chain-light chain dimers associated through at least one disulfide bridge. A chimeric heavy chain of an antibody for use in humans comprises an antigen-binding region derived from the heavy chain of a non-human antibody, which is linked to at least a portion of a human heavy chain constant region, such as CH1 or CH2. A chimeric light chain of an antibody for use in humans comprises an antigen binding region derived from the light chain of a non-human antibody, linked to at least a portion of a human light chain constant region (CL). Antibodies, fragments or derivatives having chimeric heavy chains and light chains of the same or different variable region binding specificity, can also be prepared by appropriate association of the individual polypeptide chains, according to known method steps. With this approach, hosts expressing chimeric heavy chains are separately cultured from hosts expressing chimeric light chains, and the immunoglobulin chains are separately recovered and then associated. Alternatively, the hosts can be co-cultured and the chains allowed to associate spontaneously in the culture medium, followed by recovery of the assembled immunoglobulin or fragment or both the heavy and light chains can be expressed in the same host cell. Methods for producing chimeric antibodies are known in the art (see, e.g., U.S. Pat. Nos. 6,284,471; 5,807,715; 4,816,567; and 4,816, 397).

As used herein, "humanized" forms of non-human (e.g., murine) antibodies (i.e., humanized antibodies) are antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops (CDRs) correspond to those of a nonhuman immunoglobulin and all or substantially all of the FR residues are those of a human immunoglobulin sequence. The humanized antibody may also comprise at least a portion of an immunoglobulin constant region (Fc), typically that of a human immunoglobulin. An exemplary method used to generate humanized antibodies is described in U.S. Pat. No. 5,225,539.

As used herein, the term "immunoadhesin" designates antibody-like molecules which combine the binding domain of a heterologous "adhesin" protein (e.g., a receptor, ligand or enzyme) with an immunoglobulin constant domain. Structurally, immunoadhesins comprise a fusion of the adhesin amino acid sequence with the desired binding specificity which is other than the antigen recognition and binding site (antigen combining site) of an antibody (i.e., is "heterologous") with an immunoglobulin constant domain sequence.

As used herein, the term "ligand binding domain" refers to any native receptor or any region or derivative thereof retaining at least a qualitative ligand binding ability of a corresponding native receptor. In certain embodiments, the receptor is from a cell-surface polypeptide having an extracellular domain that is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules (e.g., E-, L-, and P-selectins).

As used herein, the term "receptor binding domain" refers to any native ligand for a receptor, including, e.g., cell adhesion molecules, or any region or derivative of such native ligand retaining at least a qualitative receptor binding ability of a corresponding native ligand.

As used herein, the term "antibody-immunoadhesin chimera" comprises a molecule that combines at least one binding domain of an antibody with at least one immunoadhesin. Examples include, but are not limited to, the bispecific CD4-IgG chimeras described in Berg et al., PNAS (USA) 88:4723-4727 (1991) and Charnow et al., J. Immunol., 153:4268 (1994).

As used herein, an "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or non-proteinaceous solutes. In certain embodiments, the isolated polypeptide is purified (1) to greater than 95% by weight of polypeptides as determined by the Lowry method, and preferably, more than 99% by weight, (2) to a degree sufficient to obtain at least 15 residues of N-terminal or internal amino acid sequence by use of a spinning cup sequenator, or (3) to homogeneity by SDS-page under reducing or nonreducing conditions using Coomassie blue or silver stain. Isolated polypeptide includes the polypeptide in situ within recombinant cells since at least one component of the polypeptide's natural environment will not be present. Ordinarily, however, isolated polypeptide will be prepared by a least one purification step.

As used herein, the term "treatment" refers to both therapeutic treatment and prophylactic or preventative measures. Those subjects or patients in need of treatment include those already with the disorder as well as those in which the disorder is to be prevented.

As used herein, the term "disorder" and "disease" are used interchangeably to refer to any condition that would benefit from treatment with a variant polypeptide (a polypeptide comprising a variant Fc region of the invention), including chronic and acute disorders or diseases (e.g., pathological conditions that predispose a patient to a particular disorder). In certain embodiments, the disorder is cancer. In certain embodiments, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation. Autoimmune disorders may or may not be associated with inflammation. Moreover, inflammation may or may not be caused by autoimmune disorder. Certain disorders may be characterized as both autoimmune and inflammatory disorders.

As used herein, the terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer. As used herein, the term "label" refers to a detectable compound or composition that is conjugated directly or indirectly to a polypeptide. The label may itself be detectable (e.g., radioisotope labels or fluorescent labels) or, in the case of an enzymatic label, may catalyze chemical alteration of a substrate compound or composition which is detectable.

As used herein, the term "receptor" refers to a polypeptide capable of binding at least one ligand. The preferred receptor is a cell-surface or soluble receptor having an extracellular ligand-binding domain and, optionally, other domains (e.g., transmembrane domain, intracellular domain and/or membrane anchor). A receptor to be evaluated in an assay described herein may be an intact receptor or a fragment or derivative thereof (e.g. a fusion protein comprising the binding domain of the receptor fused to one or more heterologous polypeptides). Moreover, the receptor to be evaluated for its binding properties may be present in a cell or isolated and optionally coated on an assay plate or some other solid phase or labeled directly and used as a probe.

As used herein, the term "antibody responsive disease" refers to any disease or medical condition that is shown to be treatable, at least in part, with antibody therapy. Examples of such diseases and medical conditions include, but are not limited to, lymphoma (shown to be treatable with RITUXAN), infectious disease (respiratory syncytia virus shown to be treatable with SYNAGIS), kidney transplant (ZENAPAX has shown to be helpful), Crohn's disease and rheumatoid arthritis (shown to be treatable with REMICADE), breast carcinoma (shown to be treatable with HERCEPTIN), and colon cancer (shown to be treatable with EDRECOLOMAB). As used herein, the term "immunoadhesin responsive disease" refers to any disease or medical condition that is shown to be treatable, at least in part, with immunoadhesin therapy.

As used herein a variant polypeptide that "mediates antibody-dependent cell-mediated cytotoxicity (ADCC) in the presence of human effector cells more effectively" than a parent antibody is one which in vitro or in vivo is substantially more effective at mediating ADCC, when the amounts of variant polypeptide and parent antibody used in the assay are essentially the same. For example, such a variant causes a higher amount of target cell lysis in a given ADCC assay than the parent polypeptide in an identical ADCC assay. Such variants may be identified, for example, using an ADCC assay, but other assays or methods for determining ADCC activity may also be employed (e.g., animal models). In preferred embodiments, the variant polypeptide is from about 1.2, 1.3 or 1.4 fold, 1.5 fold, 50 fold, 100 fold, about 500 fold, or about 1000 fold more effective at mediating ADCC than the parent polypeptide.

The term "symptoms of an antibody or immunoadhesin responsive disease" refers to those symptoms generally associated with a particular disease. For example, the symptoms normally associated with Crohn's disease include: abdominal pain, diarrhea, rectal bleeding, weight loss, fever, loss of appetite, dehydration, anemia, distention, fibrosis, inflamed intestines and malnutrition. The phrase "under conditions such that the symptoms are reduced" refers to any degree of qualitative or quantitative reduction in detectable symptoms of any antibody or immunoadhesin responsive disease, including but not limited to, a detectable impact on the rate of recovery from disease (e.g., rate of weight gain), or the reduction of at least one of the symptoms normally associated with the particular disease (e.g., if the antibody or immunoadhesin responsive disease were Crohn's disease, a reduction in at least one of the following symptoms: abdominal pain, diarrhea, rectal bleeding, weight loss, fever, loss of appetite, dehydration, anemia, distention, fibrosis, inflamed intestines and malnutrition).

Monoclonal Antibodies and Receptors

A full-length antibody ("Immunoglobulin" or "Ig") as it exists naturally is an immunoglobulin molecule comprised of four peptide chains, two heavy (H) chains (about 50-70 kDa when full length) and two light (L) chains (about 25 kDa when full length) interconnected by disulfide bonds. The amino terminal portion of each chain includes a variable region of about 100-110 or more amino acids primarily responsible for antigen recognition. The carboxy-terminal portion of each chain defines a constant region primarily responsible for effector function.

Light chains are classified as kappa or lambda and characterized by a particular constant region. Heavy chains are classified as gamma, mu, alpha, delta, or epsilon, and define the antibody's isotype as IgG, IgM, IgA, IgD, and IgE, respectively. Each heavy chain type is characterized by a particular constant region.

Each heavy chain is comprised of a heavy chain variable region (herein "HCVR") and a heavy chain constant region. The heavy chain constant region is comprised of three domains (CH1, CH2, and CH3) for IgG, IgD, and IgA; and 4 domains (CH1, CH2, CH3, and CH4) for IgM and IgE. Each light chain is comprised of a light chain variable region (herein "LCVR") and a light chain constant region. The light chain constant region is comprised of one domain, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. The assignment of amino acids to each domain is in accordance with well-known conventions [e.g., Kabat, "Sequences of Proteins of Immunological Interest," National Institutes of Health, Bethesda, Md. (1991)]. The functional ability of an antibody to bind a particular antigen is determined collectively by the six CDRs. However, even a single variable domain comprising only three CDRs specific for an antigen may have the ability to recognize and bind antigen, although at a lower affinity than a complete Fab.

Monoclonal antibodies of the invention can be produced using e.g., hybridoma techniques well known in the art, as well as recombinant technologies, phage display technologies, synthetic technologies or combinations of such technologies readily known in the art. The term "monoclonal antibody" as used herein is not limited to antibodies produced through hybridoma technology. "Monoclonal antibody" refers to an antibody that is derived from a single copy or clone, including e.g., any eukaryotic, prokaryotic, or phage clone, and not the method by which it is produced. A "monoclonal antibody" can be an intact (complete or full length) antibody, a substantially intact antibody, a functional fragment of an antibody, or it may be a chimeric antibody, human antibody, or humanized antibody.

A population of "monoclonal antibodies," refers to a homogeneous or substantially homogeneous (or pure) antibody population (i.e., at least about 90%, 91%, 92%, 93%, 94%, 95%, 96%, more preferably at least about 97% or 98% or most preferably at least 99% of the antibodies in the population are identical and would compete in an ELISA assay for the same antigen or epitope.

The term "specifically binds" or "preferentially binds" as used herein refers to the situation in which one member of a specific binding pair does not significantly bind to molecules other than its specific binding partner(s). The term is also applicable where e.g., an antigen-binding domain of an antibody of the invention is specific for a particular epitope that is carried by a number of antigens, in which case the specific antibody carrying the antigen-binding domain will be able to bind to the various antigens carrying the epitope.

The Fc region refers to the portion of an intact antibody, e.g., IgG, generated by digestion with the enzyme papain (see FIG. 1). The Fc region is a homodimer with each chain being comprised of a portion of the hinge region as well as the CH2 and CH3 domains. The Fc region is a dimer due to interchain disulfide bridges formed between the hinge regions and multiple non-covalent bonds between the CH3 domains. IgG is the most abundant class of Ig in the body, constituting approximately 75% of the total immunoglobulin and distributed equally within the intravascular and extravasular pools. Very little IgG is produced during the early stages of the primary response to antigen but is the major form of antibody produced during the secondary response.

As described above, antibodies have regions, primarily the CH2 and CH3 regions, that are involved in non-antigen binding functions. Together, these regions and a portion of the linker sequence are generally known as the Fc region, and have several effector functions mediated by binding of effector molecules.

The effector functions mediated by the antibody Fc region can be divided into two categories: (1) effector functions that operate after the binding of antibody to an antigen (these functions involve, for example, the participation of the complement cascade or Fc receptor (FcR)-bearing cells); and (2) effector functions that operate independently of antigen binding (these functions confer, for example, persistence in the circulation and the ability to be transferred across cellular barriers by transcytosis). For example, binding of the Clq component of complement to antibodies activates the complement system. Following opsonization, activation of complement is important in the lysis of cell pathogens. The activation of complement also stimulates the inflammatory response and may also be involved in autoimmune hypersensitivity. Further, antibodies bind to cells via the Fc region, with an Fc receptor binding site on the antibody Fc region binding to a FcR on a cell. There are a number of FcRs which are specific for different classes of antibody, including IgG, IgE, IgA and IgM. While the present invention is not limited to any particular mechanism, binding of antibody to FcR on cell surfaces triggers a number of important and diverse biological responses including engulfinent and destruction of antibody-coated particles, clearance of immune complexes, lysis of antibody-coated target cells by killer cells (ADCC), release of inflammatory mediators, placental transfer and control of immunoglobulin production.

Several antibody effector functions are mediated by FcRs, which bind the Fc region of an antibody. FcRs are defined by their specificity for immunoglobulin isotypes; Fc receptors for IgG antibodies are referred to as FcγR, for IgE as FceR, for IgA as FcαR and so on. Three subclasses of FcγR have been identified: FcγRI (CD64), FcγRII (CD32) and FcγRIII (CD16).

Because each FcγR subclass is encoded by two or three genes, and alternative RNA splicing leads to multiple transcripts, a broad diversity in FcγR isoforms exists. The three genes encoding the FcγRI subclass (FcγRIA, FcγRIB and FcγRIC) are clustered in region 1q21.1 of the long arm of chromosome 1; the genes encoding FcγRII isoforms (FcγRIIA, Fcγ7RB and FcγRIIC) and the two genes encoding FcγRIII (FcγRIIIA and FcγRIIIB) are all clustered in region 1q22. These different FcR subtypes are expressed on different cell types (e.g., Ravetch and Kinet, Annu. Rev. Immunol. 9: 457-492 (1991)). For example, in humans, FcγRIIIB is found only on neutrophils, whereas FcγRIIIA is found on macrophages, monocytes, NK cells, and a subpopulation of T-cells. Notably, FcγRIIIA is present on NK cells, one of the cell types implicated in ADCC.

Human FcγRIIIA (CD16) receptor has a common polymorphism at position 158 in its extracellular domain encoding either a phenylalanine or valine at this position. The V allele of FcγRIIIA has higher affinity to human IgG1 than the F allele. The V158 allele also mediates ADCC more efficiently. Clinical data have shown a correlation between the genotype of FcγRIIIA receptor in patients undergoing Rituxan treatment and therapeutic response. Both clinical and molecular responses and time to progression were shown to be superior in patients homozygous for the FcγRIIIA-158V genotype (approximately 20% of population). In contrast, patients heterozygous or homozygous for the lower affinity FcγRIIIA-158F genotype (approximately 80% of population) respond more poorly. These data suggest that Fc mutations that enhance ADCC activity of the 158F carriers might enhance the clinical efficacy of antibody-based therapy of cancer. A genetic polymorphism is also present in human FcγRIIA (CD32) receptor at position 131 in its extracellular domain encoding either a histidine (H) or arginine (R) at this position. The polymorphism at position 131 has been found to affect its ability to bind to human IgG. Recent data also show a correlation between the FcγRIIA position 131 polymorphism and clinical response to Rituxan. Patients homozygous for the Hl31 allele had a significantly higher response rate than the other 2 groups.

FcγRI, FcγRII and FcγRIII are immunoglobulin superfamily (IgSF) receptors; FcγRI has three IgSF domains in its extracellular domain, while FcγRII and FcγRIII have only two IgSF domains in their extracellular domains. Another type of Fc receptor is the neonatal Fc receptor (FcRn). FcRn is structurally similar to major histocompatibility complex (MHC) and consists of an α-chain noncovalently bound to β2-microglobulin.

Variant Fc Regions

The present invention provides variant polypeptides, nucleic acid sequences encoding the variant polypeptides, and methods for generating variant polypeptides. Preferably, the variant polypeptides of the present invention differ from a parent polypeptide by at least one amino acid modification, preferably an amino acid substitution. A "parent", "wild type", "starting" or "nonvariant" polypeptide preferably comprises at least a portion of an antibody Fc region and the amino acid substitution in the variant polypeptide occurs within the Fc region. A parent polypeptide comprising an Fc region may be prepared using techniques available in the art for generating polypeptides comprising an Fc region or portion thereof. In preferred embodiments, the parent polypeptide is an antibody. However, the parent polypeptide may be any other polypeptide comprising at least a portion of an Fc region (e.g., an immunoadhesin). The portion of Fc region in the parent polypeptide may be of a native or non-native sequence, preferably it is a native sequence of human origin. In certain embodiments, a variant Fc region may be generated (e.g., according to the methods disclosed herein) and can be fused to a heterologous polypeptide of choice, such as an antibody variable domain or binding domain of a receptor or ligand, or any therapeutic polypeptide.

In preferred embodiments, the parent polypeptide comprises an Fc region or functional portion thereof. Generally, the Fc region of the parent polypeptide will comprise a native sequence Fc region, and preferably a human native sequence Fc region. However, the Fc region of the parent polypeptide may have one or more pre-existing amino acid sequence alterations or modifications (e.g., an amino acid substitution) from a native sequence Fc region. For example, the Clq binding activity of the Fc region may have been previously altered or the FcγR binding affinity of the Fc region may have been altered. The desired variant Fc region or nucleic acid encoding the variant Fc region of interest may be constructed while not operably attached to the desired fusion partner of the variant Fc region, (e.g., an antibody variable region, a heterologous protein) and then subsequently engineered to be operably attached thereto. In further embodiments, the parent polypeptide Fc region is conceptual (e.g., mental thought or a visual representation on a computer or on paper) and, while it does not physically exist, the antibody engineer may decide upon a desired variant Fc region amino acid sequence and generate a polypeptide comprising that sequence or a DNA encoding the desired variant Fc region amino acid sequence. However, in preferred embodiments, a nucleic acid encoding an Fc region of a parent polypeptide is available and this nucleic acid sequence is altered to generate a variant nucleic acid sequence encoding the variant Fc region.

Nucleic acid encoding a variant of the parent polypeptide (or simply a variant Fc region) may be prepared by methods known in the art using the guidance of the present specification for particular sequences. These methods include, but are not limited to, preparation by site-directed (or oligonucleotide-mediated) mutagenesis, PCR mutagenesis (e.g., Vallette et al., Nuc. Acids Res. 17:723-733 (1989), and cassette mutagenesis (e.g., Wells et al., Gene 34:315-323 (1985) of an earlier prepared nucleic acid encoding the polypeptide. Site-directed mutagenesis is a preferred method for preparing variants. This technique is well known in the alt (see, e.g., Carter et al. Nucleic Acids Res. 13: 4431-4443 (1985) and Kunkel et. al., Proc. Natl. Acad. Sci. USA 82: 488 (1987)).

Alternatively, or additionally, the desired amino acid sequence encoding a variant polypeptide can be determined, and a nucleic acid sequence encoding such amino acid sequence of the variant polypeptide (i.e., polypeptide comprising a variant Fc region comprising an amino acid substitution as described herein) can be generated synthetically. This is still considered to be a variant Fc region of a parent Fc region even though the parent Fc region was not the molecular precursor of the variant Fc region but was instead the amino acid sequence of the Fc region present in the parent in the absence of the desired amino acid substitution.

The amino acid sequence of the parent polypeptide may be modified in order to generate a variant Fc region with altered Fc receptor binding affinity or activity in vitro and/or in vivo; and/or altered ADCC activity in vitro and/or in vivo; and/or altered CDC activity in vitro and/or in vivo. The amino acid sequence of the parent polypeptide may also be modified in order to generate a variant Fc region with altered complement binding properties and/or circulation half-life.

Substantial modifications in the biological properties of the Fc region may be accomplished by selecting amino acid substitutions that differ significantly in their effect on altering (a) the structure of the polypeptide backbone in the area of the substitution, for example, as a sheet or helical conformation, (b) the charge or hydrophobicity of the molecule at the target site, or the bulk of the side chain, (d) interaction with carbohydrate, or (e) flexibility of domain movement. Naturally occurring residues are divided into classes based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for a member of another class. Conservative substitutions will entail exchanging a member of one of these classes for another member of the same class.

As is demonstrated in the Examples below, one can engineer a variant Fc region with altered activity (effector function(s) and/or pharmacokinetics). One may, for example, modify one or more amino acid residues of the Fc region in order to alter (e.g., increase or decrease) ADCC activity or CDC activity or FcRn binding affinity. In preferred embodiments, a modification is a substitution as listed in Table 1 herein. Generally, one will make an amino acid substitution at one or more of the Fc region residues identified herein as effecting ADCC activity in order to generate such a variant Fc region. In preferred embodiments, no more than one to about ten Fc region residues will be substituted. The Fc regions herein comprising one or more amino acid substitutions will preferably retain at least about 80%, and preferably at least about 90%, and most preferably at least about 95%, of the parent Fc region sequence or of a native human Fc region sequence.

By introducing the appropriate amino acid sequence modification(s) in a parent Fc region, one can generate a variant Fc region which (when compared to the parent Fc region) (a) mediates ADCC in the presence of human effector cells more or less effectively and/or (b) mediates CDC in the presence of human complement more or less effectively and/or (c) binds Clq with a desired affinity and/or (d) binds an Fc gamma receptor (FcγR) or Fc neonatal receptor (FcRn) with a desired affinity. Such variant Fc regions will generally comprise at least one amino acid modification in the Fc region. Preferably the modification is an amino acid substitution, more preferably an amino acid substitution as listed in Tables 1-9 herein.

In preferred embodiments, the parent polypeptide Fc region is a human Fc region or functional fragment thereof, e.g., a native human Fc region human IgG1 (f and a,z allotypes), IgG2, IgG3, IgG4, and all allotypes known or discovered from any species. Such regions have native sequences such as, e.g., those shown in FIG. 2 (SEQ ID NOs:1-8), and FIG. 3 (SEQ ID NOs:9-12) herein.

In certain embodiments, in order to generate a variant Fc region with enhanced ADCC activity, the parent polypeptide preferably has pre-existing ADCC activity (e.g., the parent polypeptide comprises a human IgG1 or human IgG3 Fc region). In some embodiments, a variant has enhanced ADCC activity (e.g., greater levels as compared to the parent according to an ADCC assay described herein) as compared to the parent polypeptide, i.e., a monoclonal antibody comprising the variant Fc region has enhanced ADCC activity as compared under identical circumstances to a monoclonal antibody comprising the parent Fc region or a native IgG1 or IgG3 Fc region sequence but otherwise identical to the monoclonal antibody comprising the variant Fc region.

In preferred embodiments, amino acid substitution(s) are introduced into the CH2 and/or CH3 domains of a Fc region. In preferred embodiments, the parent Fc region used as the template to generate such variants comprises a human IgG Fc region.

In certain embodiments, in order to generate a variant Fc region with enhanced CDC activity, the parent polypeptide preferably has pre-existing CDC activity. In some embodiments, a variant has enhanced CDC activity (e.g., greater levels as compared to the parent according to an CDC assay described herein) as compared to the parent polypeptide, i.e., a monoclonal antibody comprising the variant Fc region has enhanced CDC activity as compared under identical circumstances to a monoclonal antibody comprising the parent Fc region or a native IgG1 or IgG3 Fc region sequence but otherwise identical to the monoclonal antibody comprising the variant Fc region.

The variant polypeptides described herein may be subjected to further modifications, depending on the desired or intended use of the polypeptide. Such modifications may involve, for example, further alteration of the amino acid sequence (substitution, insertion and/or deletion of amino acid residues), carbohydrate modifications, fusion to heterologous polypeptide(s) and/or covalent modifications. Such further modifications may be made prior to, simultaneously with, or following, the amino acid modification(s) disclosed herein which result in an alteration of Fc receptor binding and/or ADCC activity and/or CDC activity.

Alternatively or additionally, it may be useful to combine amino acid modifications with one or more further amino acid modifications that alter Clq binding and/or CDC function of the Fc region. For example, the starting polypeptide may be unable to bind Clq and/or mediate CDC and may be modified according to the teachings herein such that it acquires these further effector functions. Moreover, polypeptides with pre-existing Clq binding activity, optionally further having the ability to mediate CDC, may be modified such that one or both of these activities are enhanced (or alternatively, are diminished). Certain Fc region amino acid modifications that alter Clq binding and/or modify CDC activity are described herein (see Tables 2, 7, 8 and 10) and, for example, in W00042072.

As disclosed above, one can design an Fc region or portion thereof with altered effector function, e.g., by modifying CDC activity and/or ADCC activity. For example, one can generate a variant Fc region with improved CDC activity and improved ADCC activity. Alternatively, where one desires that an effector function be reduced or ablated, one may engineer a variant Fc region with reduced CDC activity and/or reduced ADCC activity. In other embodiments, one may increase only one of these activities, and optionally also reduce the other activity, e.g., to generate a variant Fc region with improved ADCC activity, but reduced CDC activity and vice versa. Additionally, one can engineer a variant Fc region with modified binding affinity to FcRn, protein A, and/or other Fc binding proteins.

In some embodiments, the present invention provides compositions comprising a variant of a parent polypeptide, wherein the parent comprises an Fc region (or portion thereof) and wherein the variant comprises at least one surface residue amino acid modification within the Fc region (see, e.g., Deisenhofer, Biochemistry, 20:2361-70, April 1981, and W00042072). In other embodiments, the present invention provides compositions comprising a variant of a parent polypeptide having an Fc region, wherein the variant comprises at least one non-surface residue amino acid modification in the Fc region. In further embodiments, the present invention comprises a variant of a parent polypeptide having an Fc region, wherein the variant comprises at least one surface amino acid modification and at least one non-surface amino acid modification, both in the Fc region.

Combination Variants

In some embodiments, a variant Fc region of the present invention comprises two or more amino acid modifications (e.g., substitutions). Such combination variants may be produced, for example, by selecting two or more of the amino acid substitutions detailed above (e.g., see Table 1), or one or more amino acid substitutions as listed in Table 1 in addition to a substitution known in art.

The combination variants shown in Table 10 and other combination variants (such as those substitutions disclosed in W00042072 uses in combination with those disclosed herein) may be tested for a given activity (e.g., FcRn binding activity, ADCC activity, and CDC activity) in a variety of assays (see examples below). In this regard, useful combination variants may be identified.

In certain preferred embodiments, the multiple amino acid substitutions present in a variant Fc region of the present invention has one amino acid substitution that increases ADCC activity, and one amino acid modification that increases neonatal Fc receptor (FcRn) binding affinity (e.g., at pH 6.0) of the polypeptide comprising the variant Fc region. In other embodiments, the combination variants of the present invention have one surface amino acid in a variant Fc region of the present invention, and one non-surface amino acid modification. Additional combination variants in the variant Fc regions of the present invention may be generated by combining two or more of the amino acid substitutions described herein, or at least one of the amino acid substitutions described herein with those described in e.g., W00042072.

Variant Polypeptide Assays

The present invention provides various assays for screening variant Fc regions or polypeptides comprising a variant Fc region of the invention. Screening assays may be used to find or confirm useful variants. For example, combination variants (see, e.g., Table 10) may be screened to find variants with altered FcR binding, and/or altered ADCC and/or altered CDC activity (e.g., increased or decreased ADCC or CDC activity) and/or modified ability to deplete target cells (B cells, for eg.) from whole blood. Also, as described below, the assays of the present invention may be employed to find or confirm variants that have beneficial therapeutic activity in a subject (e.g., such as a human with symptoms of an antibody or immunoadhesin responsive disease). A variety of assay types may be employed to evaluate any change in a variant compared to the parent polypeptide (screening assays provided e.g., in W00042072). Further exemplary assays are described below.

In preferred embodiments, a variant polypeptide (i.e., polypeptide comprising a variant Fc region of the present invention or functional portion thereof) is a monoclonal antibody that essentially retains the ability to specifically bind an antigen (via an unmodified antigen binding region or modified antigen binding region) as compared to the parent polypeptide (e.g., the binding capability is preferably less than 20 fold, 10 fold, 7 fold, or less than about 5 fold different than that of the parent polypeptide). The binding capability of the variant polypeptide to antigen may be determined using techniques such as ELISA, fluorescence activated cell sorting (FACS) analysis, or radioimmunoprecipitation (RIA), for example FcR binding assays may be employed to evaluate the variants of the present invention. For example, binding of Fc receptors such as FcγRI, FcγRIIa, FcγRIIb, FcγRIII, FcRn, etc., can be measured by titrating a variant polypeptide and measuring bound variant polypeptide using an antibody which binds to the variant polypeptide in an ELISA format (see Examples below). For example, a variant that comprises an antibody may be screened in a standard ELISA assay to determine binding to an FcRn at pH 6.0 and pH 7.0 or pH 7.4. A solid surface coated with streptavidin or neutravidin may be used to capture biotin labeled FcRn from any species, such as mouse or human. After blocking, the capture receptor can be incubated with variant polypeptides (e.g., antibodies) diluted in buffers at pH 6.0 or pH 7.0. In the following step a molecule specific for human antibodies is added (e.g., goat (Fab')$_2$ anti-human-Fab conjugated to an enzyme). Thereafter a substrate may be added in order to determine the amount of binding of the variant polypeptide to the immobilized FcRn at pH 6.0 or pH 7.0 or pH 7.4. The results of this assay can be compared to the parent (non-variant) polypeptide's ability to bind the same FcR. In other preferred embodiments, the components for carrying out an ELISA (e.g., with FcRn) to screen variants are packaged in a kit (e.g., with instructions for use).

An ADCC assay may also be employed to screen the variants of the present invention. ADCC assays may be performed in vitro or in vivo. To assess ADCC activity of a variant polypeptide an in vitro ADCC assay may be performed using varying effector:target ratios. An exemplary ADCC assay could use a target cell line expressing any of the following target antigens: CD20, CD22, CD33, CD40, CD63, EGF receptor, her-2 receptor, prostate-specific membrane antigen, Lewis Y carbohydrate, GD2 and GD3 gangliosides, lamp-i, CO-029, L6, and ephA2. Effector cells may be obtained from a healthy donor (e.g., on the day of the experiment) and PBMC purified using Histopaque (Sigma). Target cells are then preincubated with an IgG comprising a variant Fc region of the invention at, for example, 0.1-1,000 ng/ml for about 30 minutes prior to mixing with effector cells at effector:target ratios of, for example, 40:1, 20:1 and 10:1. ADCC activity may then be measured colorimetrically using a Cytotoxicity Detection Kit (Roche Molecular Biochemicals) for the quantitation of cell death and lysis based upon the measurement of lactate dehydrogenase (LDH) activity released from the cytosol of damaged cells into the supernatant. ADCC activity may also be measured, for Chromium loaded target cell assays, by measuring the resulting Chromium 51 released. Antibody independent cellular cytotoxicity can be determined by measuring the LDH activity from target and effector cells in the absence of antibody. Total release may be measured following the addition of 1% Triton X-100 to the mixture of target and effector cells. Incubation of the target and effector cells may be performed for an optimized period of time (0.54-18 hours) at 37° C. in 5.0% $CO_2$ and then be followed by centrifugation of the assay plates. The supernatants may then be transferred to 96 well plates and incubated with LDH detection reagent for 30 minutes at 25° C. The sample absorbance may then be measured at 490 nm using a microplate reader. The percent cytotoxicity can then be calculated using the following equation: % cytotoxicity=experimental value−low control/high control−low control×100%. The percent cytotoxicity of anti-CD20 and variants can then be compared directly with equal amount of RITUXAN to provide a measurement of relative effectiveness. An exemplary ADCC assay could employ SKW6.4 cells over-expressing the CD20 antigen (e.g., purchased from the American Type Culture Collection) as the source of target cells. Many variations of this assay are known in the art (e.g., Zuckerman et al., *CRC Crit Rev Microbiol* 1978; 7(1):1-26).

Useful effector cells for such assays include, but are not limited to, NK cells, macrophages, and other PBMC. Alternatively, or additionally, ADCC activity of the variant polypeptides of the present invention may be assessed in vivo, e.g., in a animal model such as that disclosed in Clynes et al. PNAS (USA) 95:652-656 (1998)).

The variants of the present invention may also be screened for complement activation. To assess complement activation, a CDC assay may be performed (See, e.g., Gazzano-Santoro et al., J. Immunol. Methods, 202:163 (1996)). For example, various concentrations of the variant polypeptide and human complement may be diluted with buffer. Cells which express the antigen to which the variant polypeptide binds may be diluted to a density of 1×10$^6$ cells/ml. Mixtures of variant polypeptide, diluted human complement and cells expressing the antigen may be added to a flat bottom tissue culture 96 well plate and allowed to incubate for 2 hours at 37° C. and 5% $CO_2$ to facilitate complement mediated cell lysis. Fifty microliters of alamar blue (Accumed International) may then be added to each well and incubated overnight at 37° C. The absorbance may be measured using a 96-well fluorimeter with excitation at 530 nm and emission at 590 nm. The results may be expressed in relative fluorescence units (RFU). The sample concentrations may be computed from a standard curve and the percent activity as compared to nonvariant polypeptide may be reported for the variant polypeptide of interest.

In certain embodiments, variant polypeptides of the present invention do not activate complement or activate complement poorly. For example, a variant polypeptide displays about 0-10% CDC activity in this assay compared to a control antibody having a nonmutated IgG1 Fc region. Preferably the variant does not appear to have any CDC activity (e.g., above background) in the above CDC assay. In other embodiments, a variant polypeptide of the present invention is found to have enhanced CDC compared to a parent polypeptide (e.g., preferably displaying about 1.1, 1.5, 1.7, or 2-fold to about 100-fold (or greater) enhancement in CDC activity in vitro or in vivo when the $IC_{50}$ values are compared).

Variant polypeptides of the present invention may also be screened for depletion of target cells in a whole blood assay. For example, various concentrations of the variant polypeptide with CD20 target specificity can be screened for the depletion of B cells in a whole blood assay using facs (Vugmeyster et al., 2003 Cytometry 52A, 101-109). Freshly drawn blood is incubated with varying concentrations of variant polypeptide at 37° C. and 5% $CO_2$ for 4 hours (time can be varied). Following the incubation, red blood cells are lysed per manufacturer's directions with an ammonium chloride reagent (Beckton-Dickinson cat.#555899) and B cells are detected by facs using a fluorescent-labeled antibody specific for B cells (anti-CD 19, for example). The results may be expressed as percent depletion of B cells relative to either an untreated sample or a sample incubated with an irrelevant (non-depleting) antibody.

In preferred embodiments, a variant polypeptide depletes B cells more effectively than the parental polypeptide. A variant polypeptide may deplete B cells, for example, to about two-fold or greater extent than the parent polypeptide, and preferably about five-fold or more. Also, a variant may display greater potency in depleting B cells. For example, a variant may deplete the same percentage of B cells relative to parental polypeptide, but utilize about five-fold less, and preferably about 10-fold less antibody. Target cell depletion mediated by variants may be about 2-fold, 3-fold, 5-fold to about 1000-fold or greater, and preferably from about 5-fold to about 1000-fold improved compared to the parent polypeptide.

The variants of the present invention may also be screened in vivo. Any type of in vivo assay may be employed. A particular example of one type of assay is provided below. This exemplary assay allows for preclinical evaluation of Fc variants in vivo. A variant to be tested may be incorporated into the Fc region of a particular antibody known to have some activity. For example, a variant may be incorporated into the Fc region of an anti-CD20 IgG by mutagenesis. This allows a parental IgG and Fc variant IgG to be compared directly with RITUXAN (known to promote tumor regression). The preclinical evaluation may be done in 2 phases (a pharmacokinetic and pharmacodynamic phase). The goal of the Phase I pharmacokinetic studies is to determine if there are differences in the clearance rate between an Fc variant IgG and the antibody with known in vivo activity (e.g., RITUXAN). Differences in clearance rate may cause differences in the steady-state level of IgG in serum. As such, if differences in steady-state concentrations are detected these should be normalized to enable accurate comparisons to be made. The goal of the Phase II pharmacodynamic studies is to determine the effect of the Fc mutations upon, in this case, tumor growth. Previous studies with RITUXAN used a single dose which completely inhibited tumor growth. Because this does not allow quantitative differences to be measured, a dose range should be employed.

Phase I pharmacokinetic comparison of an Fc variant, the wild type parental Fc, and RITUXAN may be performed, e.g., in the following manner. First, 40 µg (or other dose to be tested) per animal may be injected intravenously and the plasma level of the IgG quantitated at 0, 0.25, 0.5, 1, 24, 48, 72, 96, 120, 168, and 336 hrs. The data may be fitted, for example, using a pharmacokinetic program (WinNonLin) using a zero lag two compartment pharmacokinetic model to obtain the clearance rate. Clearance rate may be used to define steady state plasma level with the following equation: C=Dose/(Clearance rate×t), where T is the interval between doses and C is the plasma level at steady state. Pharmacokinetic experiments may be performed in non-tumor bearing mice with, for example, a minimum of 5 mice per time point.

An exemplary animal model may be employed for the next phase in the following manner. The right flank of CB17-SCID mice may be implanted with $10^6$ Raji cells subcutaneously. Intravenous bolus of the variant Fc antibody, the wild type Fc antibody, and RITUXAN may be commenced immediately after implantation and continued until the tumor size is greater than 2 cm in diameter. Tumor volume may be determined every Monday, Wednesday and Friday by measuring the length, width, and depth of the tumor using a caliper (tumor volume=W×L×D). A plot of tumor volume versus time will give the tumor growth rate for the pharmacodynamic calculation. A minimum of about 10 animals per group should be used.

Phase II pharmacodynamic comparison of the variant Fc antibody, the wild type Fc antibody, and RITUXAN may be performed in the following manner. Based on published data, RITUXAN at 10 µg/g weekly completely inhibited tumor growth in vivo (Clynes et al., Nat. Med. 6:443-6, 2000). Therefore, a weekly dose range of 10 µg/g, 5 µg/g, 1 µg/g, 0.5 µg/g, and 0 µg/g may be tested. The steady state plasma level at which tumor growth rate is inhibited by 50% may be graphically determined by the relationship between steady state plasma level and effectiveness. The steady state plasma level may be calculated as described above. If necessary, τ may be adjusted accordingly for each variant Fc antibody and the wild type Fc antibody depending on their pharmacokinetic properties to achieve comparable steady state plasma level as RITUXAN. Statistical improved pharmakodynamic values of the variant Fc antibody in comparison to the parental polypeptide (e.g., wild type Fc antibody) and RITUXAN will generally indicate that the variant Fc antibody confers improved activity in vivo.

Additional pharmacodynamic comparison of variant Fc antibodies, wild type Fc antibodies, and RITUXAN may be performed in cynomolgus monkeys as described previously (Reff et al., Blood 83, 435-445, 1994). A dose response for depletion of peripheral B cells and lymph node B cells may be used to compare the relative potencies of the Fc variants with wild type Fc and RITUXAN administered intravenously and/or subcutaneously. Statistical improved pharmacodynamic values of the Fc variant in comparison to the parental polypeptide (e.g., Fc wild type) and RITUXAN will generally indicate that the variant Fc antibody confers improved activity in vivo.

In further embodiments, the variants (i.e., polypeptide comprising a variant Fc region of the invention, or functional portion thereof) of the present invention are screened such that variants that are useful for therapeutic use in at least two species are identified. Such variants are referred to herein as "dual-species improved variants", and are particularly useful for identifying variants that are therapeutic in humans, and also demonstrate (or are likely to demonstrate) efficacy in an animal model. In this regard, the present invention provides methods for identifying variants that have a strong chance of being approved for human clinical testing since animal model data will likely support any human testing applications made to governmental regulatory agencies (e.g., U.S. Food and Drug Administration).

In certain embodiments, dual-species improved variants are identified by first performing an ADCC assay using human effector cells to find improved variants, and then performing a second ADCC assay using mouse, rat, or non-human primate effector cells to identify a sub-set of the improved variants that are dual-species improved variants. In some embodiments, the present invention provides methods for identifying dual-species improved variants, comprising: a) providing: i) target cells, ii) a composition comprising a candidate variant of a parent polypeptide having at least a portion of an Fc region, wherein the candidate variant comprises at least one amino acid substitution in the Fc region, and wherein the candidate variant mediates target cell cytotoxicity in the presence of a first species (e.g., human) of effector cells more effectively than the parent polypeptide, and iii) second species (e.g., mouse, rat, or non-human primate) effector cells, and b) incubating the composition with the target cells under conditions such that the candidate variant binds the target cells thereby generating candidate variant bound target cells, c) mixing the second species effector cells with the candidate variant bound target cells, and d) measuring target cell cytotoxicity mediated by the candidate variant.

In certain embodiments, the method further comprises step e) determining if the candidate variant mediates target cell cytotoxicity in the presence of the second species effector cells more effectively than the parent polypeptide. In some embodiments, the method further comprises step f) identifying a candidate variant as a dual-species improved variant that mediates target cell cytotoxicity in the presence of the second species effector cells more effectively than the parent polypeptide. In preferred embodiments, the dual-species variants identified are then screened in vivo in one or more animal assays.

In certain embodiments, dual-species improved variants are identified by first performing a whole blood assay using human blood to find improved variants, and then performing a second whole blood assay using mouse, rat, or non-human primate blood to identify a sub-set of the improved variants that are dual-species improved variants. In some embodiments, the present invention provides methods for identifying dual-species improved variants, comprising: a) providing: i) target cells, ii) a composition comprising a candidate variant of a parent polypeptide having at least a portion of an Fc region, wherein the candidate variant comprises at least one amino acid substitution in the Fc region, and wherein the candidate variant mediates target cell depletion in the presence of a first species (e.g., human) blood more effectively than the parent polypeptide, and iii) second species (e.g., mouse, rat, or non-human primate) blood, and b) incubating the composition with the target cells under conditions such that the candidate variant binds the target cells thereby generating candidate variant bound target cells, c) mixing the second species blood with the candidate variant bound target cells, and d) measuring target cell depletion mediated by the candidate variant. In certain embodiments, the method further comprises step e) determining if the candidate variant mediates target cell depletion in the presence of the second species blood more effectively than the parent polypeptide. In some embodiments, the method further comprises step f) identifying a candidate variant as a dual-species improved variant that mediates target cell depletion in the presence of the second species blood more effectively than the parent polypeptide. In preferred embodiments, the dual-species variants identified are then screened in vivo in one or more animal assays.

In certain embodiments, dual-species improved variants are identified by performing any of the assays above using human components (e.g., human cells, human FcR, etc.) to identify improved variants, and then running the same assay (or a different assay) with non-human animal components (e.g., mouse cells, mouse FcR, etc.). In this regard, a sub-set of variants that perform well according to a given criteria in both human based assays and a second species based assays can be identified.

An exemplary process for identifying dual-species improved variants is as follows. First, a nucleic acid sequence encoding at least a portion of an IgG Fc region is mutated such that the amino acid sequence expressed has at least one amino acid change, thereby generating a variant. This expressed IgG variant is then characterized in an ADCC assay using human PBMCs or a subset (NK cells or macrophages, for example). If enhanced ADCC activity is found, then the variant is screened in a second ADCC assay using mouse or rat PBMCs. Alternatively, or in addition, an assay can be performed with the variant for binding to cloned rodent receptors or cell lines. Finally, if the variant is found to be improved in the second assay, making it a dual-improved variant, then the variant is screened in vivo in mice or rats.

Exemplary Variant Fc Region Containing Molecules

The variant Fc regions of the present invention may be part of larger molecules. The larger molecules may be, for example, monoclonal antibodies, polyclonal antibodies, chimeric antibodies, humanized antibodies, bispecific antibodies, immunoadhesins, etc. Additionally, a variant Fc region of the invention may be operably attached to a non-antibody polypeptide upon which it may confer an altered (increased or decreased) half life. As such, it is evident that there is a broad range of applications for the variant Fc regions of the present invention.

Antibodies Containing Variant Fc Regions

In preferred embodiments, the variant Fc region containing molecule (e.g., polypeptide) is an antibody. Techniques for producing antibodies are described below.

(i) Antigen Selection and Preparation

Generally, when the variant Fc region containing molecule is an antibody, the antibody is directed against an antigen of interest. Preferably, the antigen is a polypeptide and administration of the antibody to a mammal suffering from a disease or disorder which would benefit from a decrease in amount or activity of the antigenic molecule can result in a therapeutic benefit in that mammal. However, antibodies directed against nonpolypeptide antigens (such as tumor associated glycolipid antigens; see U.S. Pat. No. 5,091,178), may also be employed.

Exemplary antigens include, but are not limited to, molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3,-4,-5, or -6 (NT-3, NT-4, NT-5, or NT-6), or a nerve growth factor; platelet-derived growth factor (PDGF); fibroblast growth factor such as a FGF and, FGF; epidermal growth factor (EGF); transforming growth factor (TGF) such as TGF-alpha and TGF beta, including TGF-1, TGF-2, TGF-3, TGF-4, or TGF-5; insulin-like growth factor-I and -I1 (IGF-I and IGF-II); des (1-3)-IGF-I (brain 1GF-I), insulin-like growth factor binding proteins; CD proteins such as CD3, CD4, CD8, CD19 and CD20; erythropoietin; osteoinductive factors; immunotoxins; a bone morphogenetic protein (BMP); a growth differentiation factor (e.g., GDF8); an interferon such as interferon-alpha,-beta, and -gamma; colony stimulating factors (CSFs), e.g., M-CSF, GM-CSF, and G-CSF; interleukins (ILs), e.g., IL-1 to IL-25; superoxide dismutase; T-25 cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA4 and VCAM; a tumor associated antigen such as HER2, HER3 or HER4 receptor; ghrelin; a member of an apoptosis pathway; and fragments or precursors of any of the above-listed polypeptides.

Preferred antigens include, but are not limited to, CD proteins such as CD3, CD4, CD8, CD19, CD20 and CD34; members of the ErbB receptor family such as the EGF receptor, HER2, HER3 or HER4 receptor; cell adhesion molecules such as LFA-1, Mac1, p 150.95, VLA-4, ICAM-1, VCAM, a4/p7 integrin, and (Xv/p3 integrin including either a 5 or subunits thereof (e.g., anti-CDIIa, anti-CD18 or anti-CD11b antibodies); growth factors such as VEGF; tissue factor (TF); alpha interferon (α-IFN); growth differentiation factors, e.g., GDF-8; an interleukin, such as IL-8; IgE; blood group antigens; flk2/flt3 receptor; obesity (OB) receptor; mpl receptor; CTLA-4; protein C and ghrelin.

Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule. Other antigens and forms thereof useful for preparing antibodies will be apparent to those in the art.

(ii) Polyclonal Antibodies

The present invention provides polyclonal antibodies with variant Fc regions. For example, a human immunoglobulin repertoire containing modified IgG1 constant regions may be transplanted into immunoglobulin-inactivated mice, resulting in mice expressing an IgG repertoire containing modified Fc regions (see, e.g., Mendez, M J et al., Nature Genetics 15:146 (1997)). Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized (e.g., keyhole limpet hemocyanin, serum albumin, bovine thyroglobulin, or soybean tyrpsin inhibitor) using a bifunctional or derivitizing agent (e.g., maleimidobenzoyl sulfosuccinimide ester for conjugation through cystein residues, N-hydroxysuccinimide for conjugation through lysine residues, glutaraldehyde, succinic anhydride, SOC12, or R1N=C=NR, where R and R1 are different alkyl groups.

Examples of a general immunization protocol for a rabbit and mouse are as follows. Animals are immunized against the antigen, immunogenic conjugates, or derivatives by combining, for example, 100 µg or 5 µg of the protein or conjugate (e.g., for a rabbit or mouse respectively) with 3 volumes of Freund's complete adjuvant and injecting the solution intradermally at multiple sites. One month later the animals are boosted with ⅕ or ⅒ the original amount of peptide or conjugate in Freund's complete adjuvant by subcutaneous injection at multiple sites. Seven to fourteen days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. In addition, aggregating agents such as alum are suitably used to enhance the immune response.

(iii) Monoclonal Antibodies

The present invention provides monoclonal antibodies with variant Fc regions. Monoclonal antibodies may be made in a number of ways, including using the hybridoma method (e.g., as described by Kohler et al., Nature, 256: 495, 1975), or by recombinant DNA methods (e.g., U.S. Pat. No. 4,816,567).

In the hybridoma method, a mouse or other appropriate host animal, such as a hamster or macaque monkey, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-1 I mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (e.g., Kozbor, J. Immunol., 133: 3001 (1984)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as RIA or ELISA. After hybridoma cells are identified that produce antibodies of the desired specificity, affinity, and/or activity, the clones may be subcloned by limiting dilution procedures and grown by standard methods. Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies is described in more detail below.

In some embodiments, antibodies or antibody fragments are isolated from antibody phage libraries generated using the techniques described in, for example, McCafferty et al., Nature, 348: 552554 (1990). Clackson et al., Nature, 352: 624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., BioTechnology, 10: 779-783 (1992)), as well as combinatorial infection and in vivo recombination as a strategy for constructing very large phage libraries (e.g., Waterhouse et al., Nuc. Acids. Res., 21: 2265-2266 (1993)). Thus, these techniques, and similar techniques, are viable alternatives to traditional monoclonal antibody hybridoma techniques well known in the art for isolation of monoclonal antibodies. Also, the DNA may be modified, for example, by substituting the coding sequence for human heavy- and light-chain constant domains in place of the homologous murine sequences (e.g., U.S. Pat. No. 4,816,567, and Morrison, et al., Proc. Nat. Acad. Sci. USA, 81: 6851 (1984), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iv) Humanized and Human Antibodies

The present invention provides humanized and human antibodies with variant Fc Regions of the invention. In preferred embodiments, a humanized antibody comprises human antibody amino acid sequences together with amino acid residues that are not from a human antibody. In some embodiments, the human sequences in a humanized antibody comprise the framework regions ("FRs") and the sequences or residues that are not from a human antibody comprise one or more CDRs. It is worth noting that FRs and CDRs can be defined based on amino acid residue numbering in the heavy and VL regions. The term CDR is intended to mean the non-contiguous antigen combining sites found within the variable region of both heavy and light chain polypeptides. These regions have been defined by Kabat et al. (J. Biol. Chem. 252:6609-6616 (1977) and Kabat et al. Sequences of Proteins of Immunological Interest (1991); "Kabat", Chothia et al. (J. Mol. Biol. 196:901-917 (1987); "Chothia" and MacCallum et al (J. Mol. Biol. 262:732-745 (1996); "MacCallum", where the definitions include overlapping or subsets of amino acid residues when compared against each other. Nevertheless, the application of any of these definitions, alone (for example, the Kabat definition) or in combination (by way of example only, the combined definition of Kabat and Chothia) to refer to a CDR of an antibody (including a humanized antibody) is intended to be within the scope of the term as defined and used herein.

Also, the term "framework" when used in reference to an antibody variable region is intended to mean all amino acid residues outside the CDR regions within the variable region of an antibody. Therefore, a variable region framework is between about 100-120 amino acids in length but is intended to reference only those amino acids outside of the CDRs. The term "framework region" is intended to mean each domain of the framework that is separated by the CDRs. Therefore, for the specific example of a VH region and for the CDRs as defined by Kabat, framework region 1 (FR1) corresponds to the domain of the variable region encompassing amino acids 1-30; framework region 2 (FR2) corresponds to the domain of the variable region encompassing amino acids 36-49; region 3 (FR3) corresponds to the domain of the variable region encompassing amino acids 66-94, and region 4 (FR4) corresponds to the domain of the variable region from amino acid 103 to the end of the variable region. The FRs for the light chain are similarly separated by each of the light chain variable region CDRs. Similarly, using the definition of CDRs by Chothia or MacCallum, or any combination of CDR definitions, the framework boundaries are separated by the respective CDR termini as described above. Notwithstanding the multiple definitions of CDRs, in some embodiments, it is preferred to use the Kabat definition to define CDRs.

The residues in a humanized antibody that are not from a human antibody may be residues or sequences imported from or derived from another species (including but not limited to mouse), or these sequences may be random amino acid sequences (e.g., generated from randomized nucleic acid sequences), which are inserted into the humanized antibody sequence. As noted above, the human amino acid sequences in a humanized antibody are preferably the FRs, while the residues which are not from a human antibody (whether derived from another-species or random amino acid sequences) preferably correspond to the CDRs. However, in some embodiments, one or more FRs may contain one or more non-human amino acid residues. In cases of alterations or modifications (e.g., by introduction of a non-human residue) to an otherwise human framework, it is possible for the altered or modified FR to be adjacent to a modified CDR from another species or a random CDR sequence, while in other embodiments, an altered FR is not adjacent to an altered CDR sequence from another species or a random CDR sequence. In some embodiments, the framework sequences of a humanized antibody are entirely human (i.e., no framework changes are made to the human framework). In preferred embodiments, the framework sequences of a humanized antibody are entirely human germline (i.e., no framework changes are made to the human germline framework).

Non-human amino acid residues from another species, or a random sequence, are often referred to as "import" residues, which are typically taken from an "import" variable domain. Humanization can be essentially performed following the method of Winter and co-workers (e.g., Jones et al., Nature, 321: 522-525 (1986); Riechmann et al., Nature, 332: 323-327 (1988); Verhoeyen et al., Science, 239: 1534-1536 (1988)), by substituting rodent (or other mammal) CDRs or CDR sequences for the corresponding sequences of a human antibody. Also, antibodies wherein substantially less than an intact human variable domain has been substituted by the corresponding sequence from a non-human species may also be generated (e.g., U.S. Pat. No. 4,816,567). In practice, humanized antibodies are typically human antibodies in which some CDR residues and possibly some FR residues are substituted by residues from analogous sites in rodent antibodies, or, as noted above, in which CDR sequences have been substituted by random sequences. By way of non-limiting example only, methods for conferring donor CDR binding affinity onto an antibody acceptor variable region framework are described in WO 01/27160 A1, and in U.S. patent application Ser. Nos. 09/434,870 and 09/982,464.

The choice of human variable domains, both light and heavy, to be used in making the humanized antibodies is important to reduce antigenicity. According to the so-called "best-fit" method, the sequence of the variable domain of a rodent antibody to be humanized is screened against the entire library of known human variable-domain sequences. The human sequence which is closest to that of the rodent is then accepted as the human framework (FR) for the humanized antibody (e.g., Sims et al., J. Immunol., 151: 2296 (1993), and Chothia et al., J. Mol. Biol., 196: 901 (1987)). Another method uses a particular framework derived from the consensus sequence of all human antibodies of a particular subgroup of light or heavy chains. The same framework may be used for several different humanized antibodies (e.g., Carter et al., Proc. Natl. Acad. Sci. USA, 89: 4285 (1992); Presta et al., J. Immunol., 151: 2623 (1993)).

In other embodiments, there is no need to "pre-select" a particular human antibody framework (i.e., there is no need to select a human framework with the closest homology or sequence identity to a given candidate antibody to be humanized). In these embodiments, a common or universal human framework may be used to accept one or more non-human CDRs. In the preferred embodiment, a single universal, fully human framework is used as the framework for all antibodies to be humanized, regardless of its homology to the framework sequence(s) of the candidate antibodies. In this regard, humanized antibodies may be generated without making any changes in the framework region. This universal, fully human framework can then accept one or more CDR sequences. In one embodiment, the one or more CDR sequences are CDR sequences from an antibody from another species (e.g., mouse or rat) which have been modified in comparison to the corresponding CDR in the intact antibody from the other species (i.e., there is simultaneous introduction of the CDR and modification of the CDR being introduced into the universal human framework). The modification corresponds to one or more amino acid changes (in the modified CDR) in comparison to the corresponding CDR in the intact antibody from the other species. In one embodiment, all amino acid residues in the CDR are included in a library, while in other embodiments, not all of the CDR amino acid residues are included in a library. In another embodiment, the one or more CDR sequences are random sequences, which substitute for CDR sequences.

In preferred embodiments, antibodies are humanized with retention of high affinity for the antigen and other favorable biological properties. In some embodiments, the affinity of the humanized antibody for the antigen is higher than the affinity of the corresponding non-humanized, intact antibody or fragment or portion thereof (e.g., the candidate rodent antibody). In this regard, in some embodiments, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen (s), is achieved. In general, the CDR residues are directly and most substantially involved in influencing antigen binding.

A variety of specific methods, well known to one of skill in the art, may be employed to introduce antibody CDRs (or random sequences substituting for antibody CDRs) into antibody frameworks (see, for example, U.S. application Ser. Nos. 09/434,879 and 09/982,464). In some embodiments, overlapping oligos may be used to synthesize an antibody gene, or portion thereof (for example, a gene encoding a humanized antibody). In other embodiments, mutagenesis of an antibody template may be carried out using the methods of Kunkel (infra), for example to introduce a modified CDR or a random sequence to substitute for a CDR. In some embodiments, light and heavy chain variable regions are humanized separately, and then co-expressed as a humanized variable region. In other embodiments, humanized variable regions make-up the variable region of an intact antibody. In some embodiments, the Fc region of the intact antibody comprising a humanized variable region has been modified (e.g., at least one amino acid modification has been made in the Fc region). For example, an antibody that has been humanized with randomized CDR and no framework changes may comprise at least one amino acid modification in the Fc region.

In other embodiments, transgenic animals (e.g., mice) that are capable, upon immunization, of producing a full repertoire of human antibodies in the absence of endogenous immunoglobulin production are employed. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge (See, e.g., Jakobovits et al., Proc. Natl. Acad. Sci. USA, 90: 2551 (1993), and Jakobovits et al., Nature, 362: 255-258 (1993)). Human antibodies can also be derived from phage-display libraries (e.g., Hoogenboom et al., J. Mol. Biol., 227: 381 (1991), and Vaughan et al., Nature Biotech 14: 309 (1996)).

The present invention provides methods for generating humanized antibodies (and antibody fragments) that comprise at least one amino acid substitution as listed in Table 1 herein, in the Fc region (as compared to a parental polypeptide comprising an Fc region without the amino acid substitution). Discussed below are additional methods for generating such humanized antibodies. The present invention also provides compositions comprising the antibodies and antibody fragments generated by these methods. Importantly, the humanization methods discussed below, and other humanization methods (e.g., discussed above), may be combined with the variant Fc regions of the present invention. In this regard, humanized antibodies with altered, unique Fc regions may be constructed according to the present invention.

In some embodiments, a method of constructing a population of altered VH region encoding nucleic acids is provided, comprising: a) providing a representation of first and second reference amino acid sequences, the first reference sequence comprising the sequence of a donor VH region, the donor variable region comprising i) FRs and ii) three CDRs as defined by the combined definitions of Kabat and Chothia; the second reference sequence comprising the sequence of an acceptor VH region comprising FRs; b) synthesizing first oligonucleotides encoding portions of the FRs of the acceptor VH region, wherein the portions of the FRs when compared to the second reference sequence are unmodified; and a population of second oligonucleotides, each encoding i) at least a portion of a first CDR that has been modified, the first CDR selected from the group consisting of HCDR1, HCDR2 and HCDR3, wherein the modified first CDR comprises a different amino acid at one or more positions when compared to the corresponding donor CDRs of the first reference sequence and ii) one or more portions of unmodified FRs which are capable of hybridizing to the first oligonucleotides; c) mixing the first oligonucleotides with the population of second oligonucleotides as to create overlapping oligonucleotides; and d) treating the overlapping oligonucleotides under conditions such that a population of altered VH region encoding nucleic acids is constructed, wherein the FRs encoded by the altered VH region encoding nucleic acids are unmodified with respect to the second reference sequence.

In other embodiments, a method of constructing a population of altered VL region encoding nucleic acids is provided, comprising: a) providing a representation of first and second reference amino acid sequences, the first reference sequence comprising the sequence of a donor VL region, the donor variable region comprising i) FRs and ii) three CDRs as defined by the combined definitions of Kabat and Chothia; the second reference sequence comprising the sequence of an acceptor VL region comprising FRs; b) synthesizing first oligonucleotides encoding portions of the FRs of the acceptor VL region, wherein the portions of the FRs when compared to the second reference sequence are unmodified; and a population of second oligonucleotides, each encoding i) at least a portion of a first CDR that has been modified, the first CDR selected from the group consisting of LCDR1, LCDR2 and LCDR3, wherein the modified first CDR comprises a different amino acid at one or more positions when compared to the corresponding donor CDRs of the first reference sequence and ii) one or more portions of unmodified FRs which are capable of hybridizing to the first oligonucleotides; c) mixing the first oligonucleotides with the population of second oligonucleotides as to create overlapping oligonucleotides; and d) treating the overlapping oligonucleotides under conditions such that a population of altered VL region encoding nucleic acids is constructed, wherein the FRs encoded by the altered VL region encoding nucleic acids are unmodified with respect to the second reference sequence.

In some embodiments, a method of constructing a population of altered VH region encoding nucleic acids is contemplated, comprising: A) providing a representation of first and second reference amino acid sequences, the first reference sequence comprising the sequence of a donor VH region, the donor variable region comprising i) FRs and ii) three CDRs as defined by the combined definitions of Kabat and Chothia; the second reference sequence comprising the sequence of an acceptor VH region comprising FRs; B) synthesizing a population of first oligonucleotides, each encoding at least a portion of a first CDR selected from the group consisting of HCDR1, HCDR2 and HCDR3, wherein the modified first CDR comprises a different amino acid at one or more positions when compared to the corresponding donor CDRs of the first reference sequence; and second oligonucleotides encoding i) portions of the FRs of the acceptor VH region, wherein the portions of the FRs when compared to the reference sequence are unmodified and ii) one or more portions of a CDR which are capable of hybridizing to the population of first oligonucleotides; C) mixing the population of first oligonucleotides with the second oligonucleotides as to create overlapping oligonucleotides; and D) treating the overlapping oligonucleotides under conditions such that a population of altered VH region encoding nucleic acids is constructed, wherein the FRs encoded by the altered VH region encoding nucleic acids are unmodified with respect to the second reference sequence.

In other embodiments, a method of constructing a population of altered VL region encoding nucleic acids is provided, comprising: A) providing a representation of first and second reference amino acid sequences, the first reference sequence comprising the sequence of a donor VL region, the donor variable region comprising i) FRs and ii) three CDRs as defined by the combined definitions of Kabat and Chothia; the second reference sequence comprising the sequence of an acceptor VL region comprising FRs; B) synthesizing a) a population of first oligonucleotides, each encoding at least a portion of a first CDR selected from the group consisting of LCDR1, LCDR2 and LCDR3, wherein the modified first CDR comprises a different amino acid at one or more positions when compared to the corresponding donor CDRs of the first reference sequence; and b) second oligonucleotides encoding i) portions of the FRs of the acceptor VL region, wherein the portions of the FRs when compared to the reference sequence are unmodified and ii) one or more portions of a CDR which are capable of hybridizing to the population of first oligonucleotides; C) mixing the population of first oligonucleotides with the second oligonucleotides as to create overlapping oligonucleotides; and D) treating the overlapping oligonucleotides under conditions such that a population of altered VL region encoding nucleic acids is constructed, wherein the FRs encoded by the altered VL region encoding nucleic acids are unmodified with respect to the second reference sequence.

In some embodiments, the representation of first and second reference sequences is in electronic form. In some embodiments, the method further comprises the step of (e) coexpressing the population of altered VH region encoding nucleic acids with a light chain variable, region encoding nucleic acid so as to produce a diverse population of altered heteromeric variable regions. In some embodiments, the synthesizing comprises chemically synthesizing. In some embodiments, the acceptor is human. In some embodiments, the treating of step (d) comprises extension by a polymerase.

In other embodiments, a method of constructing a population of altered VH region encoding nucleic acids is contemplated, comprising: a) providing a representation of first and second reference amino acid sequences, the first reference sequence comprising the sequence of a donor VH region, the donor variable region comprising i) FRs and ii) three CDRs, the second reference sequence comprising a VH region; b)

synthesizing a population of altered VH region antibody gene sequences, wherein the FRs of the altered VH regions are identical to the FRs of the second reference sequence and at least a first CDR of the altered antibody variable regions has been modified, wherein the modified first CDR comprises a different amino acid at one or more positions when compared to the corresponding donor CDR of the first reference sequence.

In some embodiments, a method of constructing a population of altered VL region encoding nucleic acids is contemplated, comprising: a) providing a representation of first and second reference amino acid sequences, the first reference sequence comprising the sequence of a donor VL region, the donor variable region comprising i) FRs and ii) three CDRs; the second reference sequence comprising the sequence of an acceptor VL region comprising FRs; b) synthesizing a population of altered VL region antibody gene sequences, wherein the FRs of the altered VL regions are identical to the FRs of the second reference sequence and at least a first CDR of the altered antibody VL region has been modified, wherein the modified first CDR comprises a different amino acid at one or more positions when compared to the corresponding donor CDR of the first reference sequence.

In some embodiments, the representation of first and second reference sequences is in electronic form. In some embodiments, the method further comprises the step of coexpressing the population of altered VL region encoding nucleic acids with a VH region encoding nucleic acid so as to produce a diverse population of altered heteromeric variable regions. In some embodiments, the acceptor is human. In some embodiments, the synthesizing involves the use of overlapping oligonucleotides.

In yet other embodiments, a method of constructing a population of altered VH region encoding nucleic acids is contemplated, comprising: a) providing a representation of a reference amino acid sequence, the reference sequence comprising the sequence of an acceptor VH region comprising FRs; b) synthesizing a population of altered VH region antibody gene sequences, wherein the FRs of the altered VH regions are identical to the FRs of the reference sequence and at least a first CDR of the altered antibody variable regions comprises a random amino acid sequence.

In other embodiments, a method of constructing a population of altered VL region encoding nucleic acids is contemplated, comprising: a) providing a representation of a reference amino acid sequence, the reference sequence comprising the sequence of an acceptor VL region comprising FRs; b) synthesizing a population of altered VL region antibody gene sequences, wherein the FRs of the altered VL regions are identical to the FRs of the reference sequence and at least a first CDR of the altered antibody VL regions comprises a random amino acid sequence.

In yet other embodiments, a method of constructing a population of altered VH region encoding nucleic acids is contemplated, comprising: a) providing a representation of a reference amino acid sequence, the reference sequence comprising the sequence of a human acceptor VH region comprising FRs; b) synthesizing a population of altered VH region antibody gene sequences, wherein the FRs of the altered VH regions are identical to the FRs of the human reference sequence and at least a first CDR of the altered antibody variable regions comprises a random amino acid sequence. In some embodiments, the representation of the human reference sequence is in electronic form.

In other embodiments, a method of constructing a population of altered VL region encoding nucleic acids is contemplated, comprising: a) providing a representation of a reference amino acid sequence, the reference sequence comprising the sequence of a human acceptor VL region comprising FRs; b) synthesizing a population of altered VL region antibody gene sequences, wherein the FRs of the altered VL regions are identical to the FRs of the human reference sequence and at least a first CDR of the altered antibody VL regions comprises a random amino acid sequence.

In some embodiments, the representation of the reference sequence is in electronic form. In some embodiments, the method further comprises the step of coexpressing the population of altered VL region encoding nucleic acids with a VH region encoding nucleic acid so as to produce a diverse population of altered heteromeric variable regions. In some embodiments, the synthesizing involves the use of overlapping oligonucleotides. In some embodiments, the CDRs are defined by the Kabat definition.

In some embodiments, one or more FRs are modified simultaneously with the introduction of one or more modified CDRs. In other embodiments, the modified frameworks are adjacent to the modified CDRs.

In some embodiments, the present invention provides methods of constructing a population of altered VH region encoding nucleic acids, comprising: a) providing a representation of first and second reference amino acid sequences, the first reference amino acid sequence comprising the sequence of a donor VH region, the donor variable region comprising i) FRs and ii) three CDRs as defined by the combined definitions of Kabat and Chothia; the second reference amino acid sequence comprising the sequence of an acceptor VH region comprising FRs; b) synthesizing a) a first population of oligonucleotides, comprising oligonucleotides encoding a modified VH region FR, or portion thereof, wherein the VH region FR, or portion thereof, contains a plurality of changed amino acids at one or more positions when compared to the acceptor framework region reference sequence, wherein the framework positions that are changed are selected from among the acceptor framework positions of the second reference sequence that differ at the corresponding position compared to the donor framework positions of the first reference sequence; and b) a second population of oligonucleotides, each encoding i) at least one modified CDR, or portion thereof, wherein the modified CDR, or portion thereof, comprises a different amino acid at one or more positions when compared to the corresponding donor CDR amino acid reference sequence and ii) one or more portions of adjacent FRs which are capable of hybridizing to the first population of oligonucleotides; and c) mixing the first and second populations of oligonucleotides so as to create overlapping oligonucleotides; and d) treating the overlapping oligonucleotides under conditions such that a population of altered VH region encoding nucleic acids is constructed. In certain embodiments, the representation of first and second reference sequences is in electronic form. In other embodiments, the methods further comprise the step of (e) coexpressing the population of altered VH region encoding nucleic acids with a VL region encoding nucleic acid so as to produce a diverse population of altered heteromeric variable regions. In additional embodiments, the synthesizing comprises chemically synthesizing. In some embodiments, the acceptor is human. In preferred embodiments, the one or more of the diverse population of altered heteromeric variable regions are part of an antibody comprising an Fc region, wherein the Fc region comprises at least one amino acid substitution as compared to a parental polypeptide having an Fc region.

In other embodiments, the present invention provides methods of constructing a population of altered VL region encoding nucleic acids, comprising: a) providing a representation of first and second reference amino acid sequences, the first reference amino acid sequence comprising the sequence of a donor VL region, the donor variable region comprising i) FRs and ii) three CDRs as defined by the combined definitions of Kabat and Chothia; the second reference amino acid sequence comprising the sequence of an acceptor VL region comprising FRs; b) synthesizing a) a first population of oligonucleotides, comprising oligonucleotides encoding a modified VL region FR, or portion thereof, wherein the VL region framework region, or portion thereof, contains a plurality of changed amino acids at one or more positions when compared to the acceptor framework region reference sequence, wherein the framework positions that are changed are selected from among the acceptor framework positions of the second reference sequence that differ at the corresponding position compared to the donor framework positions of the first reference sequence; and b) a second population of oligonucleotides, each encoding i) at least one modified CDR, or portion thereof, wherein the modified CDR, or portion thereof, comprises a different amino acid at one or more positions when compared to the corresponding donor CDR amino acid reference sequence and ii) one or more portions of adjacent FRs which are capable of hybridizing to the first population of oligonucleotides; and c) mixing the first and second populations of oligonucleotides so as to create overlapping oligonucleotides; and d) treating the overlapping oligonucleotides under conditions such that a population of altered VL region encoding nucleic acids is constructed. In other embodiments, the representation of first and second reference sequences is in electronic form. In additional embodiments, the methods further comprise the step of (e) coexpressing the population of altered VL region encoding nucleic acids with a heavy chain variable region encoding nucleic acid so as to produce a diverse population of altered heteromeric variable regions.

In some embodiments, the methods comprise a) providing a representation of first and second reference amino acid sequences, the first reference amino acid sequence comprising the sequence of a donor VH region, the donor variable region comprising i) FRs and ii) three CDRs as defined by the combined definitions of Kabat and Chothia; the second reference amino acid sequence comprising the sequence of an acceptor VH region comprising FRs; b) synthesizing a) a first population of oligonucleotides, comprising oligonucleotides encoding a modified VH region framework region, or portion thereof, wherein the VH region FR, or portion thereof, contains a plurality of changed amino acids at one or more positions when compared to the acceptor FR reference sequence wherein the framework positions that are changed are selected from among the acceptor framework positions of the second reference sequence that differ at the corresponding position compared to the donor framework positions of the first reference sequence; and b) a second population of oligonucleotides, each encoding i) at least one modified CDR, or portion thereof, wherein the modified CDR, or portion thereof, comprises a different amino acid at one or more positions when compared to the corresponding donor CDR amino acid reference sequence and ii) one or more portions of adjacent FRs which are capable of hybridizing to the first population of oligonucleotides; and c) mixing the first and second populations of oligonucleotides so as to create overlapping oligonucleotides; and d) extending the overlapping oligonucleotides with a DNA polymerase under conditions such that a population of altered VH region encoding nucleic acids is constructed.

In still other embodiments, the present invention provides methods of constructing a population of altered VL region encoding nucleic acids, comprising: a) providing a representation of first and second reference amino acid sequences, the first reference amino acid sequence comprising the sequence of a donor VL region, the donor variable region comprising i) FRs and ii) three CDRs as defined by the combined definitions of Kabat and Chothia; the second reference amino acid sequence comprising the sequence of an acceptor VL region comprising FRs; b) synthesizing a) a first population of oligonucleotides, comprising oligonucleotides encoding a modified VL region FR, or portion thereof, wherein the VL region FR, or portion thereof, contains a plurality of changed amino acids at one or more positions when compared to the acceptor FR reference sequence, wherein the framework positions that are changed are selected from among the acceptor framework positions of the second reference sequence that differ at the corresponding position compared to the donor framework positions of the first reference sequence; and b) a second population of oligonucleotides, each encoding i) at least one modified CDR, or portion thereof, wherein the modified CDR, or portion thereof, comprises a different amino acid at one or more positions when compared to the corresponding donor CDR amino acid reference sequence and ii) one or more portions of adjacent FRs which are capable of hybridizing to the first population of oligonucleotides; and c) mixing the first and second populations of oligonucleotides so as to create overlapping oligonucleotides; and d) extending the overlapping oligonucleotides with a DNA polymerase under conditions such that a population of altered VL region encoding nucleic acids is constructed.

In some embodiments, one or more modifications are introduced into the framework, simultaneously with the introduction of one or more modified CDRs. The modified CDRs may comprise one or more amino acid alterations in comparison with the corresponding CDR of a reference sequence. In certain embodiments, the methods of constructing a population of altered VH region encoding nucleic acids, comprises: a) providing a representation of first and second reference amino acid sequences, the first reference amino acid sequence comprising the sequence of a donor VH region, the donor variable region comprising i) FRs and ii) three CDRs as defined by the combined definitions of Kabat and Chothia; the second reference amino acid sequence comprising the sequence of an acceptor VH region comprising FRs; b) synthesizing i) a first population of oligonucleotides, each encoding at least one modified CDR, wherein the modified CDR comprises a different amino acid at one or more positions when compared to the corresponding donor CDR amino acid reference sequence; and ii) a second population of oligonucleotides, comprising oligonucleotides encoding modified portions of a VH region framework, the modified portion containing a plurality of changed amino acids at one or more positions when compared to the acceptor framework region reference sequence, wherein the framework positions that are changed are selected from among the acceptor framework positions of the second reference sequence that differ at the corresponding position compared to the donor framework positions of the first reference sequence; c) mixing the first and second populations of oligonucleotides under conditions such that at least a portion of the oligonucleotides hybridize so as to create overlapping oligonucleotides; and d) treating the overlapping oligonucleotides under conditions such that a population of altered VH region encoding nucleic acids is constructed. In certain embodiments, the representation of first and second reference sequences is in electronic form. In further embodiments, the methods further comprise the step of (e) coexpressing the population of altered VH region encoding nucleic acids with a VL region encoding nucleic acid so as to produce a diverse population of altered heteromeric variable regions. In other embodiments, the acceptor is human.

In other embodiments, the present invention provides methods constructing a population of altered VL region encoding nucleic acids, comprising: a) providing a representation of first and second reference amino acid sequences, the first reference amino acid sequence comprising the sequence of a donor VL region, the donor variable region comprising i) FRs and ii) three CDRs as defined by the combined definitions of Kabat and Chothia; the second reference amino acid sequence comprising the sequence of an acceptor VL region comprising FRs; b) synthesizing i) a first population of oligonucleotides, each encoding at least one modified CDR, wherein the modified CDR comprises a different amino acid at one or more positions when compared to the corresponding donor CDR amino acid reference sequence; and ii) a second population of oligonucleotides, comprising oligonucleotides encoding modified portions of a VL region framework, the modified portion containing a plurality of changed amino acids at one or more positions when compared to the acceptor FR reference sequence, wherein the framework positions that are changed are selected from among the acceptor framework positions of the second reference sequence that differ at the corresponding position compared to the donor framework positions of the first reference sequence; c) mixing the first and second populations of oligonucleotides under conditions such that at least a portion of the oligonucleotides hybridize so as to create overlapping oligonucleotides; and d) treating the overlapping oligonucleotides under conditions such that a population of altered VL region encoding nucleic acids is constructed.

In certain embodiments, the antibodies or antibody fragments comprising an Fc variant and an altered heavy chain variant region may be generated. For example, in some embodiments, the present invention provides methods of constructing a population of altered VH region encoding nucleic acids, comprising: a) providing a representation of first and second reference amino acid sequences, the first reference sequence comprising the sequence of a donor VH region, the donor variable region comprising i) FRs and ii) three CDRs as defined by the combined definitions of Kabat and Chothia; the second reference sequence comprising the sequence of an acceptor VH region comprising FRs; b) synthesizing A) first oligonucleotides encoding portions of the FRs of the acceptor VH region, wherein the portions of the FRs when compared to the second reference sequence are unmodified; and B) a population of second oligonucleotides, each encoding i) at least a portion of a first CDR that has been modified, the first CDR selected from the group consisting of HCDR1, HCDR2 and HCDR3, wherein the modified first CDR comprises a different amino acid at one or more positions when compared to the corresponding donor CDRs of the first reference sequence and ii) one or more portions of unmodified FRs which are capable of hybridizing to the first oligonucleotides; c) mixing the first oligonucleotides with the population of second oligonucleotides as to create overlapping oligonucleotides; and d) treating the overlapping oligonucleotides under conditions such that a population of altered VH region encoding nucleic acids is constructed, wherein the FRs encoded by the altered VH region encoding nucleic acids are unmodified with respect to the second reference sequence. In some embodiments, the methods further comprise the step of coexpressing the population of altered VH region encoding nucleic acids with a VL region encoding nucleic acid so as to produce a diverse population of altered heteromeric variable regions.

In other embodiments, the present invention provides methods of constructing a population of altered VL region encoding nucleic acids, comprising: a) providing a representation of first and second reference amino acid sequences, the first reference sequence comprising the sequence of a donor VL region, the donor variable region comprising i) FRs and ii) three CDRs as defined by the combined definitions of Kabat and Chothia; the second reference sequence comprising the sequence of an acceptor VL region comprising FRs b) synthesizing a) first oligonucleotides encoding portions of the FRs of the acceptor VL region, wherein the portions of the FRs when compared to the second reference sequence are unmodified; and b) a population of second oligonucleotides, each encoding i) at least a portion of a first CDR that has been modified, the first CDR selected from the group consisting of LCDR1, LCDR2 and LCDR3, wherein the modified first CDR comprises a different amino acid at one or more positions when compared to the corresponding donor CDRs of the first reference sequence and ii) one or more portions of unmodified FRs which are capable of hybridizing to the first oligonucleotides; c) mixing the first oligonucleotides with the population of second oligonucleotides as to create overlapping oligonucleotides; and d) treating the overlapping oligonucleotides under conditions such that a population of altered VL region encoding nucleic acids is constructed, wherein the FRs encoded by the altered VL region encoding nucleic acids are unmodified with respect to the second reference sequence.

In other embodiments, the present invention provides methods of constructing a population of altered VH region encoding nucleic acids, comprising: A) providing a representation of first and second reference amino acid sequences, the first reference sequence comprising the sequence of a donor VH region, the donor variable region comprising i) FRs and ii) three CDRs as defined by the combined definitions of Kabat and Chothia; the second reference sequence comprising the sequence of an acceptor VH region comprising FRs; B) synthesizing a) a population of first oligonucleotides, each encoding at least a portion of a first CDR selected from the group consisting of HCDR1, HCDR2 and HCDR3, wherein the modified first CDR comprises a different amino acid at one or more positions when compared to the corresponding donor CDRs of the first reference sequence; and b) second oligonucleotides encoding i) portions of the FRs of the acceptor VH region, wherein the portions of the FRs when compared to the reference sequence are unmodified and ii) one or more portions of a CDR which are capable of hybridizing to the population of first oligonucleotides; C) mixing the population of first oligonucleotides with the second oligonucleotides as to create overlapping oligonucleotides; and D) treating the overlapping oligonucleotides under conditions such that a population of altered VH region encoding nucleic acids is constructed, wherein the FRs encoded by the altered VH region encoding nucleic acids are unmodified with respect to the second reference sequence.

In certain embodiments, the methods further comprise the step of coexpressing the population of altered VH region encoding nucleic acids with a VL region encoding nucleic acid so as to produce a diverse population of altered heteromeric variable regions.

In other embodiments, the present invention provides methods of constructing a population of altered VL region encoding nucleic acids, comprising: A) providing a representation of first and second reference amino acid sequences, the first reference sequence comprising the sequence of a donor VL region, the donor variable region comprising i) FRs and ii) three CDRs as defined by the combined definitions of Kabat and Chothia; the second reference sequence comprising the sequence of an acceptor VL region comprising FRs; B) synthesizing a) a population of first oligonucleotides, each encoding at least a portion of a first CDR selected from the group consisting of LCDR1, LCDR2 and LCDR3, wherein the modified first CDR comprises a different amino acid at one or more positions when compared to the corresponding donor CDRs of the first reference sequence; and b) second oligonucleotides encoding i) portions of the FRs of the acceptor VL region, wherein the portions of the FRs when compared to the reference sequence are unmodified and ii) one or more portions of a CDR which are capable of hybridizing to the population of first oligonucleotides; C) mixing the population of first oligonucleotides with the second oligonucleotides as to create overlapping oligonucleotides; and D) treating the overlapping oligonucleotides under conditions such that a population of altered VL region encoding nucleic acids is constructed, wherein the FRs encoded by the altered VL region encoding nucleic acids are unmodified with respect to the second reference sequence.

In other embodiments, the present invention provides methods of improving the binding affinity of a mutated humanized antibody variable region, comprising: a) providing a nucleic acid sequence encoding a first mutated humanized antibody variable region, the mutated variable region comprising (i) a wild type human antibody framework, (ii) three non-human heavy chain CDRs, and (iii) three non-human light chain CDRs, wherein the CDRs are defined by the combined definitions of Kabat and Chothia, wherein at least one of the light chain CDRs is a mutation-containing light chain CDR at least one different amino acid at least one position when compared to the corresponding wild type non-human CDR, and wherein the first mutated antibody variable region has a higher binding affinity than the corresponding non-mutated antibody variable region; b) mutating the nucleic acid sequence encoding the first mutated antibody variable region under conditions such that a second mutated humanized antibody variable region is encoded, the second mutated humanized antibody variable region comprising at least one additional different amino acid at least one position in the mutation-containing light chain CDR, the additional mutation in combination with the first mutation resulting in higher binding affinity. In some embodiments, the mutation-containing light chain CDR of the first mutated humanized antibody variable region is CDR3 (LCDR3).

In other embodiments, at least one of the non-human heavy chain CDRs of the first mutated humanized antibody variable region comprises a mutation, such that a different amino acid is encoded at least one position when compared to the corresponding wild type non-human CDR. In additional embodiments, the heavy chain CDR mutation is in HCDR3.

In some embodiments, the present invention provides methods of simultaneously modifying at least one CDR and at least one FR while constructing a population of altered VH region encoding nucleic acids, comprising: a) providing a representation of first and second reference amino acid sequences, the first reference amino acid sequence comprising the sequence of a donor VH region, the donor variable region comprising i) four FRs and ii) three CDRs as defined by the combined definitions of Kabat and Chothia; the second reference amino acid sequence comprising the sequence of an acceptor VH region comprising four FRs, as defined by the combined definitions of Kabat and Chothia; b) synthesizing i) for every FR to be modified, a population of oligonucleotides, each encoding a modified FR, or portion thereof, the modified FR or portion thereof, containing a plurality of changed amino acids at one or more positions when compared to the corresponding framework region in the acceptor VH region reference sequence, wherein the FR positions that are changed are selected from among the acceptor framework positions of the second reference sequence that differ at the corresponding position compared to the donor framework region positions of the first reference sequence; and ii) for every CDR to be modified, a population of oligonucleotides, each encoding a modified CDR, or portion thereof, wherein the modified CDR comprises a different amino acid at one or more positions when compared to the corresponding donor CDR amino acid reference sequence; and iii) for each of any remaining and unmodified FRs, oligonucleotides encoding the FR, or portion thereof, having the same sequence as the corresponding FR of the second reference acceptor sequence; and iv) for each of any remaining and unmodified CDRs, oligonucleotides encoding the CDR, or portion thereof, having the same sequence as the corresponding CDR of the first reference donor sequence, wherein, individual oligonucleotides from (i) through (iv) which encode adjacent portions of the VH region have overlapping sequences at their termini; and c) mixing the oligonucleotides and populations of oligonucleotides synthesized in step b) under conditions such that the overlapping sequences of individual oligonucleotides hybridize so as to create overlapping oligonucleotides; and d) treating the overlapping oligonucleotides under conditions such that a population of altered VH region encoding nucleotides is formed. In certain embodiments, the representation of first and second reference sequences is in electronic form. In further embodiments, the framework region to be modified is selected from the group consisting of HFR1, HFR2 and HFR3. In other embodiments, the CDR to be modified is HCDR3. In other embodiments, the method further comprises the step of e) coexpressing the population of VH region encoding nucleic acids with a VL region encoding nucleic acid so as to produce a diverse population of altered heteromeric variable regions. In different embodiments, the method further comprises the step of e) coexpressing the population of VH region encoding nucleic acids with a population of VL region encoding nucleic acids so as to produce a diverse population of altered heteromeric variable regions.

In other embodiments, the methods of simultaneously modifying at least one CDR and at least one FR while constructing a population of altered VL region encoding nucleic acids are employed, wherein said method comprises: a) providing a representation of first and second reference amino acid sequences, the first reference amino acid sequence comprising the sequence of a donor VL region, the donor variable region comprising i) four FRs and ii) three CDRs as defined by the combined definitions of Kabat and Chothia; the second reference amino acid sequence comprising the sequence of an acceptor VL region comprising four FRs, as defined by the combined definitions of Kabat and Chothia; b) synthesizing i) for every FR to be modified, a population of oligonucleotides, each encoding a modified FR, or portion thereof, the modified FR, or portion thereof, containing a plurality of changed amino acids at one or more positions when compared to the corresponding framework region in the acceptor VL region reference sequence, wherein the FR positions that are changed are selected from among the acceptor FR positions of the second reference sequence that differ at the corresponding position compared to the donor FR positions of the first reference sequence; and ii) for every CDR to be modified, a population of oligonucleotides, each encoding a modified CDR, or portion thereof, wherein the modified CDR comprises a different amino acid at one or more positions when compared to the corresponding donor CDR amino acid reference sequence; and iii) for each of any remaining and unmodified FR regions, oligonucleotides encoding the FR, or portion thereof, having the same sequence as the corresponding FR of the second reference acceptor sequence; and iv) for each of any remaining and unmodified CDRs, oligonucleotides encoding the CDR, or portion thereof, having the same sequence as the corresponding CDR of the first reference donor sequence, wherein, individual oligonucleotides from (i) through (iv) which encode adjacent portions of the VL region have overlapping sequences at their termini, and c) mixing the oligonucleotides and populations of oligonucleotides synthesized in step b) under conditions such that the overlapping sequences of individual oligonucleotides hybridize so as to create overlapping oligonucleotides; and d) treating the overlapping oligonucleotides under conditions such that a population of altered VL region encoding nucleotides is formed. In certain embodiments, the methods further comprise the step of coexpressing the population of VL region encoding nucleic acids with a population of VH region encoding nucleic acids so as to produce a diverse population of altered heteromeric variable regions.

(v) Multispecific Antibodies

The present invention provides multispecific antibodies comprising a variant Fc region. Multispecific antibodies have binding specificities for at least two different antigens. While such molecules normally will only bind two antigens (i.e., bispecific antibodies, BsAbs), antibodies with additional specificities such as trispecific antibodies are encompassed by this expression when used herein. Examples of BsAbs include, but are not limited to, those with one arm directed against a tumor cell antigen and the other arm directed against a cytotoxic trigger molecule such as anti-FcγRI/anti-CD 15, anti-pl 85HER2/FcγRIII (CD16), anti-CD3/anti-malignant B-cell (D1D0), anti-CD3/antipl 85HER2, anti-CD3/anti-p97, anti-CD3/anti-renal cell carcinoma, anti-CD3/anti-OVCAR-3, antiCD3/L-D I (anti-colon carcinoma), anti-CD3/anti-melanocyte stimulating hornone analog, anti EGF receptor/anti-CD3, anti-CD3/anti-CAMAI, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-id-1, antiCD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcool); BsAbs which can be used as fibrinolytic agents such as anti-fibrin/anti-tissue plasminogen activator (tPA), anti-fibrin/antiurokinase-type plasminogen activator (uPA); BsAbs for targeting immune complexes to cell surface receptors such as anti-low density lipoprotein (LDL)/anti-FcR (e.g., FcγRI, FcγRII or FcγRIII); BsAbs for use in therapy of infectious diseases such as anti-CD3/anti-herpes simplex virus (HSV), anti-T-cell receptor: CD3 complex/anti-influenza, anti-FcγR/anti-HIV; BsAbs for tumor detection in vitro or in vivo such as anti-CEA/anti-EOTUBE, anti-CEA/anti-DPTA, anti-pl 85HER2/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-p-galactosidase.

Examples of trispecific antibodies include, but are not limited to, anti-CD3/anti-CD4/anti-CD37, anti-CD3/anti-CD5/ anti-CD37 and anti-CD3/anti-CD8/anti-CD37. Bispecific antibodies can be prepared as full length antibodies or antibody fragments (e.g., F(ab')$_2$ bispecific antibodies). Methods for making bispecific antibodies are known in the art. Traditional production of full length bispecific antibodies is based on the coexpression of two immunoglobulin heavy chain-light chain pairs, where the two chains have different specificities (e.g., Millstein et al., Nature, 305: 537-539 (1983)). Because of the random assortment of immunoglobulin heavy and light chains, these hybridomas (quadromas) produce a potential mixture of ten different antibody molecules, of which only one has the correct bispecific structure. Purification of the correct molecule may be performed by affinity chromatography steps. Similar procedures are disclosed in WO 93/08829, and Traunecker et al., EMBO J., 10: 3655-3659 (1991).

In another approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH 1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm (see, e.g., WO 94/04690). According to another approach described in W096/27011 the interface between a pair of antibody molecules can be engineered to maximize the percentage of heterodimers which are recovered from recombinant cell culture. specific antibodies also include cross-linked or "heteroconjugate" antibodies. For example, one of the antibodies in the heteroconjugate can be coupled to avidin, the other to biotin.

B. Immunoadhesin Molecules

The present invention also provides immunoadhesin molecules comprising a variant Fc region. One type of immunoadhesin design combines the binding domain(s) of the adhesin (e.g., the extracellular domain (ECD) of a receptor) with the Fc region of an immunoglobulin heavy chain (e.g., a variant Fc region). Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion, or binding characteristics of the immunoadhesin.

In some embodiments, the adhesin sequence is fused to the N-terminus of the variant Fc region of immunoglobulin G1. It is possible to fuse the entire heavy chain constant region to the adhesin sequence. However, in preferred embodiments, a sequence beginning in the hinge region just upstream of the papain cleavage site which defines IgG Fc chemically (i.e., residue 216, taking the first residue of heavy chain constant region to be 114), or analogous sites of other immunoglobulins is used in the fusion. In certain preferred embodiments, the adhesin amino acid sequence is fused to (a) the hinge region and CH2 and CH3 or (b) the CH1, hinge, CH2 and CH3 domains, of an IgG heavy chain. In some embodiments, the immunoadhesins are bispecific. Alternatively, the adhesin sequences can be inserted between immunoglobulin heavy chain and light chain sequences, such that an immunoglobulin comprising a chimeric heavy chain is obtained. In such embodiments, the adhesin sequences may be fused to the 3' end of an immunoglobulin heavy chain in each arm of an immunoglobulin, either between the hinge and the CH2 domain, or between the CH2 and CH3 domains (see, e.g., Hoogenboom et al., Mol. Immunol. 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567.

In preferred embodiments, immunoadhesins are constructed by fusing the cDNA sequence encoding the adhesin portion in-frame to an immunoglobulin cDNA sequence. However, fusion to genomic immunoglobulin fragments can also be used. Generally, the latter type of fusion requires the presence of Ig regulatory sequences for expression. cDNAs encoding IgG heavy chain constant regions can be isolated based on published sequences from cDNA libraries derived from spleen or peripheral blood lymphocytes, by hybridization or by PCR techniques. The cDNAs encoding the "adhesin" and the immunoglobulin parts of the immunoadhesin may be inserted in tandem into a plasmid vector that directs efficient expression in the chosen host cells.

Altered Half Life of Variant Polypeptides

The neonatal Fc receptor "FcRn" is a major histocompatibility complex (MHC) homolog which not only delivers IgGs across the maternofetal barrier during gestation, but is also involved in the regulation of IgG serum half life. For a recent FcRn review see Ghetie, V and E. S. Ward, Annu. Rev. Immunol. 18:739-766, 2000. FcRn binds to IgG in a pH-dependent manner with binding occurring at slightly acidic pHs and little or no detectable binding at pH 7.4. It is postulated that IgGs are taken up by FcRn-expressing cells and enter acidic endosomes where the FcRn-IgG interaction occurs. Then the IgGs are transported to the cell surface and released at near neutral pH. IgGs that do not bind FcRn after uptake into cells enter lysosomal compartments and are degraded. Consistent with this model is the hypothesis that polypeptides comprising a variant Fc region which binds to FcRn with increased affinity has a longer serum half life than those with a lesser affinity.

The role of FcRn as an IgG transporter indicates that variant Fc regions with altered affinity to FcRn may have therapeutic utility either in the context of a monoclonal antibody or when operably attached to a heterologous protein, i.e., a non-antibody. Therapeutic polypeptides which would benefit by being cleared quickly from the subject or patient or by not being transported across a placental membrane, e.g., radiolabeled polypeptides, would benefit by being operably attached to an Fc region which displays diminished FcRn binding affinity. Alternatively, polypeptides which would benefit from having a longer serum half life and therefore need to be administered fewer times or by being transported across a placental membrane would preferentially be operably attached to an Fc region which displays enhanced FcRn binding affinity (see Tables 2, 5 and 6). Numerous combinations of Fc characteristics are contemplated, e.g., an Fc region with enhanced FcRn binding affinity but with little or no CDC or ADCC activity may be generated by incorporating one or more Fc amino acid substitutions which enhance FcRn binding affinity as listed in Table 2 into e.g., an IgG4 parent Fc region, or into an IgG1 parent Fc region in combination with amino acid substitution that diminish CDC and ADCC activity.

Preferred polypeptides which would benefit from an increased serum half life by being operably attached to a variant Fc region of the invention which displays enhanced FcRn binding affinity as compared to the parent polypeptide are mammalian therapeutic polypeptides including molecules such as, e.g., renin; a growth hormone; human growth hormone; bovine growth hormone; growth hormone releasing factor; ghrelin; parathyroid hormone; thyroid stimulating hormone; lipoprotein; insulin A-chain; insulin B-chain; $\alpha$1-antitrypsin; PAI-1; proinsulin; thrombopoietin; follicle stimulating hormone; calcitonin; luteinizing hormone; glucagons; clotting factors such as factor VIIIC, factor IX, tissue factor, and von Willdebrands factor; anti-clotting factors such as Protein C; atrial naturietic factor; lung surfactant; a plaminogen activator, such as urokinase or human urine or tissue-type plasminogen activator (t-PA); bombesin; thrombin; hemopoietic growth factor; interleukins, e.g., IL-1 to IL-10, IL-20; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; Dnase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-S, or NT-6), or a nerve growth factor such as NGF-beta, cardiotrophins (cardiac hypertrophy factor) such as cardiotrophin-1 (CT-1); platelet-derived growth factor (PDGR); fibroblast growth factor such as aFGF and bFGF, epidermal growth factor (EGF) or its receptor; transforming growth factor (TGF) such as TGF-alpha and TGF-beta, including TGF-$\beta$1, TGF-$\beta$2, TGF-$\beta$3, TGF-$\beta$4 or TGF-$\beta$5; insulin-like growth factor-I and -II; des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein, a growth differentiation factor (e.g., GDF-8); an interferon such as interferon-alpha, -beta, and -gamma; colony stimulating factors (CSFs), e.g, M-CSF; GM-CSF; and G-CSF; an anti-HER-2 antibody without a native Fc region of an IgG; an anti-RSV antibody without a native Fc region of an IgG; superoxide dismutase; T-cell receptors; surface membrane proteins; decay accelerating factor; viral antigen such as, for example, a portion of the HIV-1 envelop; transport protein; homing receptors; addressins; regulatory proteins; antibodies without a native Fc region of an IgG; and fragments or precursors of any of the above-listed polypeptides.

The variant Fc region comprising an amino acid substitution of the invention which confers an altered serum half-life on the polypeptide (i.e., enhanced FcRn binding affinity) to which it is operably attached is preferably operably attached to the carboxy- or amino-terminus of the polypeptide of interest thereby generating a fusion protein.

Nucleic Acid Sequences Encoding Variant Fc Regions

The present invention also provides nucleic acid sequences encoding variant Fc regions, as well as compositions, vectors, and host cells comprising nucleic acid sequences encoding variant Fc regions. The present invention also provides recombinant methods for producing variant Fc region.

Generally, for recombinant production of variants, nucleic acid encoding the variant is isolated and inserted into a vector. Host cells may be transfected with the vector, thereby allowing the nucleic acid sequence to be amplified, and/or the variant peptide produced. Nucleic acid sequences encoding the peptide variants of the present invention may be isolated and sequenced using conventional procedures (e.g., using oligonucleotide probes that are capable of binding specifically to nucleic acid encoding the variant). Generally, the nucleic acid sequence encoding the variant is operably linked to other elements, such as a signal sequence (e.g., secretory signal sequences), an origin of replication, at least one marker gene, an enhancer, a promoter, or a transcription terminator. In certain embodiments, host cells are stably transfected with nucleic acid encoding a variant to generate a cell line expressing a particular variant. In preferred embodiments, the variants are expressed in CHO, NS0, Sp2/0, PER.C6, or HEK293 cells. Recombinant methods are well known in the art.

Nucleic acid sequences may be mutated such that variant Fc regions may be produced. For example, a nucleic acid sequence encoding a parental Fc region (e.g., SEQ ID NOs: 1-12) may be mutated such that at least one amino acid change results when the nucleic acid sequence is expressed. Also, nucleic acid sequences encoding at least a portion of a parental Fc region may be mutated to produce amino acid sequences comprising at least a portion of a variant Fc region.

In certain embodiments, codon-based synthesis is employed to generate mutated sequences. Examples of codon-based synthesis include, for example, those described in U.S. Pat. Nos. 5,264,563, 5,523,388 and 5,808,022. Briefly, codon-based synthesis may be performed by sequentially coupling monomers on separate supports to form at least two different tuplets. The coupling may be performed in separate reaction vessels, then mixing the supports from the reaction vessels, and dividing the mixed supports into two or more separate reaction vessels, and repeating the coupling, mixing and dividing steps one or more times in the reaction vessels, ending with a mixing or dividing step. Additionally, the oligonucleotides can be cleaved from the supports.

Therapeutic Uses and Formulations

In some embodiments, the present invention provides therapeutic formulations comprising the variants described herein. It is not intended that the present invention be limited by the particular nature of the therapeutic composition. For example, such compositions can include a variant polypeptide (or portion thereof), provided together with physiologically tolerable liquids, gels, solid carriers, diluents, adjuvants and excipients, and combinations thereof (See, e.g, Remington's Pharmaceutical Sciences 16th edition, Osol, A. Ed. (1980)).

In addition, variant polypeptides may be used together with, prior to, or subsequent to other therapeutic agents, including, but not limited to, salicylates, steroids, immunosuppressants, antibodies or antibiotics. Particular therapeutic agents which may be used with the variants of the present invention include, but are not limited to, the following agents azobenzene compounds (U.S. Pat. No. 4,312,806), benzyl-substituted rhodamine derivatives (U.S. Pat. No. 5,216,002), zinc L-carnosine salts (U.S. Pat. No. 5,238,931), 3-phenyl-5-carboxypyrazoles and isothiazoles (U.S. Pat. No. 5,294,630) IL-10 (U.S. Pat. No. 5,368,854), quinoline leukotriene synthesis inhibitors (U.S. Pat. No. 5,391,555), 2'-halo-2'-deoxyadenosine (U.S. Pat. No. 5,506,213), phenol and benzamide compounds (U.S. Pat. No. 5,552,439), tributyrin (U.S. Pat. No. 5,569,680), certain peptides (U.S. Pat. No. 5,756,449), omega-3 polyunsaturated acids (U.S. Pat. No. 5,792,795), VLA-4 blockers (U.S. Pat. No. 5,932,214), prednisolone metasulphobenzoate (U.S. Pat. No. 5,834,021), cytokine restraining agents (U.S. Pat. No. 5,888,969), and nicotine (U.S. Pat. No. 5,889,028).

Variant polypeptides may be used together with agents which reduce the viability or proliferative potential of a cell. Agents which reduce the viability or proliferative potential of a cell can function in a variety of ways including, for example, inhibiting DNA synthesis, inhibiting cell division, inducing apoptosis, or inducing non-apoptotic cell killing. Specific examples of cytotoxic and cytostatic agents, include but are not limited to, pokeweed antiviral protein, abrin, ricin, and each of their A chains, doxorubicin, cisplastin, iodine-131, yttrium-90, rhenium-188, bismuth-212, taxol, 5-fluorouracil VP-16, bleomycin, methotrexate, vindesine, adriamycin, vincristine, vinblastine, BCNU, mitomycin and cyclophosphamide and certain cytokines such as TNF-α and TNF-β. Thus, cytotoxic or cytostatic agents can include, for example, radionuclides, chemotherapeutic drugs, proteins, and lectins.

Therapeutic compositions may contain, for example, such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%-95% of active ingredient, preferably 2%-70% active ingredient.

The variant polypeptides of the present invention can also be mixed with diluents or excipients which are compatible and physiologically tolerable. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

In some embodiments, the therapeutic compositions of the present invention are prepared either as liquid solutions or suspensions, as sprays, or in solid forms. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%. One example of an oral composition useful for delivering the therapeutic compositions of the present invention is described in U.S. Pat. No. 5,643,602.

Additional formulations which are suitable for other modes of administration, such as topical administration, include salves, tinctures, creams, lotions, transdermal patches, and suppositories. For salves and creams, traditional binders, carriers and excipients may include, for example, polyalkylene glycols or triglycerides. One example of a topical delivery method is described in U.S. Pat. No. 5,834,016. Other liposomal delivery methods may also be employed (See, e.g., U.S. Pat. Nos. 5,851,548 and 5,711,964).

The formulations may also contain more than one active compound as necessary for the particular indication being treated, preferably those with complementary activities that do not adversely affect each other. Such molecules are suitably present in combination in amounts that are effective for the purpose intended.

Sustained-release preparations may also be prepared. Suitable examples of sustained release preparations include semipermeable matrices of solid hydrophobic polymers containing the variant polypeptide, which matrices are in the form of shaped articles, e.g., films, or microcapsule. Examples of sustained-release matrices include, but are not limited to, polyesters, hydrogels (for example, poly(2-hydroxyethylmethacrylate), or poly(vinylalcohol)), polylactides, copolymers of L-glutamic acid and γ-ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The variant polypeptides of the present invention may be used to treat a subject. Such treatment may be administered to a subject with a disease, or may be administered prophylactically to a subject (e.g., to a subject predisposed to a disease). Example of conditions that may be treated include, but are not limited to, cancer (e.g., where the variant polypeptide binds the HER2 receptor, CD20 or vascular endothelial growth factor (VEGF)); allergic conditions such as asthma (with an anti-IgE antibody); and LFA-1-mediated disorders (e.g., where the variant polypeptide is an anti-LFA-I or anti-ICAM-1 antibody) etc.

In preferred embodiments, the polypeptide variants used to treat subjects comprise antibodies or immunoadhesins. Also in preferred embodiments, the diseases treated are antibody or immunoadhesin responsive diseases. Examples of antibody responsive diseases include diseases and medical conditions such as: lymphoma (shown to be treatable with RITUXAN, an anti-CD20 antibody), infectious disease (shown to be treatable with SYNAGIS, an antibody directed to the F protein of respiratory syncytial virus), kidney transplant (ZENAPAX, an anti-IL-2 receptor antibody, has shown to be helpful), Crohn's disease and rheumatoid arthritis (shown to be treatable with REMICADE, an anti-TNFα antibody), breast carcinoma (shown to be treatable with HERCEPTIN, an anti-20 HER2 antibody), and colon cancer (shown to be treatable with EDRECOLOMAB, an anti-17-1A antibody). Variant polypeptides used for treating cancer would preferably comprise an Fc region amino acid substitution of the invention which confers enhanced ADCC activity and or enhanced CDC activity upon the polypeptide.

In some embodiments, a variant polypeptide with improved ADCC activity is employed in the treatment of diseases or disorders where destruction or elimination of tissue or foreign microorganisms is desired. For example, the variant may be used to treat cancer; inflammatory disorders; infections (e.g., bacterial, viral, fungal or yeast infections); and other conditions (such as goiter) where removal of tissue is desired. In other embodiments, the variant polypeptide has diminished ADCC activity. Such variants may be used to treat diseases or disorders where an Fc region-containing polypeptide with long half-life is desired, but the polypeptide preferably does not have undesirable effector function(s). For example, the Fc region-containing polypeptide may be an anti-tissue factor (TF) antibody; anti-IgE antibody; and anti-integrin antibody (e.g., an anti-a 437 antibody). The desired mechanism of action of such Fc region-containing polypeptides may be to block ligand-receptor binding pairs. Moreover, the Fc-region containing polypeptide with diminished ADCC activity may be an agonist antibody.

Variant polypeptides used for treating cancer would preferably comprise an Fc region amino acid substitution of the invention (see, e.g., Table 2 herein) which confers enhanced ADCC activity and or enhanced CDC activity upon the polypeptide.

The variant polypeptides of the present invention may be administered by any suitable means, including parenteral, subcutaneous, topical, intraperitoneal, intrapulmonary, and intranasal, and, intralesional administration (e.g., for local immunosuppressive treatment). Parenteral infusions include intramuscular, intravenous, intraarterial, intraperitoneal, or subcutaneous administration. In addition, the polypeptide variant is suitably administered by pulse infusion, particularly with declining doses of the variant polypeptide. Preferably, the dosing is given by injections, most preferably intravenous or subcutaneous injections, depending in part on whether the administration is brief or chronic.

For the prevention or treatment of disease, the appropriate dosage of polypeptide variant will depend on the type of disease to be treated, the severity and course of the disease, whether the variant polypeptide is administered for preventive or therapeutic purposes, previous therapy, the patient's clinical history and response to the polypeptide variant, and the discretion of the attending physician. The variant polypeptide is suitably administered to the patient at one time or over a series of treatments.

For example, depending on the type and severity of the disease, about 0.1 µg/kg to 15 mg/kg (e.g., 0.120 mg/kg) of variant polypeptide is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until the symptoms are sufficiently reduced or eliminated. The progress of this therapy is easily monitored by conventional techniques and assays, and may be used to adjust dosage to achieve a therapeutic effect.

These suggested amounts of variant polypeptide are subject to a great deal of therapeutic discretion. The key factor in selecting an appropriate dose and scheduling is the result obtained. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners.

A therapeutically effective amount of a variant polypeptide to be administered is the dosage level required for a patient such that the symptoms of the disease being treated are reduced. Additionally, a therapeutically effective amount may refer to the amount of therapeutic agent sufficient to delay or minimize or prevent the onset of disease, e.g., delay or minimize or prevent the spread of cancer. A therapeutically effective amount may refer to the amount of therapeutic agent (e.g., variant polypeptide) may also refer to the amount of the therapeutic agent that provides a therapeutic benefit in the treatment or management of a disease in a subject. Further, a therapeutically effective amount with respect to a therapeutic agent of the invention refers to the amount of therapeutic agent alone, or in combination with other therapies, that provides a therapeutic benefit in the treatment or management of a disease in a subject. The variant polypeptide need not be, but is optionally formulated with one or more agents currently used to prevent or treat the disorder in question. The effective amount of such other agents depends on the amount of variant polypeptide present in the formulation, the type of disorder or treatment, and other factors discussed above. A first prophylactic or therapeutic agent (e.g., variant polypeptide or polypeptide comprising a variant Fc region of the invention or functional fragment thereof) can be administered prior to, concomitantly with, or subsequent to the administration of a second prophylactic or therapeutic agent to a subject with a disorder.

Therapeutic agents of the invention may be frozen or lyophilized for storage and reconstituted in a suitable sterile carrier prior to use. Lyophilization and reconstitution can lead to varying degrees of antibody activity loss. Dosages may have to be adjusted to compensate. Generally, pH between 6 and 8 is preferred.

The use of a monoclonal antibody comprising a variant Fc region of the present invention for treating or preventing of at least one of the aforementioned disorders (e.g., cancer) in which the antigen to which the monoclonal antibody binds is detrimental or which benefits from decreased levels of the antigen is contemplated herein. Additionally, the use of an antibody comprising a variant Fc region of the present invention for use in the manufacture of a medicament for the treatment of at least one of the aforementioned disorders is contemplated.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, includes administration of a compound of the present invention for treatment of a disease or condition in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease or disorder or alleviating symptoms or complications thereof. Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation.

Anti-CD20 Antibodies

An anti-CD20 antibody comprising a variant Fc region of the present invention is contemplated to fall within the scope of the invention (see, e.g., Example 4 and FIG. 4 herein). In one embodiment, an anti-CD20 antibody comprises a variant Fc region of the invention, or portion thereof comprising the amino acid substitution, as listed in Tables 1-10 herein, the anti-CD20 antibody may further comprise a peptide with the sequence shown in SEQ ID NO: 13, 14, 15 or 16. In another embodiment, an anti-CD20 antibody comprises a variant Fc region of the invention, or portion thereof comprising the amino acid substitution, as listed in Tables 1-10 herein, and further comprises peptides with the sequences shown in:
a) SEQ ID NO: 13 and SEQ ID NO: 14;
b) SEQ ID NO: 15 and SEQ ID NO: 16;
c) SEQ ID NOs: 17, 18, 19, 20, 21 and 22; or
d) SEQ ID NOs: 23, 24, 25, 26, 27 and 28.

More preferably, an anti-CD20 antibody of the invention comprises a variant Fc region, or portion thereof, comprising amino acid substitution(s) selected from the group consisting of:
a) 247I and 339D;
b) 247I and 339Q; and
c) 378D;
and further comprises a variable region comprising polypeptides with the sequences selected from the group consisting of:
a) SEQ ID NO: 13 and SEQ ID NO: 14;
b) SEQ ID NO: 15 and SEQ ID NO: 16;
c) SEQ ID NOs: 17, 18, 19, 20, 21 and 22; and
d) SEQ ID NOs: 23, 24, 25, 26, 27 and 28.

Additional Variant Fc Region Uses

The variants, and nucleic acid sequences encoding variants, of the present invention may be used in many ways. For example, variants of the present invention may be used in drug screening assays. For example, candidate compounds may be evaluated for their ability to alter or interfere with Fc effector functions by contacting a variant with the candidate compound and determining binding of the candidate compound to the variant. The variant may be immobilized using methods known in the art such as binding a GST-variant fusion protein to a polymeric bead containing glutathione. A chimeric gene encoding a GST fusion protein is constructed by fusing DNA encoding the variant of interest to the DNA encoding the carboxyl terminus of GST (See, e.g., Smith et al., Gene 67:31 [1988]). The fusion construct is then transformed into a suitable expression system (e.g., *E. coli* XA90) in which the expression of the GST fusion protein can be induced with isopropyl-f-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the variant is correlated with the ability of the compound to disrupt the one or more effector functions.

In another screening method, either the variant or a selected FcR is immobilized using methods known in the art, such as adsorption onto a plastic microtiter plate or specific binding of a GST-fusion protein to a polymeric bead containing glutathione. For example, GST-variant is bound to glutathione-Sepharose beads. The immobilized variant is then contacted with an FcR and a candidate compound. Unbound peptide is then removed and the complex solubilized and analyzed to determine the amount of bound labeled peptide. A decrease in binding is an indication that the candidate compound inhibits the interaction of variant with the FcR. This screening method is particularly useful with variants of the present invention that show an increased level of A variation of this method allows for the screening of compounds that are capable of disrupting a previously-formed variant/Fc receptor complex. For example, in some embodiments a complex comprising a variant bound to an FcR is immobilized as described above and contacted with a candidate compound. The dissolution of the complex by the candidate compound correlates with the ability of the compound to disrupt or inhibit the interaction between the variant being tested and the FcR being. In this regard, compounds with therapeutic potential (e.g., in humans) may be identified (e.g., compounds useful in treating human disease, such as autoimmune diseases).

Another technique for drug screening provides high throughput screening for compounds having suitable binding affinity to variant peptides and is described in detail in WO 84/03564. Briefly, large numbers of different small peptide test compounds are synthesized on a solid substrate, such as plastic pins or some other surface. The peptide test compounds are then reacted with variant peptides and washed. Bound variant peptides are then detected by methods well known in the art.

Another technique uses antibodies directed to variant peptides. Such antibodies capable of specifically binding to variant peptides compete with a test compound for binding to a given variant. In this manner, the antibodies can be used to detect the presence of any peptide that shares one or more antigenic determinants of the variant peptide.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with nucleic acid encoding at least one variant Fc region for screening compounds for activity, and in particular to high throughput screening of compounds from combinatorial libraries (e.g., libraries containing greater than $10^4$ compounds). The cell lines of the present invention can be used in a variety of screening methods.

The variants of the present invention may be used as an affinity purification agent. For example, the variant may be immobilized on a solid phase such a Sephadex resin or filter paper, using methods well known in the art. The immobilized variant is then contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer, pH 5.0, that will release the antigen from the variant polypeptide.

The variant polypeptide may also be useful in diagnostic assays (e.g., for detecting expression of an antigen of interest in specific cells, tissues, or serum). For diagnostic applications, the variant will typically be labeled with a detectable moiety (such labels are also useful in the Fc region assays described above). Numerous labels are available, including, but not limited to, radioisotopes (e.g., $^{35}S$, $^{14}C$, $^{125}I$, $^3H$, and $^{131}I$), fluorescent labels (e.g., rare earth chelates (europium chelates) or fluorescein and its derivatives, rhodamine and its derivatives, dansyl, Lissamine, phycoerythrin and Texas Red), and various enzyme-substrate labels (see, e.g., U.S. Pat. No. 4,275,149), and luciferase, luciferin, 2,3-dihydrophthalazinediones, malate dehydrogenase, urease, peroxidase such as horseradish peroxidase (HRPO), alkaline phosphatase, 3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like). Examples of enzyme-substrate combinations include, for example: (i) horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); (ii) alkaline phosphatase (AP) with para-nitrophenyl phosphate as chromogenic substrate; and (iii)-D-galactosidase (R-D-Gai) with a chromogenic substrate or fluorogenic substrate.

The variants of the present invention may also be used for in vivo diagnostic assays. For example, the variant polypeptide is labeled with a radionuclide so that the antigen or cells expressing it can be localized using immunoscintiography.

TABLE 1

Fc Variants

| Position+ | Amino Acid Substitution* |
|---|---|
| 235 | G, R |
| 236 | F, R, Y |
| 237 | K, N, R |
| 238 | E, G, H, I, L, V, W, Y |
| 244 | L |
| 245 | R |
| 247 | A, D, E, F, M, N, Q, R, S, T, W, Y |
| 248 | F, P, Q, W |
| 249 | L, M, N, P, Y |
| 251 | H, I, W |
| 254 | D, E, F, G, H, I, K, L, M, N, P, Q, R, V, W, Y |
| 255 | K, N |
| 256 | H, I, K, L, V, W, Y |
| 257 | A, I, M, N, S |
| 258 | D |
| 260 | S |
| 262 | L |
| 264 | S |
| 265 | K, S |
| 267 | H, I, K |
| 268 | K |
| 269 | N, Q |
| 271 | T |
| 272 | H, K, L, R |
| 279 | A, D, F, G, H, I, K, L, M, N, Q, R, S, T, W, Y |
| 280 | T |
| 283 | F, G, H, I, K, L, M, P, R, T, W, Y |
| 286 | F |
| 288 | N, P |
| 292 | E, F, G, I, L |
| 293 | S, V |
| 301 | W |
| 304 | E |
| 307 | E, M |
| 312 | P |
| 315 | F, K, L, P, R |
| 316 | F, K |
| 317 | P, T |
| 318 | N, P, T |
| 332 | F, G, L, M, S, V, W |
| 339 | D, E, F, G, H, I, K, L, M, N, Q, R, S, W, Y |
| 341 | D, E, F, H, I, K, L, M, N, P, Q, R, S, T, V, W, Y |
| 343 | A, D, E, F, G, H, I, K, L, M, N, Q, R, S, T, V, W, Y |
| 373 | D, E, F, G, H, I, K, L, M, N, Q, R, S, T, V, W |
| 375 | R |
| 376 | E, F, G, H, I, L, M, N, P, Q, R, S, T, V, W, Y |
| 377 | G, K, P |
| 378 | D, N |
| 379 | N, Q, S, T |
| 380 | D, N, S, T |
| 382 | D, F, H, I, K, L, M, N, P, Q, R, S, T, V, W, Y |
| 385 | E, P |
| 386 | K |
| 423 | N |
| 424 | H, M, V |
| 426 | D, L |
| 427 | N |

TABLE 1-continued

Fc Variants

| Position⁺ | Amino Acid Substitution* |
|---|---|
| 429 | A, F, M |
| 430 | A, D, F, G, H, I, K, L, M, N, P, Q, R, S, T, V, W, Y |
| 431 | H, K, P |
| 432 | R, S |
| 438 | G, K, L, T, W |
| 439 | E, H, Q |
| 440 | D, E, F, G, H, I, K, L, M, Q, T, V |
| 442 | K |

⁺Fc amino acid position according to EU numbering
*e.g., at position 249: 249L, 249M, 249N or 249Y

TABLE 2

Fc variants: effector function changes

| Variant* | ADCC enhanced | ADCC diminished | FcRn Binding enhanced | FcRn Binding diminished | CDC enhanced | CDC diminished |
|---|---|---|---|---|---|---|
| 235G | | | | | | X |
| 235Q | | X | | X | | |
| 235R | | X | | | | |
| 235S | | X | | | | X |
| 236F | | X | | | | |
| 236R | | X | | | | X |
| 236Y | | X | | X | X | |
| 237E | | X | | | | X |
| 237K | | X | | X | | X |
| 237N | | X | | | | X |
| 237R | | X | | X | | X |
| 238A | | X | | | | X |
| 238E | | X | | X | | X |
| 238G | | X | | X | | X |
| 238H | | X | | X | | X |
| 238I | | X | | | | X |
| 238L | | X | X | | | X |
| 238V | | X | | | | X |
| 238W | | X | | X | | X |
| 238Y | | X | | X | | X |
| 244L | | | X | | X | |
| 245R | | X | X | | | X |
| 247A | X | | | X | X | |
| 247D | | | | X | X | |
| 247E | | | | X | X | |
| 247F | X | | | X | | |
| 247G | | X | | X | X | |
| 247H | X | | | X | | X |
| 247I | X | | | X | | X |
| 247L | X | | | X | | X |
| 247M | X | | | X | | |
| 247N | | | | X | X | |
| 247Q | | | | X | X | |
| 247R | | X | | X | X | |
| 247S | | | | X | X | |
| 247T | X | | | | | X |
| 247V | X | | | | | |
| 247W | | | | X | X | |
| 247Y | X | | | X | | X |
| 248A | | | | X | | |
| 248F | | | | X | X | |
| 248P | | | | X | X | |
| 248Q | | | | X | X | |
| 248W | | | | X | X | |
| 249E | X | | | X | X | |
| 249L | | X | | X | X | |
| 249M | | | | X | X | |
| 249N | | | | | | X |
| 249P | | X | X | | | X |
| 249Y | X | | | | X | X |
| 250K | | X | | | | X |
| 250M | | X | X | | | X |
| 250R | | X | | X | X | |
| 251F | X | | | X | X | |
| 251H | | X | | X | X | |
| 251I | | X | | X | X | |
| 251W | | X | | X | X | |
| 252Y | | X | X | | | X |

TABLE 2-continued

Fc variants: effector function changes

| Variant* | ADCC enhanced | ADCC diminished | FcRn Binding enhanced | FcRn Binding diminished | CDC enhanced | CDC diminished |
|---|---|---|---|---|---|---|
| 254A | | | | X | X | |
| 254D | | | | X | | X |
| 254E | | | | X | | X |
| 254F | X | | | X | X | |
| 254G | | | | X | | |
| 254H | | | | X | | |
| 254I | | | | X | | X |
| 254K | | | | X | X | |
| 254L | | X | | X | X | |
| 254M | X | | | X | X | |
| 254N | | | | X | | |
| 254P | | X | | X | | X |
| 254Q | | X | | X | | X |
| 254R | | | | X | X | |
| 254T | | X | | X | | X |
| 254V | | X | | X | | X |
| 254W | | | | X | X | |
| 254Y | X | | | X | X | |
| 255K | | | | X | X | |
| 255N | | | | X | | X |
| 256A | X | | X | | X | |
| 256F | X | | | X | | |
| 256G | | | X | | X | |
| 256H | | | | X | | |
| 256I | | | | X | X | |
| 256K | | | | X | | |
| 256L | | | | | X | |
| 256M | X | | | X | X | |
| 256P | | | X | | X | |
| 256Q | | | | X | X | |
| 256R | | | | X | | |
| 256V | | X | | | | |
| 256W | | | | X | X | |
| 256Y | | | | X | X | |
| 257A | | X | X | | | X |
| 257I | | X | X | | | X |
| 257M | | X | X | | | X |
| 257N | | X | X | | | X |
| 257S | | X | X | | | X |
| 257V | | X | X | | | X |
| 258D | X | | X | | | |
| 260S | | X | X | | X | |
| 262L | | X | X | | | X |
| 264S | | X | | X | | X |
| 265H | | X | | | | |
| 265K | | X | | | | |
| 265S | | X | | X | | |
| 265Y | | X | | X | | X |
| 267G | | X | | X | | X |
| 267H | | X | | | | X |
| 267I | | X | | X | | X |
| 267K | | X | | | | X |
| 268D | X | | | X | X | |
| 268E | X | | X | | | |
| 268K | | | | X | | X |
| 269N | | X | | | | X |
| 269Q | | X | | | | X |
| 270A | | X | | X | | X |
| 270G | | X | | | | X |
| 270K | | X | X | | | X |
| 270M | | X | | X | | X |
| 270N | | X | | | | X |
| 271T | | X | | | | X |
| 272H | | X | X | | | X |
| 272K | | X | X | | | |
| 272L | | X | X | | | X |
| 272N | | X | | | | X |
| 272R | | X | X | | | |
| 279A | X | | X | | | |
| 279D | | X | X | | | |
| 279F | | X | | | | |
| 279G | | | X | | | |
| 279H | | | X | | | |
| 279I | | | | X | | |

TABLE 2-continued

Fc variants: effector function changes

| Variant* | ADCC enhanced | ADCC diminished | FcRn Binding enhanced | FcRn Binding diminished | CDC enhanced | CDC diminished |
|---|---|---|---|---|---|---|
| 279K |  | X |  | X |  |  |
| 279L |  | X |  | X |  |  |
| 279M |  |  | X |  |  |  |
| 279N |  |  | X |  |  |  |
| 279Q |  |  | X |  | X |  |
| 279R |  |  | X |  |  |  |
| 279S |  |  | X |  | X |  |
| 279T |  |  | X |  |  |  |
| 279W |  | X | X |  | X |  |
| 279Y |  |  | X |  | X |  |
| 280A | X |  |  | X |  |  |
| 280K | X |  |  |  | X |  |
| 280T |  |  |  | X | X |  |
| 283A | X |  | X |  |  |  |
| 283D |  | X | X |  |  |  |
| 283F |  | X | X |  | X |  |
| 283G |  | X | X |  | X |  |
| 283H |  | X | X |  | X |  |
| 283I | X |  | X |  | X |  |
| 283K | X |  | X |  | X |  |
| 283L |  | X | X |  | X |  |
| 283M | X |  |  |  | X |  |
| 283N |  |  | X |  | X |  |
| 283P |  |  | X |  | X |  |
| 283Q |  |  | X |  |  |  |
| 283R | X |  | X |  | X |  |
| 283S |  |  | X |  | X |  |
| 283T |  |  | X |  |  |  |
| 283W |  | X | X |  | X |  |
| 283Y |  | X | X |  |  |  |
| 285N |  | X | X |  |  |  |
| 286F |  |  | X |  |  |  |
| 288N | X |  | X |  |  |  |
| 288P |  | X | X |  |  |  |
| 292A | X |  |  |  |  | X |
| 292E |  | X |  | X |  |  |
| 292F |  | X |  | X |  |  |
| 292G |  | X |  | X |  |  |
| 292I |  | X |  | X |  |  |
| 292L |  |  |  | X | X |  |
| 293S |  | X |  |  |  | X |
| 293V |  | X | X |  |  |  |
| 301W |  | X |  |  |  | X |
| 304E |  | X |  |  |  |  |
| 307A |  | X | X |  | X |  |
| 307E |  | X | X |  |  | X |
| 307M |  | X | X |  | X |  |
| 311A | X |  | X |  |  |  |
| 311D | X |  |  | X |  |  |
| 311E |  |  |  | X |  | X |
| 311F |  | X |  | X | X |  |
| 311G |  |  |  | X |  |  |
| 311I |  | X | X |  |  | X |
| 311K |  | X | X |  |  | X |
| 311L |  |  | X |  |  | X |
| 311M |  |  | X |  |  | X |
| 311R |  |  |  | X |  | X |
| 311N | X |  |  | X |  |  |
| 311S |  | X |  |  |  | X |
| 311T | X |  |  |  |  | X |
| 311V | X |  | X |  |  | X |
| 311W |  |  | X |  |  | X |
| 311Y | X |  |  | X |  | X |
| 312P |  | X | X |  |  | X |
| 314F |  | X |  | X |  | X |
| 314I |  | X |  |  |  | X |
| 314V |  | X |  | X |  | X |
| 314W |  | X |  | X |  | X |
| 314Y |  |  |  |  |  | X |
| 315F |  | X |  | X |  | X |
| 315K |  |  |  | X |  | X |
| 315L | X |  |  |  |  | X |
| 315P |  | X |  | X |  | X |
| 315R |  |  |  |  |  | X |

TABLE 2-continued

Fc variants: effector function changes

| Variant* | ADCC enhanced | ADCC diminished | FcRn Binding enhanced | FcRn Binding diminished | CDC enhanced | CDC diminished |
|---|---|---|---|---|---|---|
| 316F |  | X |  | X |  | X |
| 316K |  |  | X |  | X |  |
| 317P |  | X | X |  | X |  |
| 317T |  |  |  | X | X |  |
| 318N | X |  | X |  | X |  |
| 318P | X |  |  |  |  | X |
| 318T | X |  | X |  | X |  |
| 318V | X |  |  |  |  |  |
| 326W |  | X |  | X | X |  |
| 327T |  | X |  | X |  | X |
| 328V |  | X |  |  |  | X |
| 329Y |  | X |  |  |  | X |
| 330K | X |  |  |  |  | X |
| 330R |  |  |  |  |  | X |
| 332A |  |  |  |  | X |  |
| 332D | X |  |  |  | X |  |
| 332E | X |  |  |  | X |  |
| 332F |  |  | X |  | X |  |
| 332G |  |  |  |  | X |  |
| 332H |  | X | X |  | X |  |
| 332K |  | X | X |  |  | X |
| 332L |  | X | X |  | X |  |
| 332M |  |  | X |  | X |  |
| 332N |  |  |  |  | X |  |
| 332Q |  |  |  |  | X |  |
| 332R |  | X | X |  |  |  |
| 332S |  |  | X |  | X |  |
| 332T | X |  |  |  | X |  |
| 332V | X |  |  |  | X |  |
| 332W |  | X | X |  | X |  |
| 332Y |  |  |  |  | X |  |
| 339D | X |  |  |  | X |  |
| 339E |  |  |  | X |  | X |
| 339F | X |  |  |  | X |  |
| 339G | X |  |  | X | X |  |
| 339H |  |  |  |  | X |  |
| 339I | X |  |  |  | X |  |
| 339K | X |  |  |  | X |  |
| 339L |  |  |  | X |  |  |
| 339M | X |  |  |  |  | X |
| 339N | X |  | X |  | X |  |
| 339Q | X |  |  |  | X |  |
| 339R | X |  |  | X | X |  |
| 339S | X |  |  |  | X |  |
| 339T | X |  | X |  | X |  |
| 339W |  |  | X |  | X |  |
| 339Y |  |  |  |  | X |  |
| 341D |  | X |  | X | X |  |
| 341E |  | X |  | X | X |  |
| 341F |  | X |  | X | X |  |
| 341H |  | X |  |  | X |  |
| 341I |  | X |  | X | X |  |
| 341K |  | X |  | X | X |  |
| 341L |  | X |  | X | X |  |
| 341M |  | X |  | X | X |  |
| 341N |  | X |  | X | X |  |
| 341P |  | X | X |  | X |  |
| 341Q |  | X |  | X | X |  |
| 341R |  | X |  | X | X |  |
| 341S |  | X |  | X | X |  |
| 341T |  | X |  | X | X |  |
| 341V |  |  |  | X | X |  |
| 341W |  | X |  | X | X |  |
| 341Y |  | X |  | X | X |  |
| 343A |  | X |  |  | X |  |
| 343D |  | X |  |  | X |  |
| 343E |  | X | X |  | X |  |
| 343F |  | X |  |  |  |  |
| 343G |  | X |  |  | X |  |
| 343H |  | X | X |  | X |  |
| 343I |  |  |  |  |  | X |
| 343K |  |  | X |  | X |  |
| 343L |  | X |  |  | X |  |
| 343M |  | X |  | X | X |  |

TABLE 2-continued

Fc variants: effector function changes

| Variant* | ADCC enhanced | ADCC diminished | FcRn Binding enhanced | FcRn Binding diminished | CDC enhanced | CDC diminished |
|---|---|---|---|---|---|---|
| 343N |  | X |  |  | X |  |
| 343Q |  | X | X |  | X |  |
| 343R |  | X | X |  | X |  |
| 343S |  | X |  |  | X |  |
| 343T |  | X | X |  | X |  |
| 343V |  | X |  | X |  |  |
| 343W |  | X |  | X |  |  |
| 343Y |  | X | X |  | X |  |
| 373A |  | X |  | X |  |  |
| 373D |  | X |  | X | X |  |
| 373E |  | X |  |  | X |  |
| 373F |  | X |  |  | X |  |
| 373G |  | X |  | X |  |  |
| 373H |  |  |  |  | X |  |
| 373I |  | X |  |  | X |  |
| 373K |  | X |  | X | X |  |
| 373L |  | X |  | X | X |  |
| 373M |  | X |  | X | X |  |
| 373N |  | X |  | X | X |  |
| 373Q |  | X |  | X | X |  |
| 373R |  | X |  |  | X |  |
| 373S |  | X |  | X |  | X |
| 373T |  | X |  | X | X |  |
| 373V |  | X |  | X | X |  |
| 373W |  | X |  | X | X |  |
| 375R |  | X | X |  | X |  |
| 376A | X |  | X |  | X |  |
| 376E |  | X |  |  |  |  |
| 376F |  | X |  |  | X |  |
| 376G |  | X | X |  | X |  |
| 376H |  | X |  | X | X |  |
| 376I |  |  | X |  |  |  |
| 376L |  |  |  | X | X |  |
| 376M |  |  | X |  |  |  |
| 376N |  |  |  |  | X |  |
| 376P |  |  | X |  | X |  |
| 376Q |  |  |  |  | X |  |
| 376R |  |  |  |  | X |  |
| 376S |  |  |  |  | X |  |
| 376T |  |  | X |  | X |  |
| 376V | X |  | X |  | X |  |
| 376W |  | X |  | X |  |  |
| 376Y |  | X |  | X |  |  |
| 377G | X |  |  |  |  |  |
| 377K | X |  | X |  |  |  |
| 377P |  |  |  |  | X |  |
| 378D |  |  | X |  |  | X |
| 378N |  |  | X |  |  |  |
| 379N | X |  |  |  | X |  |
| 379Q |  | X |  |  | X |  |
| 379S |  |  |  |  | X |  |
| 379T |  |  |  |  | X |  |
| 380A |  |  | X |  | X |  |
| 380D |  |  |  |  |  | X |
| 380N | X |  | X |  | X |  |
| 380S | X |  | X |  | X |  |
| 380T |  |  | X |  | X |  |
| 382A | X |  |  |  |  |  |
| 382D |  | X |  |  |  | X |
| 382F | X |  | X |  |  | X |
| 382H |  |  | X |  |  |  |
| 382I | X |  | X |  | X |  |
| 382K |  |  | X |  |  |  |
| 382L |  |  | X |  | X |  |
| 382M |  |  | X |  |  |  |
| 382N |  |  | X |  |  | X |
| 382P |  |  |  |  |  | X |
| 382Q |  |  | X |  | X |  |
| 382R |  |  | X |  |  | X |
| 382S |  | X | X |  |  | X |
| 382T |  |  | X |  |  |  |
| 382V |  |  | X |  | X |  |
| 382W |  |  | X |  |  | X |
| 382Y |  |  | X |  |  | X |

TABLE 2-continued

Fc variants: effector function changes

| Variant* | ADCC enhanced | ADCC diminished | FcRn Binding enhanced | FcRn Binding diminished | CDC enhanced | CDC diminished |
|---|---|---|---|---|---|---|
| 385E | X | | | | | X |
| 385P | | | | | | X |
| 386K | | | | | X | |
| 423N | | | X | | | X |
| 424H | | | | | | X |
| 424M | | X | | X | | X |
| 424V | | | | X | | |
| 426D | | | | X | X | |
| 426L | | | | | X | |
| 427N | X | | X | | | X |
| 429A | | X | | X | X | |
| 429F | | X | | X | X | |
| 429M | X | | | X | X | |
| 430A | | | X | | X | |
| 430D | | | | X | X | |
| 430F | | | X | | X | |
| 430G | | | X | | X | |
| 430H | | X | X | | X | |
| 430I | | | X | | X | |
| 430K | | X | X | | X | |
| 430L | | | X | | X | |
| 430M | | | X | | X | |
| 430N | | X | X | | X | |
| 430P | | | | | X | |
| 430Q | | X | X | | | |
| 430R | | X | X | | X | |
| 430S | | | X | | X | |
| 430T | | | X | | X | |
| 430V | | | X | | X | |
| 430W | | X | | X | X | |
| 430Y | | | X | | X | |
| 431H | | | X | | X | |
| 431K | | | X | | | |
| 431P | | | | X | X | |
| 432R | | X | | X | X | |
| 432S | | X | | X | X | |
| 434G | | | X | | | X |
| 434H | | | X | | | X |
| 434I | | X | X | X | | X |
| 434W | X | | X | | X | |
| 434Y | | | X | | X | |
| 436I | X | | X | | | X |
| 436L | | | X | | | |
| 436T | | | X | | | X |
| 438G | | | | | | X |
| 438K | | | X | | | |
| 438L | | | X | | X | |
| 438T | | | X | | | X |
| 438W | | | X | | X | |
| 439E | | | | | | X |
| 439H | | | | | | X |
| 439Q | | | | X | | X |
| 440A | | | | X | | X |
| 440D | | X | | X | | |
| 440E | | | | X | | |
| 440F | | | | X | | X |
| 440G | X | | | | | X |
| 440H | X | | X | | | |
| 440I | X | | | | | X |
| 440K | | | X | | | X |
| 440L | X | | X | | | X |
| 440M | | | | X | | X |
| 440N | | | | | | |
| 440Q | | | | | X | |
| 440R | | | | | | |
| 440T | | X | | | | |
| 440V | | X | | | | |
| 440W | | | | | | |
| 440Y | | | | | X | |
| 442K | | X | X | | | |

*Variants tested in anti-CD20 antibody, IgG1 Fc region

TABLE 3

Enhanced ADCC

| Position+ | Amino Acid Substitution* |
|---|---|
| 247 | A, F, H, I, L, M, T, V, Y |
| 249 | E, Y |
| 251 | F |
| 254 | F, M, Y |
| 256 | A, M |
| 258 | D |
| 268 | D, E |
| 279 | A |
| 280 | A, K |
| 283 | A, I, K, M, R |
| 288 | N |
| 292 | A |
| 311 | A, D, N, T, V, Y |
| 315 | L |
| 318 | N, P, T, V |
| 330 | K |
| 332 | T, V |
| 339 | D, F, G, I, K, M, N, Q, R, S, T |
| 376 | A, V |
| 377 | G, K |
| 379 | N |
| 380 | N, S |
| 382 | A, I |
| 385 | E |
| 427 | N |
| 429 | M |
| 434 | W |
| 436 | I |
| 440 | G, H, I, L |

+Fc amino acid position according to EU numbering
*e.g., at position 249: 249E or 249Y

TABLE 4

Diminished ADCC

| Position+ | Amino Acid Substitution |
|---|---|
| 235 | Q, R, S |
| 236 | F, R, Y |
| 237 | E, K, N, R |
| 238 | E, G, H, I, L, V, W, Y |
| 247 | G, R |
| 249 | L, P |
| 250 | K, M, R |
| 251 | H, I, W |
| 252 | Y |
| 254 | L, P, Q, T, V |
| 256 | V |
| 257 | A, I, M, N, S, V |
| 260 | S |
| 262 | L |
| 264 | S |
| 265 | H, K, S |
| 267 | G, H, I, K |
| 269 | N, Q |
| 270 | A, G, K, M, N |
| 271 | T |
| 272 | H, K, L, N, R |
| 279 | D, F, K, L, W |
| 283 | D, F, G, H, L, T, W, Y |
| 285 | N |
| 288 | P |
| 292 | E, F, G, I |
| 293 | S, V |
| 301 | W |
| 304 | E |
| 307 | A, E, M |
| 311 | F, I, K, S |
| 312 | P |
| 314 | F, I, V, W |
| 315 | F, P |
| 316 | F |
| 317 | P |
| 327 | T |
| 328 | V |
| 329 | Y |
| 332 | G, K, L, R, W |
| 341 | D, E, F, H, I, K, L, M, N, P, Q, R, S, T, W, Y |
| 343 | A, D, E, F, G, H, L, M, N, Q, R, S, T, V, W, Y |
| 373 | A, D, E, F, G, I, K, L, M, N, Q, R, S, T, V, W |
| 375 | R |
| 376 | A, E, F, G, H, W, Y |
| 379 | Q |
| 382 | D, S |
| 429 | A, F |
| 430 | H, K, N, Q, R, W |
| 432 | R, S |
| 434 | I |
| 440 | D, T, V |
| 442 | K |

+Fc amino acid position according to EU numbering

TABLE 5

Enhanced FcRn Binding Affinity

| Position+ | Amino Acid Substitution |
|---|---|
| 238 | L |
| 244 | L |
| 245 | R |
| 249 | P |
| 252 | Y |
| 256 | P |
| 257 | A, I, M, N, S, V |
| 258 | D |
| 260 | S |
| 262 | L |
| 270 | K |
| 272 | L, R |
| 279 | A, D, G, H, M, N, Q, R, S, T, W, Y |
| 283 | A, D, F, G, H, I, K, L, N, P, Q, R, S, T, W, Y |
| 285 | N |
| 286 | F |
| 288 | N, P |
| 293 | V |
| 307 | A, E, M |
| 311 | A, I, K, L, M, V, W |
| 312 | P |
| 316 | K |
| 317 | P |
| 318 | N, T |
| 332 | F, H, K, L, M, R, S, W |
| 339 | N, T, W |
| 341 | P |
| 343 | E, H, K, Q, R, T, Y |
| 375 | R |
| 376 | G, I, M, P, T, V |
| 377 | K |
| 378 | D, N |
| 380 | N, S, T |
| 382 | F, H, I, K, L, M, N, Q, R, S, T, V, W, Y |
| 423 | N |
| 427 | N |
| 430 | A, F, G, H, I, K, L, M, N, Q, R, S, T, V, Y |
| 431 | H, K |
| 434 | F, G, H, W, Y |
| 436 | I, L, T |
| 438 | K, L, T, W |
| 440 | K |
| 442 | K |

+Fc amino acid position according to EU numbering

TABLE 6

Diminished FcRn Binding Affinity

| Position† | Amino Acid Substitution |
|---|---|
| 235 | Q |
| 236 | Y |
| 237 | K, R |
| 238 | E, G, H, W |
| 247 | A, D, E, F, G, H, I, L, M, N, Q, R, S, W, Y |
| 248 | A, F, P, Q, W |
| 249 | E, L, M, Y |
| 251 | F, H, I, W |
| 254 | D, E, F, G, H, I, K, L, M, N, P, Q, R, T, V, W, Y |
| 255 | K, N |
| 256 | F, H, I, K, M, R, W, Y |
| 264 | S |
| 265 | S, Y |
| 267 | G, I |
| 268 | D, K |
| 270 | A, M |
| 279 | I, K, L |
| 280 | T |
| 292 | E, F, G, I, L |
| 311 | D, E, F, G, N, R, Y |
| 315 | F, K, P |
| 316 | F |
| 317 | T |
| 326 | W |
| 327 | T |
| 339 | E, G, L, R |
| 341 | D, E, F, I, K, L, M, N, Q, R, S, T, V, W, Y |
| 343 | M, V, W |
| 373 | A, D, G, K, L, M, N, Q, S, T, V, W |
| 376 | H, L, W, Y |
| 424 | M, V |
| 426 | D |
| 429 | A, F, M |
| 430 | D, W |
| 431 | P |
| 432 | R, S |
| 434 | I |
| 439 | Q |
| 440 | A, D, E, F, M |

†Fc amino acid position according to EU numbering

TABLE 7

Enhanced CDC

| Position† | Amino Acid Substitution |
|---|---|
| 236 | Y |
| 244 | L |
| 247 | A, D, E, G, N, Q, R, S, W |
| 248 | F, P, Q, W |
| 249 | E, L, M, N, P, Y |
| 250 | K, R |
| 251 | F, H, I, W |
| 254 | A, F, K, L, M, R, Y |
| 255 | K |
| 256 | A, G, I, L, M, P, Q, W, Y |
| 260 | S |
| 268 | D |
| 279 | Q, S, W, Y |
| 280 | K, T |
| 283 | F, G, H, I, K, L, M, N, P, R, S, W |
| 292 | L |
| 307 | A, M |
| 311 | F, I, K, L, M, T, V, W, Y |
| 312 | P |
| 314 | F, I, V, W, Y |
| 315 | F, K, L, P, R |
| 316 | K |
| 317 | P, T |
| 318 | N, T |
| 332 | A, D, E, F, G, H, L, M, N, Q, S, T, W, Y |

TABLE 7-continued

Enhanced CDC

| Position† | Amino Acid Substitution |
|---|---|
| 339 | D, F, G, H, I, K, N, Q, R, S, T, W, Y |
| 341 | D, E, F, H, I, K, L, M, N, P, Q, R, S, T, V, W, Y |
| 343 | A, D, E, G, H, K, L, M, N, Q, R, S, T, W, Y |
| 373 | D, E, F, H, I, K, L, M, N, Q, R, T, V, W |
| 375 | R |
| 376 | A, F, G, H, L, N, P, Q, R, S, T, V |
| 377 | P |
| 379 | N, Q, S, T |
| 380 | A, N, S, T |
| 382 | I, L, Q, V |
| 386 | K |
| 426 | D, L |
| 429 | A, F, M |
| 430 | A, D, F, G, H, I, K, L, M, N, P, R, S, T, V, W, Y |
| 431 | H, P |
| 432 | R, S |
| 434 | W, Y |
| 438 | L, W |
| 440 | Q, Y |

†Fc amino acid position according to EU numbering

TABLE 8

Diminished CDC

| Position† | Amino Acid Substitution |
|---|---|
| 235 | G, S |
| 236 | R |
| 237 | E, K, N, R |
| 238 | A, E, G, H, I, L, V, W, Y |
| 245 | R |
| 247 | H, I, L, T, Y |
| 250 | M |
| 252 | Y |
| 254 | D, E, I, P, Q, T, V |
| 255 | N |
| 257 | A, I, M, N, S, V |
| 262 | L |
| 264 | S |
| 265 | H, Y |
| 267 | G, H, I, K |
| 268 | K |
| 269 | N, Q |
| 270 | G, M, N |
| 271 | T |
| 272 | H, L, N |
| 292 | A |
| 293 | S |
| 301 | W |
| 307 | E |
| 311 | E, S |
| 316 | F |
| 318 | P |
| 327 | T |
| 328 | V |
| 329 | Y |
| 330 | K, R |
| 332 | E, M |
| 343 | I |
| 373 | S |
| 378 | D |
| 380 | D |
| 382 | D, F, N, P, R, S, W, Y |
| 385 | E, P |

TABLE 8-continued

Diminished CDC

| Position+ | Amino Acid Substitution |
|---|---|
| 423 | N |
| 424 | H, M |
| 427 | N |

+Fc amino acid position according to EU numbering

EXAMPLES

The following examples are provided in order to demonstrate and further illustrate certain preferred embodiments and aspects of the present invention and are not to be construed as limiting the scope thereof.

Example I

Screening Variant Fc Regions in ADCC Assays

This example describes how variant Fc regions, in the context of an antibody (e.g., anti-CD20) are screened in an ADCC assay.

i. Peripheral Blood Mononuclear Cell (PBMC) Isolation

About 50 ml of peripheral blood is obtained from a healthy donor and diluted 1:2 with phosphate buffered saline (PBS), pH 7.0. The solutions are mixed by gently swirling the tube. About 12 ml of Histopaque-1077 (Sigma Cat. No. 1077-1) is carefully layered underneath the diluted blood sample followed by centrifugation in a Sorvall RT6000B centrifuge with swinging bucket rotor at 1000 rpm for 10 min. with brake off. The upper phase of the gradient is discarded by aspiration and the white-colored, PBMC-containing interphase collected and washed 3 times with Hanks' Balanced Salt Solution (Gibco Cat. No. 14025-092). The washed cell pellet is suspended in about 20 ml RPMI 1640 media containing 10% Fetal Bovine Serum (FBS) (Omega Scientific Cat. No. FB-01). The resuspended PBMCs are split into two T-175 culture flasks, and 30 ml of RPMI containing 10% FBS is added to each, followed by incubation overnight in a 37° C., 5% $CO_2$ incubator. The following day the nonadherent PBMCs are collected in 50 mL Falcon tubes, centrifuged as above and resuspended in RPMI containing 1% FBS lacking phenol red. A small portion of the resuspended cells are diluted 10-fold and counted using a hemocytometer. The remaining PBMCs are placed in the incubator until needed.

ii. Target Cell Line (Specific for Anti-CD20 ADCC Assays)

Wil.2 and SKW6.4 CD20-expressing B-cell lines are obtainable from ATCC and grown as recommended. One day before use, the cells are split 2-fold. The next day the cell number is adjusted to $4 \times 10^5$ cells/ml and 50 μl aliquots (20,000 cells/well) added to a 96-well tissue culture plate.

iii. IgG Dilutions

Prior to screening, IgG comprising an Fc variant of the present invention is expressed, purified and quantitated using a standard ELISA. For primary single-point ADCC screening, IgG variants are diluted to 40 ng/ml in RPMI media containing 1% FBS lacking phenol red. The final IgG concentration in the assay is diluted by 4-fold (i.e., 10 ng/ml final concentration). Fifty microliter aliquots of IgG are added to the target cells and incubated for about 15 minutes at 37° C. prior to adding the effector cells to the opsonized target cells.

When IgG titrations are performed, IgG concentration is varied in the range from about 0.0001 to 1 μg/ml. IgG dilutions are prepared using a 96-well microtiter plate by diluting the samples in RPMI containing 1% FBS lacking phenol red. The diluted IgG samples are then added to the assay plate containing the target cells.

iv. Effector Cells

The concentration of PBMCs are adjusted so effector-to-target ratio is in the range of 10-20:1 (i.e., $2-4 \times 10^6$ cells/ml). One hundred microliters of the resuspended PBMCs are added to each well of the opsonized target cells. The plates are incubated at 37° C. in the presence of 5% $CO_2$ for 3-4 hours.

v. Lactate-Dehydrogenase (LDH)-Release Detection

Target cell lysis is measured by detecting the release of LDH enzyme from the cytoplasm of damaged cells into the culture supernatant. Following incubation of the opsonized target cells with the effector cells, the assay plates are centrifuged at 2000 rpm for 5 minutes. About 75 μl of the cell culture supernatant is carefully removed while the pelleted cells and debris are avoided. This supernatant is added directly to a microtiter plate and to this is added 75 μl of LDH detection reagent (Roche Cat. No. 1 644 793). The plate is then incubated for approximately 15-30 min. and absorbance read at 490 nm using a Molecular Devices Vmax Kinetic Microplate Reader.

vi. Data Analysis

All ADCC screening assays are performed in duplicate. Each assay plate contains controls for spontaneous target lysis, spontaneous effector plus target lysis in the absence of IgG and target cell total lysis. Target cell total lysis is achieved by addition of 1% Triton X-100 to the target cells. Wild type controls are included on each assay plate and the ADCC assay signal averaged. The background value, obtained from the spontaneous lysis controls, is subtracted from each sample. The background value, obtained from the diluted IgG, is subtracted from each sample. The data are converted from absorbance values to percentage of specific-lysis based upon the spontaneous and total lysis controls. The percentage of specific-lysis is calculated from the following equation: percentage specific lysis=(experimental A490−background A490)/(maximal A490−background A490)×100, where background A490 is the sum of the A490 obtained from the effector and target cells in the absence of IgG and the IgG background due to contaminating LDH present in the crude IgG supernatants. The percentage of the Fc variant activity is normalized relative to the averaged wild type controls. The percentage of the normalized activity for duplicate assay plates are averaged and the standard deviation between individual assay plates calculated for each sample.

vii. Results

The relative ADCC specific activity are shown in Tables 9 (single substitutions) and 10 (combinatorial substitutions) below. The CDC values reported in Table 9 are generated as described in Example 2 herein and the FcRn binding assay value reported in Table 9 are generated as described in Example 3 herein. Results are further summarized in Tables 1 and 2 above. Those combinatorial substitutions which yield a higher ADCC value than either single substitution alone are: 247F,339D; 247I, 339D; 247L,339D; 247L,339T; and 247I, 339Q. Those combinatorial substitutions which yield ADCC lower than 80% that of wild-type ADCC even though they have higher than wild-type ADCC when tested alone are: 247A,339D; 247Y,339H; 247I,339I; 247T,339I; 247L,339N; 247A,339Q; and 247A,339R. Those combinatorial substitutions which yield ADCC lower than 10% that of wild-type ADCC even though they have higher than wild-type ADCC when tested alone are: 247I,339I; 247T,339I; and 247L, 339N.

TABLE 9

| WT* | Position and Variants* | ADCC | % CV | FcRn pH6.0 | % CV | CDC | % CV | n = |
|---|---|---|---|---|---|---|---|---|
|  | WT (a, z) | 100 |  | 100 |  | 100 |  |  |
| L | 235A | 87 | 23.2 | 102 | 11.9 | 67 | 7.9 | 2 |
| L | 235E | 80 | 17.4 | 87 | 16.2 | 48 | 35.8 | 2 |
| L | 235G | 93 | 30.3 | 85 | 21.2 | 58 | 46.0 | 2 |
| L | 235Q | 86 | 1.8 | 81 | 14.4 | 98 | 25.1 | 2 |
| L | 235R | 45 | 10.5 | 93 | 34.1 | 110 | 13.8 | 2 |
| L | 235S | 92 | 2.0 | 85 | 40.0 | 0 | 262.9 | 2 |
| G | 236F | 0 | 942.1 | 88 | 7.9 | 0 | 283.3 | 2 |
| G | 236R | 0 | 228.7 | 101 | 20.6 | 14 | 110.1 | 4 |
| G | 236Y | 8 | 72.7 | 76 | 10.0 | 168 | 0.3 | 2 |
| G | 237E | 0 | 89.2 | 93 | 35.0 | 36 | 28.8 | 4 |
| G | 237K | 0 | 113.3 | 78 | 12.8 | 12 | 136.0 | 4 |
| G | 237N | 0 | 107.5 | 91 | 16.3 | 22 | 31.5 | 4 |
| G | 237R | 0 | 81.3 | 56 | 60.6 | 28 | 10.5 | 4 |
| P | 238A | 0 | 205.8 | 90 | 9.6 | 29 | 49.5 | 4 |
| P | 238E | 0 | 20.6 | 76 | 6.7 | 24 | 101.0 | 4 |
| P | 238G | 0 | 92.8 | 66 | 6.9 | 23 | 120.5 | 4 |
| P | 238H | 0 | 48.9 | 72 | 11.4 | 11 | 206.3 | 4 |
| P | 238I | 0 | 180.4 | 94 | 6.4 | 18 | 54.1 | 4 |
| P | 238L | 0 | 37.4 | 115 | 13.6 | 34 | 50.1 | 4 |
| P | 238V | 46 | 11.8 | 102 | 8.3 | 67 | 19.2 | 4 |
| P | 238W | 0 | 66.6 | 87 | 5.4 | 23 | 103.4 | 4 |
| P | 238Y | 0 | 34.0 | 74 | 15.8 | 16 | 288.8 | 4 |
| P | 244L | 77 | 23.4 | 124 | 9.6 | 134 | 6.0 | 2 |
| P | 245R | 62 | 15.0 | 188 | 7.2 | 42 | 5.3 | 2 |
| P | 247A | 122 | 16.2 | 97 | 0.3 | 116 | 0.9 | 2 |
| P | 247D | 95 | 23.4 | 54 | 2.8 | 131 | 1.1 | 2 |
| P | 247E | 95 | 10.3 | 52 | 8.7 | 118 | 0.0 | 2 |
| P | 247F | 144 | 18.8 | 6 | 1258.9 | 71 | 34.1 | 6 |
| P | 247G | 82 | 16.1 | 75 | 4.2 | 137 | 0.9 | 2 |
| P | 247H | 145 | 11.2 | 35 | 252.4 | 79 | 7.5 | 6 |
| P | 247I | 140 | 22.9 | 79 | 30.7 | 22 | 198.3 | 6 |
| P | 247L | 144 | 10.1 | 57 | 33.7 | 0 | 722.7 | 16 |
| P | 247M | 127 | 21.0 | 18 | 1599.0 | 114 | 7.2 | 6 |
| P | 247N | 91 | 37.2 | 41 | 38.7 | 109 | 4.0 | 2 |
| P | 247Q | 103 | 8.5 | 26 | 294.3 | 137 | 3.7 | 4 |
| P | 247R | 58 | 15.5 | 72 | 1.2 | 127 | 4.9 | 2 |
| P | 247S | 106 | 38.6 | 81 | 15.0 | 130 | 2.6 | 2 |
| P | 247T | 129 | 11.2 | 75 | 27.5 | 37 | 34.8 | 10 |
| P | 247V | 120 | 13.5 | Na | na | na | na | 2 |
| P | 247W | 102 | 6.5 | 0 | 1314.2 | 122 | 0.5 | 2 |
| P | 247Y | 143 | 8.4 | 7 | na | 88 | 7.1 | 6 |
| K | 248A | 100 | 5.4 | 15 | 179.9 | 102 | 2.4 | 2 |
| K | 248F | 107 | 18.0 | 0 | 559.4 | 202 | 4.0 | 2 |
| K | 248P | 103 | 9.1 | 34 | 99.4 | 226 | 1.3 | 2 |
| K | 248Q | 101 | 0.5 | 38 | 89.3 | 174 | 17.9 | 2 |
| K | 248W | 102 | 9.4 | 30 | 54.5 | 166 | 8.3 | 2 |
| D | 249E | 110 | 6.7 | 78 | 22.4 | 258 | 16.1 | 4 |
| D | 249L | 73 | 1.4 | 15 | 179.9 | 214 | 3.2 | 2 |
| D | 249M | 101 | 9.6 | 50 | 4.5 | 163 | 1.2 | 2 |
| D | 249N | 94 | 15.9 | 112 | 14.0 | 255 | 10.9 | 4 |
| D | 249P | 56 | 4.0 | 138 | 21.0 | 119 | 0.2 | 2 |
| D | 249Y | 110 | 8.8 | 41 | 28.3 | 170 | 6.6 | 2 |
| T | 250K | 38 | 27.1 | 96 | 30.1 | 199 | 13.5 | 6 |
| T | 250M | 78 | 11.0 | 165 | 7.4 | 47 | 6.6 | 4 |
| T | 250R | 84 | 0.7 | 62 | 34.0 | 288 | 13.9 | 4 |
| L | 251F | 125 | 6.0 | 64 | 47.6 | 160 | 16.6 | 10 |
| L | 251H | 59 | 11.6 | 46 | 5.6 | 167 | 22.7 | 2 |
| L | 251I | 84 | 9.8 | 7 | 333.3 | 190 | 18.8 | 2 |
| L | 251W | 95 | 2.9 | 0 | na | 161 | 17.3 | 2 |
| M | 252Y | 61 | 5.8 | 964 | 27.9 | 62 | 46.1 | 4 |
| I | 253A | 103 | 6.1 | 0 | 12.0 | 81 | 23.9 | 4 |
| S | 254A | 99 | 20.1 | 7 | 733.0 | 139 | 11.2 | 4 |
| S | 254D | 101 | 14.2 | 7 | 113.9 | 74 | 31.2 | 2 |
| S | 254E | 102 | 3.8 | 6 | 107.9 | 72 | 35.2 | 2 |
| S | 254F | 121 | 11.2 | 0 | 1087.4 | 206 | 14.4 | 6 |
| S | 254G | 100 | 14.7 | 7 | 86.8 | 102 | 6.1 | 2 |
| S | 254H | 108 | 20.0 | 0 | 74.3 | 85 | 22.0 | 2 |
| S | 254I | 99 | 2.5 | 25 | 64.3 | 80 | 11.5 | 4 |
| S | 254K | 109 | 14.8 | 9 | 77.2 | 137 | 6.1 | 2 |
| S | 254L | 89 | 9.8 | 74 | 12.6 | 227 | 12.1 | 6 |
| S | 254M | 89 | 11.9 | 0 | 212.1 | 248 | 13.4 | 6 |
| S | 254N | 90 | 13.3 | 8 | 5.6 | 76 | 34.6 | 2 |
| S | 254P | 78 | 17.7 | 3 | 141.4 | 75 | 25.2 | 2 |
| S | 254Q | 84 | 12.6 | 9 | 121.2 | 74 | 25.2 | 2 |
| S | 254R | 99 | 1.3 | 14 | 128.2 | 152 | 4.8 | 2 |
| S | 254T | 54 | 51.9 | 32 | 34.7 | 75 | 12.1 | 2 |

TABLE 9-continued

| WT* | Position and Variants* | ADCC | % CV | FcRn pH6.0 | % CV | CDC | % CV | n = |
|---|---|---|---|---|---|---|---|---|
| S | 254V | 68 | 40.5 | 31 | 40.5 | 84 | 4.4 | 2 |
| S | 254W | 98 | 6.0 | 0 | 116.1 | 188 | 7.7 | 6 |
| S | 254Y | 117 | 9.4 | 0 | 129.1 | 211 | 15.7 | 6 |
| R | 255K | 96 | 3.5 | 41 | 65.9 | 276 | 9.3 | 4 |
| R | 255N | 84 | 17.7 | 27 | 162.7 | 81 | 18.1 | 2 |
| T | 256A | 115 | 16.5 | 160 | 3.0 | 190 | 19.6 | 2 |
| T | 256D | 97 | 5.3 | 544 | 10.6 | 86 | 23.2 | 6 |
| T | 256E | 91 | 12.9 | 339 | 8.4 | 104 | 7.2 | 6 |
| T | 256F | 119 | 3.3 | 5 | 435.0 | 128 | 26.6 | 2 |
| T | 256G | 95 | 20.0 | 162 | 8.0 | 221 | 24.5 | 2 |
| T | 256H | 103 | 6.3 | 26 | 6.1 | 91 | 11.9 | 2 |
| T | 256I | 93 | 11.5 | 72 | 3.7 | 157 | 16.2 | 4 |
| T | 256K | 100 | 6.7 | 31 | 20.6 | 92 | 20.2 | 2 |
| T | 256L | 93 | 3.9 | 78 | 60.5 | 267 | 22.7 | 4 |
| T | 256M | 122 | 17.4 | 35 | 78.9 | 200 | 14.8 | 10 |
| T | 256N | 102 | 7.2 | 229 | 6.4 | 86 | 23.2 | 2 |
| T | 256P | 109 | 11.8 | 190 | 6.1 | 260 | 11.8 | 8 |
| T | 256Q | 100 | 17.2 | 64 | 14.2 | 152 | 11.3 | 4 |
| T | 256R | 94 | 8.8 | 33 | 60.0 | 71 | 47.1 | 2 |
| T | 256S | 103 | 5.3 | 169 | 3.1 | 101 | 15.9 | 2 |
| T | 256V | 82 | 11.1 | 114 | 30.5 | 109 | 11.0 | 2 |
| T | 256W | 96 | 8.5 | 14 | 84.5 | 170 | 14.4 | 4 |
| T | 256Y | 97 | 7.2 | 68 | 18.6 | 127 | 18.0 | 2 |
| P | 257A | 86 | 11.5 | 319 | 15.0 | 34 | 53.7 | 4 |
| P | 257I | 54 | 16.4 | 1022 | 14.5 | 46 | 22.4 | 6 |
| P | 257M | 26 | 11.0 | 835 | 19.1 | 48 | 48.4 | 4 |
| P | 257N | 27 | 13.1 | 867 | 15.7 | 62 | 31.4 | 4 |
| P | 257S | 28 | 28.8 | 184 | 6.8 | 46 | 30.1 | 4 |
| P | 257V | 18 | 97.9 | 447 | 41.5 | 27 | 143.5 | 2 |
| E | 258D | 115 | 7.0 | 361 | 20.5 | 110 | 9.6 | 4 |
| T | 260S | 93 | 5.6 | 124 | 7.4 | 171 | 17.1 | 2 |
| V | 262L | 61 | 2.9 | 525 | 15.1 | 30 | 48.0 | 2 |
| V | 264S | 10 | 39.8 | 78 | 20.0 | 50 | 36.7 | 2 |
| D | 265H | 8 | 118.9 | 79 | 36.1 | 81 | 0.5 | 2 |
| D | 265K | 10 | 146.5 | 107 | 34.3 | 84 | 46.4 | 2 |
| D | 265S | 9 | 106.3 | 66 | 28.9 | 103 | 13.3 | 2 |
| D | 265Y | 3 | 7.6 | 33 | 88.8 | 62 | 21.5 | 2 |
| S | 267G | 29 | 8.6 | 86 | 0.9 | 60 | 18.1 | 4 |
| S | 267H | 0 | 48.4 | 86 | 16.8 | 47 | 41.1 | 4 |
| S | 267I | 0 | 78.0 | 83 | 11.8 | 50 | 37.8 | 4 |
| S | 267K | 0 | 73.3 | 102 | 14.2 | 26 | 47.1 | 4 |
| H | 268D | 110 | 7.8 | 68 | 32.4 | 122 | 10.7 | 6 |
| H | 268E | 110 | 8.3 | 126 | 17.8 | 100 | 8.4 | 8 |
| H | 268K | 98 | 17.6 | 86 | 10.4 | 24 | 112.7 | 4 |
| E | 269N | 23 | 74.0 | 92 | 17.0 | 30 | 69.4 | 4 |
| E | 269Q | 47 | 3.6 | 98 | 3.5 | 22 | 82.8 | 4 |
| D | 270A | 41 | 35.5 | 87 | 6.0 | 36 | 66.5 | 4 |
| D | 270G | 0 | 102.2 | 108 | 16.5 | 37 | 21.8 | 4 |
| D | 270K | 15 | 465.5 | 122 | 8.4 | 0 | 462.9 | 4 |
| D | 270M | 49 | 19.2 | 81 | 5.2 | 25 | 606.9 | 4 |
| D | 270N | 28 | 1185.2 | 94 | 8.2 | 34 | 103.7 | 4 |
| P | 271T | 26 | 53.9 | 96 | 20.4 | 32 | 89.1 | 4 |
| E | 272H | 73 | 13.6 | 157 | 23.0 | 53 | 34.8 | 2 |
| E | 272K | 70 | 8.9 | 320 | 20.4 | 118 | 28.7 | 4 |
| E | 272L | 78 | 21.1 | 129 | 3.9 | 71 | 3.1 | 2 |
| E | 272N | 90 | 7.5 | 110 | 33.0 | 71 | 34.6 | 2 |
| E | 272R | 50 | 2.1 | 351 | 3.3 | 102 | 1.2 | 2 |
| V | 279A | 114 | 14.6 | 214 | 5.0 | 106 | 21.2 | 2 |
| V | 279D | 87 | 12.1 | 367 | 0.3 | 98 | 8.5 | 2 |
| V | 279F | 81 | 4.8 | 113 | 14.3 | 106 | 10.0 | 2 |
| V | 279G | 98 | 2.4 | 256 | 11.6 | 109 | 18.0 | 2 |
| V | 279H | 79 | 28.1 | 173 | 29.6 | 127 | 22.7 | 6 |
| V | 279I | 101 | 1.6 | 83 | 1.3 | 100 | 21.0 | 2 |
| V | 279K | 91 | 1.5 | 79 | 26.1 | 106 | 0.7 | 2 |
| V | 279L | 96 | 3.0 | 78 | 13.9 | 100 | 5.7 | 2 |
| V | 279M | 107 | 8.3 | 122 | 3.5 | 91 | 10.3 | 2 |
| V | 279N | 102 | 32.0 | 204 | 19.5 | 85 | 50.2 | 6 |
| V | 279Q | 85 | 28.3 | 181 | 8.0 | 139 | 8.1 | 6 |
| V | 279R | 105 | 4.8 | 130 | 10.7 | 98 | 8.7 | 2 |
| V | 279S | 94 | 29.8 | 242 | 18.3 | 122 | 16.7 | 6 |
| V | 279T | 95 | 15.5 | 265 | 6.9 | 110 | 12.8 | 10 |
| V | 279W | 68 | 24.8 | 162 | 22.8 | 125 | 10.5 | 6 |
| V | 279Y | 82 | 26.8 | 139 | 8.6 | 144 | 13.2 | 6 |
| D | 280A | 111 | 44.9 | 55 | 50.1 | 135 | 28.7 | 2 |
| D | 280K | 137 | 47.6 | 120 | 27.2 | 192 | 33.5 | 2 |
| D | 280T | 108 | na | 60 | 12.6 | 122 | 8.7 | 4 |
| E | 283A | 107 | 2.1 | 126 | 0.2 | 96 | 17.9 | 2 |

TABLE 9-continued

| WT* | Position and Variants* | ADCC | % CV | FcRn pH6.0 | % CV | CDC | % CV | n = |
|---|---|---|---|---|---|---|---|---|
| E | 283D | 84 | 8.4 | 110 | 4.0 | 92 | 10.3 | 2 |
| E | 283F | 74 | 0.1 | 168 | 38.6 | 127 | 20.4 | 2 |
| E | 283G | 93 | 3.1 | 137 | 4.4 | 135 | 8.5 | 2 |
| E | 283H | 87 | 6.1 | 206 | 6.5 | 123 | 15.9 | 2 |
| E | 283I | 106 | 1.9 | 143 | 5.6 | 126 | 12.3 | 2 |
| E | 283K | 109 | 5.8 | 246 | 5.1 | 133 | 8.0 | 2 |
| E | 283L | 92 | 3.1 | 126 | 1.3 | 120 | 0.1 | 2 |
| E | 283M | 112 | 7.4 | 95 | 13.8 | 120 | 2.4 | 2 |
| E | 283N | 102 | 3.8 | 119 | 7.4 | 135 | 23.4 | 6 |
| E | 283P | 97 | 11.9 | 136 | 3.9 | 118 | 11.8 | 2 |
| E | 283Q | 95 | 5.3 | 117 | 8.0 | 122 | 22.9 | 2 |
| E | 283R | 102 | 0.3 | 282 | 8.1 | 144 | 16.7 | 2 |
| E | 283S | 91 | 1.5 | 143 | 11.1 | 119 | 12.3 | 2 |
| E | 283T | 103 | 3.2 | 143 | 12.4 | 108 | 11.0 | 2 |
| E | 283W | 90 | 2.8 | 117 | 2.1 | 159 | 1.3 | 2 |
| E | 283Y | 81 | 6.7 | 142 | 4.1 | 136 | 17.2 | 2 |
| H | 285N | 93 | 2.6 | 202 | 19.8 | 113 | 21.1 | 4 |
| N | 286F | 107 | 7.1 | 307 | 32.3 | 108 | 16.1 | 4 |
| K | 288N | 110 | 8.7 | 162 | 13.2 | 118 | 19.1 | 4 |
| K | 288P | 45 | 1.1 | 119 | 3.0 | 116 | 15.7 | 2 |
| R | 292A | 114 | 2.9 | 85 | 67.5 | 74 | 21.1 | 4 |
| R | 292E | 35 | 21.4 | 65 | 48.5 | 92 | 32.1 | 2 |
| R | 292F | 73 | 16.4 | 64 | 7.6 | 101 | 8.3 | 2 |
| R | 292G | 94 | 2.5 | 60 | 35.9 | 119 | 32.8 | 2 |
| R | 292I | 79 | 1.5 | 56 | 23.6 | 106 | 3.7 | 2 |
| R | 292L | 96 | 3.9 | 68 | 40.0 | 123 | 7.2 | 2 |
| E | 293S | 68 | 7.4 | 101 | 23.0 | 98 | 0.1 | 2 |
| E | 293V | 73 | 12.5 | 127 | 18.0 | 107 | 24.0 | 2 |
| R | 301W | 5 | 105.4 | 119 | 18.1 | 49 | 31.1 | 4 |
| S | 304E | 24 | 32.9 | 101 | 8.7 | 122 | 11.3 | 2 |
| T | 307A | 87 | 4.4 | 233 | 14.5 | 115 | 6.5 | 4 |
| T | 307E | 88 | 7.9 | 492 | 34.6 | 81 | 2.4 | 4 |
| T | 307M | 82 | 5.3 | 302 | 23.7 | 150 | 6.5 | 4 |
| Q | 311A | 106 | 2.4 | 139 | 7.0 | 89 | 28.3 | 2 |
| Q | 311D | 111 | 6.0 | 38 | 22.2 | 83 | 13.6 | 2 |
| Q | 311E | 102 | 1.7 | 46 | 17.7 | 78 | 0.7 | 2 |
| Q | 311F | 89 | 6.9 | 64 | 7.5 | 212 | 20.7 | 2 |
| Q | 311G | 98 | 1.9 | 58 | 21.5 | 92 | 9.6 | 2 |
| Q | 311I | 87 | 8.2 | 437 | 9.6 | 236 | 11.3 | 8 |
| Q | 311K | 80 | 13.4 | 165 | 5.5 | 170 | 9.3 | 6 |
| Q | 311L | 107 | 6.7 | 186 | 9.2 | 191 | 8.1 | 4 |
| Q | 311M | 97 | 7.2 | 387 | 15.0 | 252 | 16.3 | 6 |
| Q | 311N | 115 | 1.9 | 54 | 10.5 | 126 | 23.3 | 2 |
| Q | 311P | 99 | 8.0 | 89 | 300.5 | 172 | 67.9 | 4 |
| Q | 311R | 96 | 8.5 | 14 | 84.5 | 170 | 14.4 | 2 |
| Q | 311S | 86 | 8.8 | 97 | 10.5 | 0 | 92.8 | 2 |
| Q | 311T | 111 | 10.2 | 131 | 14.0 | 168 | 23.4 | 2 |
| Q | 311V | 108 | 1.7 | 558 | 19.5 | 240 | 23.3 | 2 |
| Q | 311W | 104 | 8.2 | 215 | 2.8 | 251 | 18.7 | 4 |
| Q | 311Y | 107 | 3.0 | 94 | 0.3 | 211 | 25.0 | 2 |
| D | 312P | 97 | 1.4 | 546 | 16.1 | 148 | 11.6 | 2 |
| L | 314F | 70 | 7.8 | 42 | 41.2 | 108 | 5.5 | 2 |
| L | 314I | 83 | 13.0 | 86 | 22.7 | 184 | 14.2 | 4 |
| L | 314V | 65 | 14.0 | 21 | 128.8 | 179 | 10.9 | 4 |
| L | 314W | 79 | 11.0 | 5 | 80.2 | 190 | 2.0 | 4 |
| L | 314Y | 87 | 13.6 | 64 | 81.4 | 238 | 3.2 | 4 |
| N | 315F | 83 | 12.8 | 51 | 38.3 | 140 | 15.3 | 2 |
| N | 315K | 108 | 3.5 | 88 | 10.2 | 148 | 8.2 | 2 |
| N | 315L | 112 | 6.2 | 103 | 10.5 | 145 | 5.5 | 2 |
| N | 315P | 62 | 10.2 | 14 | 289.1 | 231 | 9.1 | 4 |
| N | 315R | 96 | 24.4 | 71 | 38.3 | 135 | 0.4 | 2 |
| G | 316F | 54 | 26.0 | 34 | 72.4 | 81 | 10.0 | 2 |
| G | 316K | 77 | 28.8 | 131 | 8.9 | 143 | 8.6 | 2 |
| K | 317P | 54 | 21.5 | 145 | 1.6 | 190 | 4.7 | 2 |
| K | 317T | 99 | 10.9 | 49 | 4.8 | 118 | 4.0 | 2 |
| E | 318N | 123 | 7.2 | 216 | 7.5 | 120 | 7.0 | 4 |
| E | 318P | 120 | 10.8 | 75 | 27.1 | 79 | 17.0 | 4 |
| E | 318T | 109 | 5.7 | 304 | 56.8 | 118 | 10.5 | 4 |
| E | 318V | 116 | 3.4 | 114 | 21.2 | 95 | 11.5 | 4 |
| K | 326W | 74 | 17.9 | 93 | 5.7 | 214 | 9.7 | 2 |
| A | 327T | 4 | 13.4 | 54 | 19.5 | 7 | 206.2 | 2 |
| L | 328V | 76 | 3.2 | 101 | 6.3 | 56 | 13.9 | 2 |
| P | 329Y | 53 | 41.5 | 107 | 13.2 | 25 | 90.3 | 4 |
| A | 330K | 134 | 9.3 | 108 | 51.4 | 43 | 23.9 | 6 |
| A | 330R | 103 | 5.5 | 121 | 39.4 | 31 | 36.6 | 6 |
| I | 332A | 100 | 6.1 | 96 | 27.6 | 130 | 5.0 | 4 |
| I | 332D | 143 | 3.1 | 78 | 33.7 | 151 | 11.5 | 6 |

TABLE 9-continued

| WT* | Position and Variants* | ADCC | % CV | FcRn pH6.0 | % CV | CDC | % CV | n = |
|---|---|---|---|---|---|---|---|---|
| I | 332E | 168 | 10.6 | 86 | 22.2 | 143 | 9.8 | 18 |
| I | 332F | 97 | 14.5 | 108 | 3.4 | 149 | 11.0 | 4 |
| I | 332G | 74 | 19.8 | 94 | 1.4 | 121 | 11.5 | 2 |
| I | 332H | 82 | 4.3 | 129 | 1.1 | 150 | 11.5 | 2 |
| I | 332K | 12 | 114.5 | 146 | 7.0 | 67 | 15.5 | 2 |
| I | 332L | 94 | 0.9 | 127 | 2.6 | 154 | 5.1 | 2 |
| I | 332M | 98 | 2.2 | 128 | 16.1 | 178 | 6.6 | 2 |
| I | 332N | 95 | 15.3 | 92 | 16.1 | 137 | 5.1 | 4 |
| I | 332Q | 99 | 8.4 | 98 | 7.9 | 148 | 8.5 | 6 |
| I | 332R | 12 | 135.5 | 114 | 7.2 | 88 | 30.0 | 2 |
| I | 332S | 96 | 4.9 | 263 | 64.1 | 177 | 16.5 | 2 |
| I | 332T | 112 | 7.5 | 100 | 5.3 | 124 | 4.5 | 4 |
| I | 332V | 109 | 1.1 | 115 | 19.5 | 147 | 25.1 | 2 |
| I | 332W | 81 | 16.8 | 123 | 3.7 | 150 | 9.7 | 2 |
| I | 332Y | 93 | 13.1 | 93 | 12.3 | 152 | 5.3 | 2 |
| A | 339D | 131 | 10.4 | 80 | 26.4 | 183 | 20.3 | 6 |
| A | 339E | 100 | 0.4 | 75 | 4.2 | 91 | 0.1 | 2 |
| A | 339F | 104 | 3.3 | 120 | 24.6 | 217 | 8.5 | 6 |
| A | 339G | 107 | 3.7 | 67 | 6.5 | 118 | 0.3 | 2 |
| A | 339H | 114 | 23.4 | 107 | 10.0 | 136 | 0.5 | 2 |
| A | 339I | 136 | 14.6 | 80 | 30.6 | 205 | 22.8 | 6 |
| A | 339K | 129 | 24.2 | 83 | 29.0 | 201 | 21.0 | 6 |
| A | 339L | 97 | 8.7 | 83 | 9.8 | 104 | 8.7 | 2 |
| A | 339M | 115 | 6.8 | 111 | 7.2 | 57 | 8.8 | 2 |
| A | 339N | 110 | 6.3 | 146 | 3.5 | 240 | 17.5 | 4 |
| A | 339Q | 128 | 15.8 | 102 | 19.8 | 138 | 11.0 | 6 |
| A | 339R | 117 | 14.4 | 82 | 13.4 | 128 | 2.1 | 2 |
| A | 339S | 124 | 13.0 | 95 | 23.6 | 170 | 22.5 | 6 |
| A | 339T | 142 | 14.2 | 138 | 6.2 | 220 | 20.2 | 10 |
| A | 339W | 92 | 13.4 | 156 | 11.4 | 243 | 10.6 | 6 |
| A | 339Y | 97 | 17.0 | 92 | 19.8 | 265 | 21.9 | 10 |
| G | 341D | 62 | 6.9 | 52 | 37.8 | 172 | 3.5 | 2 |
| G | 341E | 73 | 6.9 | 50 | 18.1 | 161 | 3.8 | 2 |
| G | 341F | 24 | 100.8 | 52 | 41.9 | 227 | 14.7 | 6 |
| G | 341H | 54 | 9.3 | 65 | 63.7 | 245 | 16.0 | 6 |
| G | 341I | 44 | 15.5 | 36 | 17.2 | 173 | 5.3 | 2 |
| G | 341K | 77 | 3.9 | 67 | 18.9 | 161 | 2.6 | 2 |
| G | 341L | 64 | 24.3 | 54 | 19.8 | 171 | 4.2 | 2 |
| G | 341M | 55 | 39.8 | 79 | 9.7 | 232 | 11.1 | 6 |
| G | 341N | 83 | 9.1 | 53 | 17.0 | 162 | 9.5 | 2 |
| G | 341P | 35 | 47.2 | 127 | 9.9 | 228 | 16.2 | 6 |
| G | 341Q | 59 | 18.7 | 72 | 1.0 | 166 | 7.7 | 2 |
| G | 341R | 59 | 14.9 | 78 | 7.4 | 168 | 7.5 | 2 |
| G | 341S | 65 | 26.6 | 55 | 12.2 | 224 | 9.2 | 6 |
| G | 341T | 0 | 866.0 | 68 | 54.0 | 176 | 10.0 | 2 |
| G | 341V | 65 | 171.0 | 69 | 15.0 | 213 | 9.6 | 4 |
| G | 341W | 14 | 25.8 | 76 | 8.9 | 178 | 8.7 | 2 |
| G | 341Y | 26 | 24.5 | 54 | 5.2 | 184 | 14.3 | 2 |
| P | 343A | 75 | 18.6 | 110 | 37.7 | 143 | 5.9 | 2 |
| P | 343D | 69 | 11.5 | 102 | 7.9 | 157 | 18.3 | 2 |
| P | 343E | 65 | 34.9 | 345 | 6.4 | 157 | 17.6 | 2 |
| P | 343F | 74 | 20.6 | 89 | 13.0 | 99 | 1058.4 | 4 |
| P | 343G | 75 | 29.1 | 110 | 14.9 | 244 | 11.1 | 6 |
| P | 343H | 78 | 33.8 | 191 | 1.2 | 159 | 3.1 | 2 |
| P | 343I | 92 | 26.8 | 114 | 16.7 | 86 | 10.5 | 2 |
| P | 343K | 74 | 37.7 | 232 | 2.6 | 185 | 9.1 | 2 |
| P | 343L | 63 | 17.2 | 125 | 3.8 | 127 | 5.6 | 2 |
| P | 343M | 60 | 35.1 | 83 | 13.7 | 134 | 18.7 | 4 |
| P | 343N | 67 | 8.9 | 105 | 19.9 | 196 | 18.2 | 2 |
| P | 343Q | 72 | 0.5 | 442 | 14.0 | 178 | 3.0 | 2 |
| P | 343R | 94 | 1.3 | 198 | 10.4 | 179 | 9.9 | 4 |
| P | 343S | 84 | 7.5 | 101 | 14.3 | 207 | 11.9 | 6 |
| P | 343T | 69 | 4.2 | 126 | 16.1 | 151 | 4.4 | 2 |
| P | 343V | 70 | 1.9 | 77 | 5.3 | 107 | 12.0 | 2 |
| P | 343W | 48 | 22.3 | 56 | 6.4 | 194 | 17.9 | 2 |
| P | 343Y | 63 | 9.9 | 112 | 7.2 | 270 | 14.4 | 6 |
| Y | 373A | 56 | 3.7 | 33 | 15.0 | 121 | 28.7 | 2 |
| Y | 373D | 74 | 17.7 | 74 | 32.5 | 227 | 10.2 | 6 |
| Y | 373E | 41 | 23.6 | 106 | 20.8 | 151 | 19.5 | 2 |
| Y | 373F | 76 | 2.6 | 110 | 12.7 | 117 | 1.0 | 2 |
| Y | 373G | 39 | 21.6 | 38 | 25.4 | 75 | 33.7 | 2 |
| Y | 373H | 79 | 34.2 | 100 | 13.9 | 169 | 8.2 | 4 |
| Y | 373I | 65 | 9.0 | 73 | 14.0 | 154 | 6.4 | 2 |
| Y | 373K | 76 | 12.2 | 70 | 2.9 | 246 | 6.9 | 6 |
| Y | 373L | 76 | 21.4 | 66 | 17.0 | 189 | 6.2 | 6 |
| Y | 373M | 78 | 1.2 | 53 | 25.8 | 115 | 3.2 | 2 |
| Y | 373N | 64 | 21.5 | 61 | 23.3 | 148 | 12.1 | 2 |

TABLE 9-continued

| WT* | Position and Variants* | ADCC | % CV | FcRn pH6.0 | % CV | CDC | % CV | n = |
|---|---|---|---|---|---|---|---|---|
| Y | 373Q | 63 | 11.0 | 55 | 24.7 | 158 | 17.7 | 2 |
| Y | 373R | 81 | 20.5 | 107 | 24.1 | 221 | 4.0 | 6 |
| Y | 373S | 52 | 3.7 | 74 | 1.9 | 72 | 24.8 | 2 |
| Y | 373T | 70 | 3.0 | 82 | 16.6 | 151 | 5.7 | 2 |
| Y | 373V | 73 | 2.1 | 69 | 14.3 | 115 | 1.1 | 2 |
| Y | 373W | 77 | 23.3 | 75 | 18.5 | 237 | 20.8 | 6 |
| S | 375R | 69 | 10.9 | 595 | 15.9 | 166 | 1.1 | 2 |
| D | 376A | 111 | 18.2 | 155 | 26.7 | 180 | 5.2 | 2 |
| D | 376E | 85 | 12.3 | 82 | 29.5 | 98 | 13.5 | 2 |
| D | 376F | 84 | 7.3 | 116 | 12.6 | 119 | 8.6 | 2 |
| D | 376G | 73 | 3.1 | 135 | 3.9 | 164 | 0.6 | 2 |
| D | 376H | 74 | 16.1 | 81 | 18.6 | 118 | 5.6 | 2 |
| D | 376I | 100 | 14.1 | 144 | 7.2 | 101 | 50.5 | 10 |
| D | 376L | 88 | 16.7 | 78 | 3.0 | 142 | 3.2 | 2 |
| D | 376M | 86 | 21.6 | 129 | 1.4 | 91 | 15.1 | 2 |
| D | 376N | 93 | 14.5 | 94 | 24.2 | 173 | 14.9 | 4 |
| D | 376P | 85 | 15.1 | 203 | 12.9 | 153 | 19.6 | 6 |
| D | 376Q | 88 | 5.0 | 116 | 22.7 | 176 | 19.9 | 4 |
| D | 376R | 95 | 6.0 | 103 | 12.3 | 166 | 4.6 | 2 |
| D | 376S | 85 | 21.4 | 134 | 27.3 | 209 | 25.3 | 2 |
| D | 376T | 102 | 20.0 | 160 | 11.2 | 224 | 10.1 | 6 |
| D | 376V | 112 | 8.1 | 251 | 15.0 | 210 | 11.1 | 12 |
| D | 376W | 53 | 22.0 | 1 | 1719.9 | 89 | 34.8 | 2 |
| D | 376Y | 78 | 4.2 | 53 | 25.8 | 98 | 39.9 | 2 |
| I | 377G | 107 | 2.4 | 76 | 28.8 | 92 | 7.6 | 2 |
| I | 377K | 117 | 10.0 | 167 | 27.7 | 90 | 11.3 | 4 |
| I | 377P | 99 | 11.3 | 98 | 32.4 | 245 | 6.5 | 4 |
| A | 378D | 98 | 6.6 | 163 | 13.9 | 19 | 91.9 | 6 |
| A | 378N | 101 | 7.1 | 180 | 3.0 | 90 | 30.7 | 2 |
| V | 379N | 96 | 19.5 | 74 | 39.0 | 204 | 5.5 | 4 |
| V | 379Q | 113 | 3.2 | 85 | 27.3 | 218 | 4.1 | 4 |
| V | 379S | 80 | 18.4 | 86 | 13.4 | 137 | 1.4 | 2 |
| V | 379T | 101 | 16.6 | 109 | 14.9 | 237 | 2.2 | 4 |
| E | 380A | 106 | 3.2 | 152 | 28.8 | 139 | 4.2 | 2 |
| E | 380D | 102 | 2.1 | 73 | 44.2 | 78 | 0.7 | 2 |
| E | 380N | 111 | 7.7 | 142 | 19.0 | 139 | 7.3 | 2 |
| E | 380S | 110 | 8.5 | 230 | 24.1 | 131 | 0.1 | 2 |
| E | 380T | 100 | 1.2 | 172 | 11.0 | 115 | 4.8 | 2 |
| E | 382A | 110 | 6.0 | 103 | 7.8 | 82 | 29.6 | 2 |
| E | 382D | 95 | 0.8 | 73 | 25.7 | 80 | 34.2 | 2 |
| E | 382F | 121 | 13.8 | 222 | 16.6 | 67 | 28.2 | 6 |
| E | 382H | 89 | 17.9 | 135 | 2.8 | 84 | 20.4 | 2 |
| E | 382I | 109 | 6.4 | 131 | 6.2 | 219 | 5.4 | 6 |
| E | 382K | 96 | 2.6 | 153 | 30.2 | 92 | 15.6 | 4 |
| E | 382L | 93 | 16.5 | 126 | 11.1 | 156 | 7.7 | 2 |
| E | 382M | 89 | 14.6 | 135 | 8.6 | 126 | 20.3 | 2 |
| E | 382N | 99 | 1.1 | 137 | 5.2 | 69 | 4.5 | 2 |
| E | 382P | 85 | 16.8 | 122 | 22.0 | 69 | 14.6 | 2 |
| E | 382Q | 105 | 12.2 | 162 | 12.0 | 140 | 19.3 | 2 |
| E | 382R | 104 | 8.4 | 165 | 2.7 | 85 | 3.0 | 4 |
| E | 382S | 85 | 2.9 | 151 | 10.0 | 75 | 4.1 | 2 |
| E | 382T | 89 | 10.2 | 172 | 5.2 | 109 | 30.0 | 2 |
| E | 382V | 83 | 32.5 | 173 | 6.2 | 167 | 0.4 | 2 |
| E | 382W | 97 | 10.5 | 172 | 5.2 | 73 | 1.9 | 2 |
| E | 382Y | 105 | 11.5 | 188 | 14.5 | 78 | 3.3 | 4 |
| G | 385E | 108 | 5.5 | 98 | 18.8 | 0 | 1586.3 | 2 |
| G | 385P | 100 | 3.2 | 101 | 23.2 | 82 | 15.8 | 2 |
| Q | 386K | 96 | 9.5 | 115 | 4.8 | 266 | 1.6 | 4 |
| F | 423N | 107 | 8.5 | 158 | 2.1 | 48 | 27.5 | 2 |
| S | 424H | 116 | 29.8 | 97 | 7.3 | 58 | 9.3 | 2 |
| S | 424M | 91 | 3.5 | 60 | 60.0 | 75 | 14.4 | 2 |
| S | 424V | 103 | 9.3 | 57 | 35.4 | 115 | 10.5 | 4 |
| S | 426D | 105 | 24.3 | 65 | 10.0 | 318 | 12.7 | 4 |
| S | 426L | 91 | 35.3 | 117 | 14.3 | 193 | 20.4 | 4 |
| V | 427N | 108 | 5.5 | 192 | 5.9 | 64 | 23.1 | 2 |
| H | 429A | 44 | 81.7 | 61 | 11.4 | 147 | 1.9 | 2 |
| H | 429F | 70 | 11.1 | 77 | 16.5 | 288 | 12.8 | 4 |
| H | 429M | 103 | 0.7 | 83 | 12.2 | 173 | 3.2 | 2 |
| E | 430A | 100 | 8.3 | 179 | 6.6 | 204 | 7.1 | 2 |
| E | 430D | 96 | 8.2 | 44 | 25.5 | 190 | 4.6 | 4 |
| E | 430F | 111 | 13.0 | 218 | 19.4 | 203 | 8.1 | 2 |
| E | 430G | 97 | 7.8 | 131 | 10.6 | 252 | 7.5 | 6 |
| E | 430H | 91 | 7.7 | 192 | 8.0 | 227 | 4.2 | 6 |
| E | 430I | 87 | 19.3 | 308 | 6.6 | 297 | 17.2 | 6 |
| E | 430K | 66 | 9.5 | 131 | 12.6 | 203 | 16.0 | 4 |
| E | 430L | 98 | 33.3 | 242 | 8.7 | 263 | 10.6 | 6 |
| E | 430M | 102 | 16.1 | 195 | 8.7 | 227 | 4.6 | 6 |

TABLE 9-continued

| WT* | Position and Variants* | ADCC | % CV | FcRn pH6.0 | % CV | CDC | % CV | n = |
|---|---|---|---|---|---|---|---|---|
| E | 430N | 82 | 24.6 | 171 | 13.0 | 162 | 2.2 | 2 |
| E | 430P | 103 | 13.1 | 86 | 16.7 | 254 | 23.5 | 8 |
| E | 430Q | 79 | 8.3 | 320 | 12.8 | 97 | 4.9 | 8 |
| E | 430R | 75 | 7.5 | 249 | 6.6 | 227 | 7.9 | 8 |
| E | 430S | 88 | 30.1 | 183 | 3.4 | 221 | 18.5 | 2 |
| E | 430T | 82 | 22.9 | 137 | 23.7 | 249 | 8.2 | 6 |
| E | 430V | 79 | 35.6 | 281 | 7.0 | 276 | 17.5 | 6 |
| E | 430W | 78 | 8.3 | 11 | 95.0 | 171 | 5.4 | 2 |
| E | 430Y | 77 | 44.5 | 126 | 12.5 | 231 | na | 2 |
| A | 431H | 81 | 44.0 | 151 | 11.5 | 236 | na | 2 |
| A | 431K | 98 | 26.6 | 176 | 4.4 | 113 | 25.0 | 2 |
| A | 431P | 62 | 12.0 | 29 | 13.8 | 210 | 8.0 | 2 |
| L | 432R | 58 | 23.1 | 38 | 15.6 | 175 | 13.3 | 2 |
| L | 432S | 58 | 55.4 | 70 | 3.6 | 124 | 0.2 | 2 |
| N | 434F | na | na | 1008 | 1.4 | na | na | 4 |
| N | 434G | 105 | 17.9 | 358 | 20.2 | 26 | 128.9 | 4 |
| N | 434H | 90 | 12.9 | 855 | 20.4 | 57 | 9.1 | 6 |
| N | 434I | 81 | 9.3 | 6 | 725.4 | 73 | 8.9 | 2 |
| N | 434W | 108 | 6.6 | 1335 | 18.8 | 138 | 1.7 | 2 |
| N | 434Y | 106 | 7.7 | 1615 | 38.8 | 291 | 15.5 | 4 |
| Y | 436I | 119 | 18.0 | 194 | 24.2 | 35 | 8.7 | 2 |
| Y | 436L | 112 | 27.2 | 172 | 8.1 | 90 | 16.3 | 4 |
| Y | 436T | 90 | 35.0 | 115 | 7.2 | 48 | 20.3 | 2 |
| Q | 438G | 93 | 32.1 | 98 | 14.4 | 68 | 26.2 | 2 |
| Q | 438K | 99 | 31.7 | 169 | 12.3 | 116 | 43.0 | 2 |
| Q | 438L | 94 | 32.5 | 200 | 14.7 | 190 | 5.5 | 4 |
| Q | 438T | 96 | 37.4 | 126 | 9.5 | 56 | 26.8 | 2 |
| Q | 438W | 93 | 32.5 | 164 | 8.2 | 126 | 1.7 | 2 |
| K | 439E | 103 | 28.9 | 94 | 9.0 | 53 | 40.3 | 2 |
| K | 439H | 91 | 37.3 | 99 | 0.9 | 77 | 17.8 | 2 |
| K | 439Q | 90 | 38.2 | 74 | 0.9 | 64 | 26.5 | 2 |
| S | 440A | 79 | 42.3 | 82 | 2.0 | 85 | 22.5 | 2 |
| S | 440D | 82 | 18.4 | 72 | 4.7 | 99 | 9.4 | 2 |
| S | 440E | 104 | 4.0 | 73 | 2.8 | 87 | 35.3 | 2 |
| S | 440F | 111 | 16.1 | 87 | 8.2 | 73 | 18.5 | 2 |
| S | 440G | 106 | 1.9 | 101 | 8.1 | 83 | 8.5 | 2 |
| S | 440H | 108 | 2.1 | 110 | 2.1 | 96 | 18.3 | 2 |
| S | 440I | 121 | 1.9 | 96 | 6.2 | 86 | 2.6 | 2 |
| S | 440K | 116 | 16.7 | 132 | 7.8 | 71 | 26.4 | 4 |
| S | 440L | 112 | 6.4 | 126 | 2.2 | 77 | 4.5 | 4 |
| S | 440M | 84 | 51.0 | 80 | 8.2 | 81 | 20.6 | 2 |
| S | 440N | 78 | 34.3 | 82 | 25.4 | 108 | 15.8 | 2 |
| S | 440Q | 73 | 43.1 | 81 | 33.5 | 132 | 16.6 | 2 |
| S | 440R | 91 | 11.3 | 88 | 16.2 | 85 | 29.8 | 2 |
| S | 440T | 89 | 2.1 | 71 | 39.0 | 115 | 17.4 | 2 |
| S | 440V | 85 | 11.3 | 98 | 18.7 | 110 | 16.4 | 2 |
| S | 440W | 114 | 17.6 | 85 | 13.8 | 132 | 14.8 | 2 |
| S | 440Y | 109 | 6.8 | 100 | 14.2 | 224 | 14.1 | 16 |
| S | 442K | 80 | 51.9 | 138 | 4.5 | 100 | 11.1 | 2 |

Na = not available or not done
*e.g., L235A indicates an Fc in which the leucine present at Fc amino acid number 235 (according to EU numbering) has been substituted with an alanine residue tested here: the Fc region is an IgG1 Fc, the antibody is anti-CD20 antibody

TABLE 10

Combination Variants - ADCC

| Variant | Average ADCC as % of wt | CV % | n = |
|---|---|---|---|
| Wild type | 100 | 2.42 | 2 |
| 247A, 339D | 71.50 | 0.50 | 2 |
| 247F, 339D | 134.95 | 2.54 | 2 |
| 247H, 339D | 118.45 | 8.46 | 4 |
| 247I, 339D | 187.21 | 20.45 | 2 |
| 247L, 339D | 156.73 | 3.30 | 2 |
| 247T, 339D | 126.46 | 4.71 | 2 |
| 247Y, 339D | 121.93 | 4.58 | 2 |
| 247A, 339H | 125.35 | 0.60 | 2 |
| 247F, 339H | 101.54 | 4.53 | 2 |
| 247H, 339H | 114.24 | 4.91 | 2 |
| 247I, 339H | 126.94 | 5.22 | 2 |
| 247L, 339H | 120.92 | 2.44 | 2 |
| 247T, 339H | 97.96 | 5.71 | 2 |
| 247Y, 339H | 74.75 | 2.43 | 2 |
| 247A, 339I | 96.95 | 3.05 | 2 |
| 247F, 339I | 116.53 | 5.52 | 2 |
| 247H, 339I | 108.27 | 2.97 | 2 |
| 247I, 339I | −4.07 | −47.26 | 2 |
| 247L, 339I | 109.76 | 5.95 | 2 |
| 247T, 339I | 5.48 | 9.51 | 2 |
| 247Y, 339I | 100.84 | 9.58 | 2 |
| 247A, 339K | 86.90 | 13.51 | 2 |
| 247F, 339K | 105.85 | 10.11 | 2 |
| 247H, 339K | 97.59 | 7.67 | 2 |
| 247I, 339K | 97.41 | 14.89 | 2 |

TABLE 10-continued

Combination Variants - ADCC

| Variant | Average ADCC as % of wt | CV % | n = |
|---|---|---|---|
| 247L, 339K | 104.36 | 7.07 | 2 |
| 247T, 339K | 83.02 | 6.07 | 2 |
| 247Y, 339K | 95.79 | 3.69 | 2 |
| 332E | 180.96 | 0.72 | 2 |
| 247A, 339N | 83.60 | 9.91 | 2 |
| 247F, 339N | 100.36 | 8.95 | 2 |
| 247H, 339N | 86.70 | 7.62 | 2 |
| 247I, 339N | 119.62 | 13.07 | 2 |
| 247T, 339N | 114.38 | 4.83 | 4 |
| 247Y, 339N | 113.18 | 1.50 | 2 |
| 332E | 187.19 | 9.53 | 2 |
| 247A, 339Q | 69.94 | 8.45 | 2 |
| 247F, 339Q | 130.42 | 2.35 | 2 |
| 247H, 339Q | 138.96 | 1.32 | 2 |
| 247I, 339Q | 146.44 | 2.27 | 2 |
| 247L, 339Q | 140.50 | 4.58 | 2 |
| 247T, 339Q | 119.70 | 4.03 | 2 |
| 247Y, 339Q | 109.40 | 2.24 | 2 |
| 247A, 339R | 68.57 | 8.33 | 2 |
| 247F, 339R | 114.38 | 11.85 | 2 |
| 247H, 339R | 105.46 | 9.89 | 2 |
| 247I, 339R | 124.96 | 16.31 | 2 |
| 247L, 339R | 119.77 | 12.03 | 2 |
| 247T, 339R | 109.42 | 12.17 | 2 |
| 247Y, 339R | 98.58 | 13.09 | 2 |
| 247L, 339T | 148.48 | 7.08 | 4 | wt = wild-type
CV % =
n = number of samples measured and averaged

TABLE 11

Combination Variants with ADCC Enhancement

| Fc Variant | ADCC EC50 (ng/ml) |
|---|---|
| Wild type | 6.8 |
| 247L | 2.2 |
| 330K | 3.1 |
| 332E | 1.5 |
| 339T | 3.8 |
| 247L, 330K | 1.5 |
| 247L, 332E | 0.73 |
| 247L, 339T | 2.0 |
| 330K, 332E | 0.73 |
| 330K, 339T | 2.0 |
| 332E, 339T | 1.0 |
| 247L, 332E, 339T | 0.75 |
| 247L, 330K, 332E | 0.25 |
| 247L, 330K, 339T | 1.5 |
| 330K, 332E, 339T | 0.25 |
| 247L, 330K, 332E, 339T | 0.25 |

* ADCC activities were calculated from titration curves

TABLE 12

Combination Variants

| Mutation | ADCC | CV % | FcRn6.0 | CV % | CDC | CV % | n = |
|---|---|---|---|---|---|---|---|
| Wild Type | 100 | | 100 | | 100 | | |
| 247H339D | 118 | 8.5 | N/D | N/D | N/D | N/D | 4 |
| 247L251F330R332E | 184 | 13.3 | 50 | 5.9 | 43 | 1.3 | 2 |
| 247L251F376I | 77 | 29.7 | 61 | 8.7 | 124 | 11.3 | 2 |
| 247L332E | 168 | 7.3 | 78 | 4.9 | 65 | 6.2 | 6 |
| 247L332E376I | 137 | 8.1 | 74 | 8.0 | 76 | 4.3 | 4 |
| 247T339N | 114 | 4.8 | N/D | N/D | N/D | N/D | 4 |
| 251F332E | 147 | 12.4 | 72 | 2.2 | 196 | 2.6 | 6 |
| 251F332E376I | 136 | 15.9 | 68 | 5.0 | 160 | 10.9 | 4 |
| 251F376I | 114 | 8.1 | 66 | 2.9 | 102 | 9.4 | 4 |
| 256P311I | 107 | 0.2 | 268 | 1.2 | 357 | 10.0 | 2 |
| 256P314Y332E440Y | 146 | 3.1 | 86 | 19.5 | 190 | 4.5 | 2 |
| 256P314Y440Y | 112 | 22.6 | 79 | 3.0 | 226 | 9.4 | 2 |
| 256P332E | 174 | 16.3 | 121 | 8.2 | 189 | 3.9 | 4 |
| 256P332E440Y | 184 | 25.4 | 117 | 6.5 | 230 | 10.0 | 2 |
| 256P430Q | 109 | 2.6 | 150 | 5.3 | 354 | 3.3 | 4 |
| 256P434H | 105 | 1.2 | 342 | 3.1 | 299 | 2.9 | 2 |
| 256P440Y | 169 | 19.7 | 122 | 0.7 | 247 | 26.6 | 2 |
| 257I311I | 52 | 7.7 | 409 | 3.9 | 61 | 6.7 | 2 |
| 257I311I434H | 48 | 12.2 | 553 | 4.9 | 75 | 8.8 | 6 |
| 257I430Q | 26 | 8.1 | 304 | 0.6 | 55 | 12.9 | 4 |
| 257I434H | 67 | 7.0 | 472 | 6.3 | 61 | 14.0 | 4 |
| 268D332E | 137 | 12.4 | 92 | 13.7 | 128 | 4.1 | 4 |
| 268E332E | 178 | 5.3 | 88 | 2.0 | 160 | 4.7 | 4 |
| 272R279L | 56 | 0.2 | 156 | 1.2 | 72 | 5.1 | 2 |
| 279A288N | 107 | 3.9 | N/D | N/D | N/D | N/D | 4 |
| 279A288N311T318V | 110 | 9.0 | N/D | N/D | N/D | N/D | 4 |
| 279A288N318N | 110 | 5.4 | N/D | N/D | N/D | N/D | 4 |
| 279A288N318T | 116 | 5.1 | N/D | N/D | N/D | N/D | 4 |
| 279A288N318V | 118 | 8.8 | N/D | N/D | N/D | N/D | 4 |
| 279A311T318T | 110 | 7.9 | N/D | N/D | N/D | N/D | 4 |
| 288N311T318T | 115 | 9.9 | N/D | N/D | N/D | N/D | 4 |

TABLE 12-continued

Combination Variants

| Mutation | ADCC | CV % | FcRn6.0 | CV % | CDC | CV % | n = |
|---|---|---|---|---|---|---|---|
| 311T318T | 107 | 5.3 | N/D | N/D | N/D | N/D | 4 |
| 314Y332E440Y | 156 | 5.4 | 82 | 0.9 | 155 | 0.0 | 2 |
| 314Y440Y | 125 | 12.7 | 78 | 8.5 | 108 | 2.6 | 2 |
| 330K332D | 179 | 2.9 | 88 | 8.3 | 43 | 0.3 | 2 |
| 330K332E | 202 | 5.6 | 94 | 0.0 | 42 | 1.0 | 2 |
| 330R332D | 152 | 6.3 | 88 | 6.3 | 44 | 1.5 | 2 |
| 330R332E | 161 | 4.3 | 94 | 2.1 | 59 | 4.0 | 4 |
| 332E376I | 132 | 8.6 | 102 | 7.6 | 193 | 5.2 | 6 |
| 332E376V | 139 | 1.9 | 132 | 3.5 | 261 | 8.6 | 6 |
| 332E440Y | 203 | 13.0 | 94 | 5.7 | 159 | 5.9 | 4 |
| 343R345D | 121 | 16.0 | 143 | 1.6 | 291 | 3.3 | 2 |
| 376V430Q | 92 | 1.5 | 212 | 4.2 | 256 | 12.2 | 4 |
| 376V430R | 84 | 2.7 | 188 | 9.1 | 191 | 1.0 | 2 |
| 376V434H | 97 | 3.3 | 382 | 3.3 | 95 | 6.1 | 4 |

TABLE 13

Combination Variants

| Mutation | FcRn6.0 | CV % | n = |
|---|---|---|---|
| Wild Type | 100 | | |
| 258D272R | 382.8 | 8.2 | 2 |
| 258D283R | 411.1 | 3.7 | 2 |
| 258D286F | 445.0 | 1.7 | 2 |
| 258D307E | 237.1 | 4.8 | 2 |
| 258D311I | 522.0 | 7.0 | 2 |
| 258D376V | 415.1 | 4.3 | 2 |
| 272R283R | 439.3 | 21.7 | 2 |
| 272R286F | 338.4 | 8.9 | 2 |
| 272R311I | 396.1 | 14.4 | 2 |
| 272R376V | 368.7 | 8.1 | 2 |
| 279D307E | 522.4 | 8.8 | 2 |
| 283R307E | 400.2 | 9.1 | 2 |
| 283R311I | 531.3 | 6.1 | 2 |
| 283R376V | 474.8 | 1.1 | 2 |
| 286F307E | 431.2 | 3.8 | 2 |
| 286F311I | 412.3 | 0.0 | 2 |
| 286F376V | 348.9 | 1.5 | 2 |
| 307E376V | 480.1 | 4.3 | 2 |
| 311I376V | 413.5 | 39.1 | 2 |

Example 2

Characterization of CDC Activity of Variants

This example describes how CDC activity of various variant Fc regions is determined.

This assay is carried out using human complement (Quidel Corp., cat#AI 13) on 15 Ramos (RA #1) cell (ATCC Catalog No. CRL-1596). Ramos cells are cultured in Gibco RPMI1640 media containing 10% FBS at 37° C. and 5% C02. The day before the assay, cells are seeded at $1\times10^6$ cells in a T175 flask. The following day, the cells are resuspended to $3.57\times10^5$ cells/ml in RPM11640 without phenol red containing 1% FBS. Distribute 70 µl cells per well to a Costar 3917 flat bottom plate. For titration curve, IgG with a variant Fc region wis prepared in a 3-fold serial dilution in RPMI1640 media. For single-point library screening assay, transiently expressed IgG variant in culture supernatant is normalized to 1 µg/ml in mock media. Thirty microliter of variant IgG (i.e., 200 ng/ml final concentration) and 50 µl of human complement (Quidel Corp., cat#A113) 1:5 diluted in RPMI 1640+ 1% FBS is added to the target cell and mixed well by gentle pipetting. The plates are incubated at 37° C. in the presence of 5% CO2 for 1.5 hours. After addition of 15 µl/well of Alamar Blue (Serotec, cat#BUF012B) the incubation continues overnight. Then the fluorescence signal is measured by PerkinElmer's EnVision 2100 multilabel reader with excitation at 560 nm and emission at 590 nm.

ii. Data Analysis,

All single-point assays are performed in duplicate. Each assay plate contains controls for spontaneous target cell lysis by human complement in the absence of IgG and target cell maximal lysis in the presence of 1% Triton X-100. Three wild type controls are included on each assay plate and the CDC assay signal averaged. The background value, obtained from the spontaneous lysis control, is subtracted from each sample. The data are converted from fluorescence signals to percentage of specific-lysis based upon spontaneous and maximal lysis controls. The percentage of specific-lysis is calculated from the following equation: percentage specific lysis=(experimental fluorescence signal−spontaneous signal)/(maximal lysis signal−spontaneous signal)×100. The percentage of Fc variant activity over the average of three wild type controls is then calculated. The percentage activities over wild type for duplicate assay plates are averaged and the standard deviation between individual assay plates is calculated.

Example 3

Characterization of Binding to FcRn

This Example describes assays for Fc neonatal receptor (FcRn) binding to IgG with a variant Fc region.

A U-bottom 96-well ELISA plate is coated (Costar) with 50 µl/well of 2 µg/ml Neutravidin (Pierce Biotechnology, Cat#3 1000) in 50 mM Carbonate buffer (pH 9.3) at 4° C. overnight. Unbound NeutraAvidin is removed and the plate is washed three times with PBST (PBS containing 0.1% Tween 20). Fifty microliters of biotin-labeled soluble FcRn at 2.5 µg/ml in PBS is applied per well and incubated at room temperature for 1 hr. Then 75 µl of casein blocking buffer (Pierce Biotechnology, Cat#37528) is added to the plate for 1 hour. The ELISA plate is then washed with PBST and incubated with 50 µl/well of variant IgG. For the titration curve, IgG to be tested is prepared by a 3-fold serial dilution in FcRn-binding buffer (100 mM NaPO4, 0.05% Tween-20, optionally at different pHs (from 6.0 to 7.4)). For single-point screening, transient expressed variant IgG in culture supernatant is normalized to a final concentration of 50 ng/ml and pH adjusted with FcRn binding buffer to 6.0. In the following steps, FcRn-binding buffer at corresponding pH is used to wash the plate and to dilute reagents. The binding reaction is carried out at room temperature for 1 hr. After three washes, bound IgG is detected by goat (Fab')$_2$ anti-human-Fab-HRP conjugate for 1 hr. HRP activity is developed in Pierce's HRP substrate (Turbo TMB-ELISA, Cat#34022) for 5-30 minutes. The reaction is stopped by addition of 50 μl of 2 M H$_2$SO$_4$ and the absorbance at 450 nm is read with a VMAX microplate reader (Molecular Devices).

Example 4

Anti-CD20-I332E Fc Variant Human Therapy

In vitro studies and murine tumor models (Clynes R A, et al. Nat. Med. 6:443 (2000)) provide evidence that ADCC plays a role in the anti-tumor effects of anti-CD20 antibodies, such as RITUXAN. Human patients may be treated with anti-CD20-I332E Fc variant antibodies or RITUXAN, in a manner similar to that disclosed in Cartron et al., Blood 99:754 (2002). For example, patients presenting with stage II to IV disease according to the Ann-Arbor classification, having at least one measurable disease site, and low tumor burden according to the GELF criteria, could be treated with a total of four approximately 375 mg/m$^2$ doses of an anti-CD20-Fc variant or with RITUXAN administered by intravenous infusion (days 1, 8, 15, and 22). The primary efficacy end point is the objective response rate, i.e., the proportion of patients achieving either complete remission (CR), unconfirmed CR (Cru), or partial response (PR) according to criteria recently proposed by an international expert committee. Clinical response may be evaluated at month two (M2). Patients may also be evaluated for progression at 1 year (M12).

The objective response rates at M2 and M12 for patients treated with RITUXAN or anti-CD20-Fc variant can be compared such that the improved ADCC activities provided by an Fc variant may be quantified. This same example could be repeated with other anti-CD20 variants (see, e.g., Tables 1-10 herein).

Additionally, the enhanced potency of the variants may permit different routes of administration, less frequent injections, and/or administration of smaller doses. All publications and patents mentioned in the above specification. Various modifications and variations of the described method and system of the invention will be apparent to those skilled in the art without departing from the scope and spirit of the invention. Although the invention has been described in connection with specific preferred embodiments, the invention as claimed should not be unduly limited to such specific embodiments. Indeed, various modifications of the described modes for carrying out the invention which are obvious to those skilled in chemistry, and molecular biology or related fields are intended to be within the scope of the following claims.

We claim:

1. An anti-CD20 antibody comprising a light chain and a heavy chain, wherein the amino acid sequence of the light chain consists of SEQ ID NO: 29 and the amino acid sequence of the heavy chain consists of SEQ ID NO: 31.

2. A pharmaceutical composition comprising the anti-CD20 antibody of claim 1 and a pharmaceutically acceptable carrier.

3. A method for treating lymphoma in a human comprising administering to the human a therapeutically effective amount of the anti-CD20 antibody of claim 1.

4. An anti-CD20 antibody comprising two light chains and two heavy chains, wherein the amino acid sequence of each light chain consists of SEQ ID NO: 29 and the amino acid sequence of each heavy chain consists of SEQ ID NO: 31.

5. The antibody of claim 4 consisting of two light chains and two heavy chains, wherein the amino acid sequence of each light chain consists of SEQ ID NO: 29 and the amino acid sequence of each heavy chain consists of SEQ ID NO: 31.

6. A pharmaceutical composition comprising the anti-CD20 antibody of claim 4 and a pharmaceutically acceptable carrier.

7. A method for treating lymphoma in a human comprising administering to the human a therapeutically effective amount of the anti-CD20 antibody of claim 4.

8. An isolated nucleic acid comprising a nucleic acid selected from the group consisting of:
   (a) a nucleic acid encoding a heavy chain wherein the amino acid sequence of the heavy chain consists of SEQ ID NO:31; and
   (b) a nucleic acid encoding a light chain and a heavy chain wherein the amino acid sequence of the light chain consists of SEQ ID NO:29 and wherein the amino acid sequence of the heavy chain consists of SEQ ID NO:31.

9. An expression vector comprising the nucleic acid molecule of claim 8.

10. A host cell comprising the vector of claim 9, wherein the host cell is a CHO, NSO, Sp2/0 or HEK293 cell.

11. The host cell of claim 10 that is a CHO cell.

12. A process of producing an anti-CD20 antibody comprising:
   (a) culturing a host cell according to claim 11 under conditions suitable for the expression of the antibody; and
   (b) purifying the antibody.

13. An anti-CD20 antibody produced by the process according to claim 12.

* * * * *

UNITED STATES PATENT AND TRADEMARK OFFICE
CERTIFICATE OF CORRECTION

PATENT NO.        : 7,740,847 B2
APPLICATION NO.   : 11/572634
DATED             : June 22, 2010
INVENTOR(S)       : Barrett Allan et al.

It is certified that error appears in the above-identified patent and that said Letters Patent is hereby corrected as shown below:

In the Specifications:

1) Column 1, line 4:
   Delete "Nos.; and PCT Application Ser."

2) Column 1, line 8:
   Delete "entirely" and
   Insert --entirety--, therefor.

Signed and Sealed this

Nineteenth Day of October, 2010

David J. Kappos
*Director of the United States Patent and Trademark Office*